US011541116B1

(12) United States Patent
Viswanathan et al.

(10) Patent No.: US 11,541,116 B1
(45) Date of Patent: Jan. 3, 2023

(54) METHODS AND COMPOSITIONS FOR INDUCING FERROPTOSIS IN VIVO

(71) Applicant: Kojin Therapeutics, Inc., Boston, MA (US)

(72) Inventors: Vasanthi Viswanathan, Arlington, MA (US); John Kittridge Eaton, Jr., Somerville, MA (US)

(73) Assignee: Kojin Therapeutics, Inc., Boston, MA (US)

( * ) Notice: Subject to any disclaimer, the term of this patent is extended or adjusted under 35 U.S.C. 154(b) by 0 days.

(21) Appl. No.: 17/571,411

(22) Filed: Jan. 7, 2022

(51) Int. Cl.
  A61K 45/06 (2006.01)
  A61P 35/00 (2006.01)
  A61K 9/00 (2006.01)

(52) U.S. Cl.
  CPC ............. *A61K 45/06* (2013.01); *A61P 35/00* (2018.01); *A61K 9/0019* (2013.01)

(58) Field of Classification Search
  None
  See application file for complete search history.

(56) References Cited

U.S. PATENT DOCUMENTS

| | | | |
|---|---|---|---|
| 5,112,954 A | 5/1992 | Abrams |
| 5,171,885 A | 12/1992 | Griffith |
| 5,294,736 A | 3/1994 | Griffith |
| 5,476,966 A | 12/1995 | Anderson |
| 5,523,077 A | 6/1996 | Pawelek |
| 8,163,796 B1 | 4/2012 | Johnson |
| 9,023,871 B2 | 5/2015 | Maltese |
| 9,028,796 B2 | 5/2015 | Maltese |
| 9,061,994 B1 | 6/2015 | Maltese |
| 9,580,398 B2 | 2/2017 | Stockwell |
| 9,695,133 B2 | 7/2017 | Stockwell |
| 9,802,956 B2 | 10/2017 | Conrad et al. |
| 9,850,483 B2 | 12/2017 | Clarke |
| 9,862,678 B2 | 1/2018 | Vandenabeele |
| 9,938,245 B2 | 4/2018 | Stockwell |
| 10,087,175 B2 | 10/2018 | Hawkins |
| 10,233,171 B2 | 3/2019 | Stockwell |
| 10,238,631 B2 | 3/2019 | Shyur |
| 10,259,775 B2 | 4/2019 | Stockwell |
| 10,344,029 B2 | 7/2019 | Hawkins |
| 10,597,381 B2 | 3/2020 | Stockwell |
| 10,647,687 B2 | 5/2020 | Conrad |
| 10,736,972 B2 | 8/2020 | Bradbury |
| 10,947,188 B2 | 3/2021 | Stockwell |
| 10,975,069 B2 | 4/2021 | Hawkins |
| 11,040,964 B2 | 6/2021 | Jiang |
| 11,065,221 B2 | 7/2021 | Shytaj |
| 11,078,236 B2 | 8/2021 | Ratan |
| 11,192,849 B2 | 12/2021 | Stockwell |
| 11,234,963 B2 | 2/2022 | Orwar |
| 11,246,946 B2 | 2/2022 | Bradbury |
| 11,339,124 B2 | 5/2022 | Vandenabeele |
| 2004/0002151 A1 | 1/2004 | Watt et al. |
| 2004/0197315 A1 | 10/2004 | Stefanis |
| 2007/0161644 A1 | 7/2007 | Stockwell |
| 2011/0124032 A1 | 5/2011 | Diehn |
| 2012/0309087 A1 | 12/2012 | Wolf |
| 2013/0071369 A1 | 3/2013 | Mastaloudis |
| 2016/0046616 A1 | 2/2016 | Biswal |
| 2017/0015660 A1 | 1/2017 | Hawkins |
| 2017/0037404 A1 | 2/2017 | Brown |
| 2017/0112809 A1 | 4/2017 | Orwar |
| 2018/0078601 A1 | 3/2018 | Mastaloudis |
| 2018/0110770 A1 | 4/2018 | Gao |
| 2018/0120336 A1 | 5/2018 | Van Tine |
| 2018/0169264 A1 | 6/2018 | Bradbury |
| 2018/0327456 A1 | 11/2018 | Ratan |
| 2019/0008961 A1 | 1/2019 | Chattopadhyay |
| 2019/0134172 A1 | 5/2019 | Gunn |
| 2019/0151679 A1 | 5/2019 | Nam |
| 2019/0262306 A1 | 8/2019 | Bach |
| 2019/0263802 A1 | 8/2019 | Jiang |
| 2019/0292135 A1 | 9/2019 | Stockwell |
| 2019/0315681 A1 | 10/2019 | Stockwell |
| 2020/0138829 A1 | 5/2020 | Chen |
| 2020/0147060 A1 | 5/2020 | Schultz |
| 2020/0163966 A1 | 5/2020 | Graeber |
| 2020/0181194 A1 | 6/2020 | Xiang |
| 2020/0222452 A1 | 7/2020 | Grimm |
| 2020/0222453 A1 | 7/2020 | Tour |
| 2020/0255838 A1 | 8/2020 | Kim et al. |
| 2020/0261498 A1 | 8/2020 | Lee |

(Continued)

FOREIGN PATENT DOCUMENTS

| EP | 23208691 A | 5/2011 |
|---|---|---|
| WO | WO-2020138385 A1 | 7/2020 |

(Continued)

OTHER PUBLICATIONS

Liu et al., European Review for Medical and Pharmacological Sciences (2020), 24(21), pp. 11323-11333.*
Lu et al., Frontiers in Pharmacology (2018), vol. 8, article 992, pp. 1-8.*
Fujihara et al., Antioxidants (2021), 10, 986, 11 pages.*
Badgley, M. A., et al. Cysteine depletion induces pancreatic tumor ferroptosis in mice. Science. Apr. 3, 2020;368(6486):85-89. doi: 10.1126/science.aaw9872.
Conrad et al. "Selenium: Tracing Another Essential Element of Ferroptotic Cell Death." Cell Chemical Biology 27:4 (2020).
Eaton JK, et al. Selective covalent targeting of GPX4 using masked nitrile-oxide electrophiles. Nat Chem Biol. May 2020;16(5):497-506. doi: 10.1038/s41589-020-0501-5. Epub Mar. 30, 2020.

(Continued)

*Primary Examiner* — Brian J Davis
(74) *Attorney, Agent, or Firm* — Greenberg Traurig, LLP

(57) ABSTRACT

Methods and systems for the induction of ferroptosis in a tissue in a subject are provided. Various ferroptosis-inducing agents a described. Various methods of administration are described for optimal ferroptosis induction and killing of target cells.

19 Claims, 7 Drawing Sheets

(4 of 7 Drawing Sheet(s) Filed in Color)

(56) References Cited

U.S. PATENT DOCUMENTS

| | | |
|---|---|---|
| 2020/0316219 A1 | 10/2020 | Bradbury |
| 2020/0383943 A1 | 12/2020 | Bradbury |
| 2020/0397817 A1 | 12/2020 | Shieh |
| 2020/0397853 A1 | 12/2020 | Tzahor |
| 2020/0397854 A1 | 12/2020 | Berna |
| 2021/0002296 A1 | 1/2021 | Mainolfi et al. |
| 2021/0003582 A1 | 1/2021 | Kang |
| 2021/0040079 A1 | 2/2021 | Yang |
| 2021/0094909 A1 | 4/2021 | Vandenabeele |
| 2021/0121569 A1 | 4/2021 | Bradbury |
| 2021/0145985 A1 | 5/2021 | Bradbury |
| 2021/0206736 A1 | 7/2021 | Keefe |
| 2021/0220494 A1 | 7/2021 | Bradbury |
| 2021/0244715 A1 | 8/2021 | Cao |
| 2021/0251994 A1 | 8/2021 | Barsotti |
| 2021/0283089 A1 | 9/2021 | Chen |
| 2021/0284598 A1 | 9/2021 | Zhang |
| 2021/0290721 A1 | 9/2021 | Mastaloudis et al. |
| 2021/0292305 A1 | 9/2021 | Zhang |
| 2021/0292315 A1 | 9/2021 | Song |
| 2021/0299107 A1 | 9/2021 | Stockwell |
| 2021/0299276 A1 | 9/2021 | Gordon |
| 2021/0317146 A1 | 10/2021 | Keefe |
| 2021/0386698 A1 | 12/2021 | Nichenametla |
| 2022/0002280 A1 | 1/2022 | Jiang |
| 2022/0031674 A1 | 2/2022 | Schultz |
| 2022/0106362 A1 | 4/2022 | Ratan |
| 2022/0118106 A1 | 4/2022 | Bradbury |
| 2022/0144826 A1 | 5/2022 | Warner |
| 2022/0193047 A1 | 6/2022 | Stockwell |

FOREIGN PATENT DOCUMENTS

| | | |
|---|---|---|
| WO | 2020172343 | 8/2020 |
| WO | 2020205919 A1 | 10/2020 |
| WO | 2020230701 A1 | 11/2020 |
| WO | WO-2021041539 A2 | 3/2021 |
| WO | WO-2021119215 A1 | 6/2021 |
| WO | 2021132592 | 7/2021 |
| WO | 2021163033 A1 | 8/2021 |
| WO | 2021175192 | 9/2021 |
| WO | 2021239817 | 12/2021 |
| WO | 2022020150 A1 | 1/2022 |
| WO | 2022082078 A1 | 4/2022 |

OTHER PUBLICATIONS

Eaton JK, Furst L, Cai LL, Viswanathan VS, Schreiber SL. Structure-activity relationships of GPX4 inhibitor warheads. Bioorg Med Chem Lett. 2020;30(23):127538. doi:10.1016/j.bmcl.2020.127538.

Eaton JK, Ruberto RA, Kramm A, Viswanathan VS, Schreiber SL. Diacylfuroxans Are Masked Nitrile Oxides That Inhibit GPX4 Covalently. J Am Chem Soc. Dec. 26, 2019;141(51):20407-20415. doi: 10.1021/jacs.9b10769. Epub Dec. 16, 2019.

Hangauer, M., Viswanathan, V., Ryan, M. et al. "Drug-tolerant persister cancer cells are vulnerable to GPX4 inhibition." Nature 551, 247-250 (2017). https://doi.org/10.1038/nature24297.

Jonas et al. "An implantable microdevice to perform high-throughput in vivo drug sensitivity testing in tumors." Science Translational Medicine. vol. 7: Issue 284 (2015).

Viswanathan et al. "Dependency of a therapy-resistant state of cancer cells on a lipid peroxidase pathway." Nature (2017); 547(7664): 453-457.

Yang WS, et al. Regulation of ferroptotic cancer cell death by GPX4. Cell. Jan. 16, 2014;156(1-2):317-331. doi: 10.1016/j.cell. 2013.12.010.

Zou Y, et al., A GPX4-dependent cancer cell state underlies the clear-cell morphology and confers sensitivity to ferroptosis. Nat Commun. Apr. 8, 2019;10(1):1617. doi: 10.1038/s41467-019-09277-9.

Wu et al., Chaperone-mediated autophagy is involved in the execution of ferroptosis, PNAS, vol. 116, No. 8, p. 2996-3005, (2019).

Zheng, J., et al., "Sorafenib fails to trigger ferroptosis across a wide range of cancer cell lines" Cell Death Dis 12, 698 (2021). https://doi.org/10.1038/s41419-021-03998-w.

Dixon, S.J., et al., "Pharmacological inhibition of cystine-glutamate exchange induces endoplasmic reticulum stress and ferroptosis", Elife, May 20, 2014;3:e02523, 25 pages, doi: 10.7554/eLife.02523.

Li J, et al., "Ferroptosis: past, present and future", Cell Death Dis Feb. 3, 2020;11(2):88, 13 pages, doi: 10.1038/s41419-020-2298-2.

* cited by examiner

Representative background illustration of a ferroptotis pathway

METHODS AND COMPOSITIONS FOR INDUCING FERROPTOSIS IN VIVO

BACKGROUND

Diseases such as cancer, autoimmune diseases, and fibrosis manifest when cells in the body exhibit uncontrolled, abnormal cell growth and proliferation. In order to treat hyperproliferative diseases, the standard of care therapies induce cell death by a cellular process called apoptosis. The apoptosis pathway is engaged by many common types of anti-cancer therapies and ionizing radiation, which contributes to the regression of tumors or the toxic side effects of treatment. Given the ability for hyperproliferative cells to resist cell death by current apoptosis-driven therapeutics, there is a need for the development of new methods of inducing cell death in hyperproliferative cells.

SUMMARY

In some embodiments, the methods provided herein comprise administering agents that induce iron-dependent cell death in vivo and in some cases recruit immune cells, for instance leukocytes to tumors treated with iron-dependent cell death agents including ferroptosis-inducing agents.

Provided herein are methods of inducing ferroptosis in a tissue in a subject, wherein the methods comprise: sustained administration of a therapeutic amount of a ferroptosis-inducing agent to a tissue, wherein the sustained administration of said therapeutic amount comprises providing to said tissue the ferroptosis-inducing agent in an amount sufficient to achieve a distribution of at least about 10 ng/mm$^2$ within said tissue for a period of at least 4 hours, thereby inducing ferroptosis in the tissue.

Further provided herein are methods of inducing iron-dependent cell death in a tissue in a subject, wherein the methods comprise: contacting a tissue in vivo with an effective amount of an iron-dependent cell death agent for a duration of time of at least 4 hours, wherein the tissue comprises one or more of: (a) a plurality of cells comprising a concentration of selenium greater than a selenium concentration in a corresponding normal tissue; (b) a plurality of cells comprising a concentration of iron greater than an iron concentration in a corresponding normal tissue; (c) a plurality of cells comprising a PUFA concentration greater than a PUFA concentration in a corresponding normal tissue; (d) a plurality of cells expressing one or more markers indicative of a mesenchymal state; and/or (e) a plurality of cells comprising a peroxidizability index (PI) greater than a PI in a corresponding normal tissue, wherein the effective amount of the iron-dependent cell death agent is a concentration of at least about 0.1 μM up to 500 μM in the tissue for the duration of time.

Further provided herein are methods of inducing targeted cell death in a mammalian tissue in vivo, wherein the methods comprise: (a) contacting a mammalian tissue with a priming agent; (b) contacting the mammalian tissue in vivo with an effective amount of a ferroptosis-inducing agent for a duration of time of at least 4 hours, when a plurality of cells within the mammalian tissue are responsive to the priming agent as determined by detecting in the mammalian tissue: (i) a plurality of cells comprising a concentration of selenium greater than a selenium concentration in the mammalian tissue prior to contacting with the priming agent; (ii) a plurality of cells comprising a concentration of iron greater than an iron concentration in the mammalian tissue prior to contacting with the priming agent; (iii) a plurality of cells comprising a PUFA concentration greater than a PUFA concentration in the mammalian tissue prior to contacting with the priming agent; (iv) a plurality of cells expressing one or more markers indicative of a mesenchymal state; (v) a plurality of cells comprising a peroxidizability index (PI) greater than a PI in the mammalian tissue prior to contacting with the priming agent; and/or (vi) hyperproliferation of cells in the mammalian tissue, wherein the ferroptosis-inducing agent induces targeted cell death in the mammalian tissue in vivo.

Further provided herein are methods of modulating ferroptosis in vivo, wherein the methods comprise: (a) contacting a mammalian tissue in vivo with an effective amount of a ferroptosis-inducing agent for a duration of time of at least 4 hours, wherein the ferroptosis-inducing agent induces targeted cell death in the mammalian tissue in vivo; and (b) contacting the mammalian tissue in vivo with an effective amount of a ferroptosis-inducing agent and a ferroptosis inhibitor, thereby modulation ferroptosis in vivo.

Further provided herein are systems, wherein the systems comprise: an implantable microdevice configured for localized administration to a tissue comprising: (a) a cylindrical support structure having at least one microwell on a surface of or formed within the support structure; (b) a microdose of a ferroptosis-inducing agent in the at least one microwell; and (c) a compound release mechanism for sustained administration for controlling a release of the ferroptosis-inducing agent from the microwell, wherein the microdose of the ferroptosis-inducing agent forms a gradient of a sub-therapeutic dose of the ferroptosis-inducing agent an administration site within the tissue for a duration of time of at least 4 hours, wherein the microdevice is configured to permit implantation into the tissue using a catheter, cannula or biopsy needle, and wherein the microdevice is further configured to release the ferroptosis-inducing agent from the at least one microwell to the administration site within the apoptosis-resistant tissue adjacent to the at least one microwell.

Further provided herein are systems for identifying ferroptosis induction in an animal model comprising: (a) an animal model comprising a target tissue of interest; (b) a microdevice configured to permit implantation into a tissue in the animal model using a catheter, cannula or biopsy needle comprising: (i) at least one microwell containing one or more active agents; (ii) a micro-dose of the one or more active agents in the at least one microwell; and (iii) a compound release mechanism comprising a polymeric matrix for controlling the release of the one or more active agents from the microwell into the tissue; wherein the system measures an outcome of ferroptosis induction in the animal model after administration of the one or more active agents into the tissue relative to a baseline tissue without administration of the one or more active agents, and identifying one or more active agents induces ferroptosis in the tissue.

Further provided herein are systems for screening for ferroptosis-induced cell death in vivo, the systems comprising: (a) an animal model comprising a target tissue of interest; (b) a microdevice configured to permit implantation into a tissue in the animal model using a catheter, cannula or biopsy needle comprising: (i) at least one microwell containing one or more active agents; (ii) at least one microwell containing one or more ferroptosis inhibitors; (ii) a microdose of the one or more active agents; and/or one or more ferroptosis inhibitors in the at least one microwell; and (iii) a compound release mechanism comprising a polymeric matrix for controlling the release of the one or more active agents from the microwell into the tissue; wherein the system measures an outcome of ferroptosis induction in the animal model after administration of the one or more active agents into the tissue relative to a baseline tissue without administration of the one or more active agents, wherein the system measures an outcome of ferroptosis induction in the animal model after administration of the one or more active agents into the tissue relative to administration of the one or more active agents and one or more ferroptosis inhibitors, and identifying one or more active agents induces ferroptosis in the tissue Further provided herein are compositions for the treatment of a disease or disorder, wherein the compositions comprise any one of the agents in Table 1 or a combination of agents; and a system provided herein.

Further provided herein are pharmaceutical compositions for the treatment of a disease or disorder, wherein the pharmaceutical compositions comprise any one of the agents in Table 1 or a combination of agents; and a pharmaceutically acceptable excipient.

BRIEF DESCRIPTION OF THE DRAWINGS

The patent or application file contains at least one drawing executed in color. Copies of this patent or patent application publication with color drawings will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows cleaved caspase-3 staining. Dashed lines indicate region of drug exposure. FIG. 2B shows a graph demonstrating the fractional viability (y-axis) of cells over time (x-axis) for ferroptosis-inducing compound (A) and for ferroptosis-inducing compound (A)+anti-ferroptosis rescue agent (N).

FIG. 5A shows a tumor section stained for cleaved caspase-3. Dashed lines indicate region of drug exposure. Scale bar: 100 micrometers (μm). FIG. 5B shows representative H&E images at 18 hrs post treatment with (1) ferroptosis-inducing compound (C) or (2) ferroptosis-inducing compound (C)+anti-ferroptosis rescue agent (M) as indicated.

DETAILED DESCRIPTION OF THE DISCLOSURE

Figure 1:
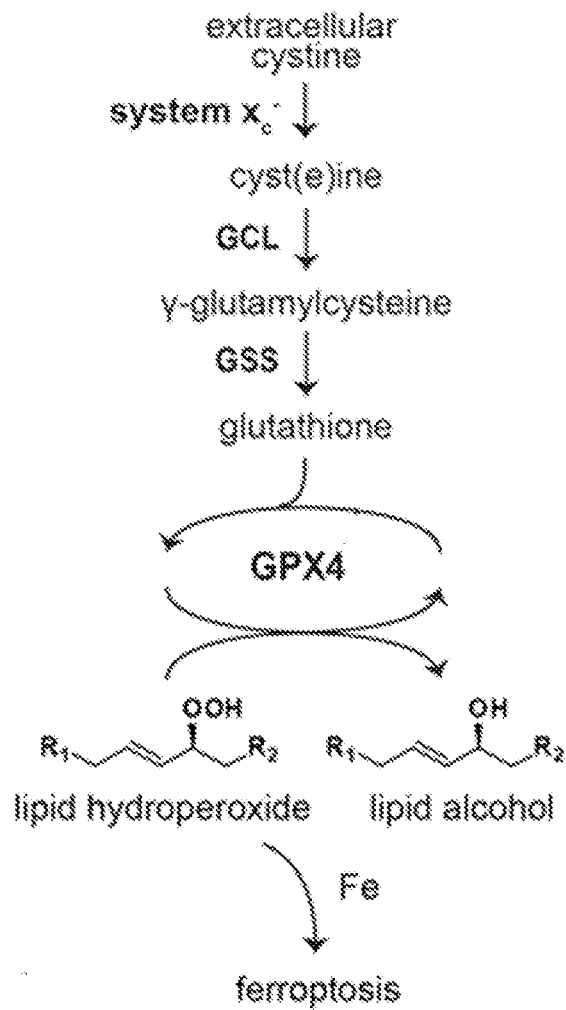
FIG. 1 is a schematic representation of the ferroptosis pathway.

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Definitions

Throughout this disclosure, various embodiments can be presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

Unless specifically stated or obvious from context, as used herein, the term "about" is understood as within a range of normal tolerance in the art, for example within 2 standard deviations of the mean. "About" can be understood as within 15%, 14%, 13%, 12%, 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about." Where particular values are described in the application and claims, unless otherwise stated, the term "about" is implicit and in this context means within an acceptable error range for the particular value.

Unless otherwise stated, structures depicted herein are also meant to include all isomeric (e.g., enantiomeric, diastereomeric, geometric (or conformational) forms of the structure; for example, the L and S designations for each asymmetric center, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, compounds with one or more asymmetric centers referred to herein, include enantiopure, diastereomeric, and racemic mixtures thereof.

The term "adjacent" and its grammatical equivalents as used herein refer to right next to the object of reference. For example, the term adjacent in the context of a cell or a tissue can mean without any other cells or tissues in between.

The term "analog" and its grammatical equivalents as used herein refer to a molecule that is not identical, but has analogous structural features. An analog of a drug or agent is a drug or agent that is related to a reference agent (e.g., an agent provided in Table 1), but whose chemical structure can be different. Generally, analogues exhibit similar activities to a reference drug or agent, but the activity can be increased or decreased or otherwise improved. Generally, an analogue form of a compound or drug means that the backbone core of the structure is modified or changed compared to a reference drug.

The term "anti-cancer agent" or "chemotherapeutic agent" and its grammatical equivalents as used herein refer to an agent that is capable of killing cells that divide rapidly (e.g., cancer cells). Exemplary anti-cancer agents provided herein can be used in combination with a ferroptosis-inducing agent and/or an iron-dependent cell death inducing agent.

The term "cancer" and its grammatical equivalents as used herein refer to a hyperproliferation of cells whose unique trait—loss of normal controls—results in unregulated growth, lack of differentiation, local tissue invasion, and metastasis. With respect to the methods provided herein, the cancer can be any cancer, including but not limited to any one of: acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal cancer, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, colorectal cancer, renal cancer, skin cancer, small intestine cancer, soft tissue cancer, solid tumors, stomach cancer, testicular cancer, thyroid cancer, ureter cancer, and/or urinary bladder cancer. As used herein, the term "tumor" refers to an abnormal growth of cells or tissues, e.g., of malignant type or benign type.

The term "drug resistant cancer" and its grammatical equivalents as used herein refers to a cancer that does not respond, or exhibits a decreased response to, one or more chemotherapeutic agents.

The term "effective amount" or "therapeutically effective amount" and its grammatical equivalents refers to an amount that is sufficient to achieve or at least partially achieve the desired effect.

The term "expression" and its grammatical equivalents as used herein refers to the biosynthesis of a gene product. For example, in the case of a structural gene, expression involves transcription of the structural gene into mRNA and the translation of mRNA into one or more polypeptides.

The term "ferroptosis" refers to a form of cell death involving generation of reactive oxygen species mediated by iron, and characterized by, in part, lipid peroxidation. The term "ferroptosis-inducing agent" or "ferroptosis activator" or "ferroptosis inducer" or "ferroptosis-inducing compound" refers to an agent which promotes or activates ferroptosis in a cell.

The term "hyperproliferative cells" and its grammatical equivalents as used herein refers to cells characterized by unwanted cell proliferation, or abnormally high rate or sustained cell division, unrelated or uncoordinated with that of surrounding normal tissue.

The term "in vitro" and its grammatical equivalents as used herein refers to events that occur in an artificial environment, e.g., in a test tube or reaction vessel, in cell culture, etc., rather than within a multi-cellular organism.

The term "in vivo" and its grammatical equivalents as used herein refers to events that occur within a multi-cellular organism, such as a non-human animal.

The term "iron-dependent cell death agent" and its grammatical equivalents as used herein refers to an agent which induces, promotes or activates cell death mediated by iron. In some cases within the disclosure, the term "iron-dependent cell death agent" is used interchangeably with ferroptosis-inducing agent.

The term "normal cells" and its grammatical equivalents as used herein refers to cells that undergo controlled cell division, controlled activation, or quiescent cells.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Overview

Provided herein are compositions and methods useful for treating a disease or condition. Provided herein are also treatment regimes for the therapy of various diseases or conditions such as cancer. A treatment regime can comprise administering a ferroptosis-inducing agent or an iron-dependent cell death agent. Provided herein are methods, compositions and uses thereof for inducing ferroptosis in a subject in vivo. Briefly, further described herein are (1) methods of characterizing ferroptosis-sensitive cells; (2) cell death-inducing agents including ferroptosis-inducing agents, and chemotherapeutic agents; (3) pharmaceutical compositions; (4) dosing; (5) methods of administration; (6) efficacy; (7) therapeutic applications; and (8) systems.

Ferroptosis

Cell death is a cellular process involved in development, cellular homeostasis, and prevention of proliferative diseases such as cancer. Programmed cell death can take different forms, such as apoptosis, mitotic catastrophe, necrosis, senescence, and autophagy. While each of these processes ultimately lead to cell death, the pathways and mechanisms appear to be unique, both at the molecular and cellular level.

Ferroptosis is a non-apoptotic, oxidative form of regulated cell death involving lipid hydroperoxides and the accumulation of lipid peroxide at the cellular plasma membrane. Cells undergoing ferroptosis do not display the cellular characteristics or functions associated with apoptosis, the canonical form of cell death. Examples of apoptotic cell features include, e.g., mitochondrial cytochrome c release, caspase activation, and chromatin fragmentation. Ferroptosis is also characterized by increased levels of intracellular reactive oxygen species (ROS) which can be prevented by iron chelation and genetic inhibition of cellular iron uptake. Addition of iron, but not by other divalent transition metal ions, can potentiate ferroptosis signaling in cells.

Cellular components implicated in and regulating ferroptosis include, among others, cysteine-glutamate antiporter (system Xc), glutathione peroxidase 4 (GPX4), p53, cargo receptor NCOA4, glutathione synthetase (GSH), glutamate-cysteine ligase (GCL). The inactivation or inhibition of some of these molecules, for example, system Xc, GPX4, or glutathione synthetase leads to iron-dependent cell death or ferroptosis.

Hyperproliferative cells in a drug-resistant state, such as, e.g., drug resistant cancer cells have been found to exhibit a dysregulation in apoptosis cellular pathways. Surprisingly, drug-resistance to apoptotic agents by hyperproliferative cells can have an enhanced ability to undergo ferroptosis. Apoptosis-resistant cells can be killed via ferroptosis induction due to their "flammable" ferroptosis-sensitive state.

Methods of Characterizing Ferroptosis-Sensitive Cells

Provided herein are methods of identifying and characterizing a ferroptosis-sensitive cell in a subject. In some embodiments, the characterizing is performed prior to treatment of a subject with a ferroptosis-inducing agent provided herein. Ferroptosis-sensitive cells can be identified by the following properties provided herein: (1) a concentration of selenium greater than a selenium concentration in a corresponding normal cell; (2) a concentration of iron greater than an iron concentration in a corresponding normal cell; (3) a polyunsaturated fatty acid (PUFA) concentration greater than a PUFA concentration in a corresponding normal cell; (4) a peroxidizability index (PI) greater than a PI in a corresponding normal tissue; and/or (5) the expression of one or more markers indicative of a mesenchymal state, among other morphological and histological characteristics. Methods of measuring analyte concentrations of selenium, iron, and PUFAs include, e.g., mass spectrometry, chromatography, immunoassays, immunosorbent assays, absorbance and colorimetric assays, and microwave plasma—atomic emission spectroscopy. Methods of measuring markers of a mesenchymal cell state include, e.g., immunoassays, polymerase chain reaction (PCR) assays, and sequencing assays.

(1) Selenium (Se) Concentration and Selenoproteins

Selenium (Se) is a micronutrient that facilitates the synthesis of selenoproteins in a cell. Dietary selenium is found in meat, nuts, cereals, mushrooms, and vegetables. The selenium content in the human body ranges from about 13 milligrams (mg) to 20 mg. Selenium is involved in the cellular process of selenoprotein synthesis and ferroptosis. Selenoproteins are rare proteins that comprise a selenocysteine (Sec) residue in the place of a cysteine. Non-limiting examples of selenoproteins include GPX1, GPX2, GPX3, GPX4, GPX6, TXNRD1, TXNRD2 (TXRD2), TXNRD3, DIO1, DIO2, DIO3, SEPHS2, SEPS1, SEPP1, SEP15, SEPN1 (SELENON), SEPX1, SEPW1 (SELENOW), SEPT1, SELH, SEL1, SELK, SELM (SELENOM), SELO, and SELV. Selenoproteins exhibit biochemical activities such as oxidoreduction, selenocysteine synthesis, and/or selenium transport. GPX4 is a phospholipid hydroperoxidase that catalyzes the reduction of hydrogen peroxide and organic peroxides, thereby protecting cells against membrane lipid peroxidation, and oxidative stress. GPX4 is a regulator of the ferroptosis pathway and inhibition of GPX4 induces ferroptotic cell death.

Provided herein are methods of identifying a ferroptosis-sensitive cell in a mammalian tissue by the concentration of selenium. In some embodiments, methods provided herein comprise measuring the concentration of selenium (Se) in a cell, a plurality of cells, or a mammalian tissue. In some embodiments, the Se concentration in a cell or the plurality of cells of the mammalian tissue is greater than the Se concentration in cells of healthy tissue by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In some embodiments, the Se concentration in the plurality of cells of the mammalian tissue is greater than the Se concentration in cells of healthy tissue by 1%-10%, 10%-20%, 20%-30%, 30%-40%, 40%-50%, 50%-60%, 60%-70%, 70%-80%, 80%-90%, or 90%-100%. In some embodiments, methods provided herein comprise administering to a mammal an effective amount of a ferroptosis-inducing agent, wherein a plurality of cells of a mammalian tissue have a selenium concentration greater than the selenium concentration of cells of a normal or healthy tissue; and ferroptosis is induced in the plurality of cells.

(2) Iron Concentration

Ferroptosis is an iron-dependent cellular process and ferroptosis-sensitive cells have increased concentrations of intracellular iron compared with normal cells. Cells treated with deferoxamine (DFO), an iron chelator used for treating iron overload and an agent reported to block ferroptosis, can inhibit cell death. Alternatively, iron loading into cells by treatment with ferric ammonium citrate (FAC) is sufficient to mimic particle treatment and induce ferroptosis in amino acid-starved cells. Increased iron uptake in cells can lead to the depletion of glutathione, conceivably due to increased ROS generation which results in ferroptosis induction.

Provided herein are methods of identifying a ferroptosis-sensitive cell in a mammalian tissue by the concentration of iron. In some embodiments, methods provided herein comprise measuring the concentration of iron or iron oxide in a cell, a plurality of cells, or a mammalian tissue. In some embodiments, the ferroptosis-sensitive cells comprises an increased intracellular concentration of iron that is at least about 7 parts per billion (ppb) or more, about 8 ppb or more, about 9 ppb or more, about 10 ppb or more, about 20 ppb or more, about 30 ppb or more, about 40 ppb or more, about 50 ppb or more, about 60 ppb or more, about 70 ppb or more, about 80 ppb or more, about 90 ppb or more, about 100 ppb or more, about 110 ppb or more, about 120 ppb or more, about 130 ppb or more, about 140 ppb or more, about 150 ppb or more, about 160 ppb or more, up to 170 ppb. In some embodiments, the ferroptosis-sensitive cells comprise an increased intracellular concentration of iron that is at least about 2 micromolar ($\mu$M) or higher, 2.5 $\mu$M or higher, 3.0 $\mu$M or higher, 4.0 $\mu$M or higher, 5.0 $\mu$M or higher, up to 10 $\mu$M higher than that of normal cells. In some embodiments, the iron concentration in a cell or the plurality of cells of the mammalian tissue is greater than the iron concentration in cells of healthy tissue by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In some embodiments, the iron concentration in the plurality of cells of the mammalian tissue is greater than the iron concentration in cells of healthy tissue by 1%-10%, 10%-20%, 20%-30%, 30%-40%, 40%-50%, 50%-60%, 60%-70%, 70%-80%, 80%-90%, or 90%-100%. In some embodiments, methods provided herein comprise administering to a mammal an effective amount of a ferroptosis-inducing agent, wherein a plurality of cells of a mammalian tissue has an iron concentration greater than the iron concentration of cells of a normal or healthy tissue; and ferroptosis is induced in the plurality of cells.

(3) PUFA Status

Apoptosis-resistant cells gain advantages by being in a ferroptosis-sensitive state with high levels of polyunsaturated fatty acids (PUFA). Apoptosis-resistant cells can be killed via ferroptosis induction due to their "flammable" high-PUFA state. The flammable state is defined by high membrane abundance of PUFAs (vs. MUFA, monosaturated fatty acids), which are prone to uncontrolled lipid peroxidation—a radical chain reaction of polyunsaturated fatty acids—that leads to ferroptotic cell death.

PUFAs are categorized as omega-3 (n-3) and omega-6 (n-6) depending on the location of the last double bond with reference to the terminal methyl end of the molecule. Non-limiting examples of PUFAs include: hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, Timnodonic acid), heneicosapentaenoic acid (HPA), docosapentaenoic acid (DPA, Clupanodonic acid), docosahexaenoic acid (DHA, Cervonic acid), tetracosahexaenoic acid (Nisinic acid), tetracosapentaenoic acid, linoleic acid (LA), gamma-linolenic acid (GLA), eicosadienoic acid, dihomo-gamma-linolenic acid (DGLA), arachidonic acid (AA), docosadienoic acid, adrenic acid (AdA), docosapentaenoic acid (Osbond acid), tetracosatetraenoic acid, and tetracosapentaenoic acid. Humans can synthesize all fatty acids utilized by the body except for linoleic acid (LA, C18:2n-6) and alpha-linolenic acid (ALA, C18:3n-3).

Provided herein are methods of identifying a ferroptosis-sensitive cell in a mammalian tissue by the concentration of PUFAs. In some embodiments, methods provided herein comprise administering to a mammal an effective amount of a ferroptosis-inducing agent, wherein a plurality of cells of a mammalian tissue has a polyunsaturated fatty acid (PUFA) concentration greater than the PUFA concentration of cells of a normal or healthy tissue; and ferroptosis is induced in the plurality of cells. In some embodiments, the PUFA concentration in the plurality of cells of the mammalian tissue is greater than the PUFA concentration in cells of healthy or non-malignant tissue of the mammal. In some embodiments, the PUFA concentration in the plurality of cells of the mammalian tissue is greater than the PUFA concentration in cells of healthy tissue by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In some embodiments, the PUFA concentration in the plurality of cells of the mammalian tissue is greater than the PUFA concentration in cells of healthy tissue by 1%-10%, 10%-20%, 20%-30%, 30%-40%, 40%-50%, 50%-60%, 60%-70%, 70%-80%, 80%-90%, or 90%-100%. In some embodiments, the PUFA concentration in the plurality of cells of the mammalian tissue is greater than a predetermined PUFA concentration. In some embodiments, the predetermined PUFA concentration is about 5, 10, 15, 20, 25, 30, 35, 40, 45, 50, 55, 60, 65, 70, 75, 80, 85, or 90 mole percent of total lipids. In some embodiments, the predetermined PUFA concentration is about 10-20, 20-30, 30-40, 40-50, 50-60, 60-70, 70-80, or 80-90 mole percent of total lipids. In some embodiments, the predetermined PUFA concentration is about 20 mole percent of total lipids.

(4) PI Index

Cell membrane composition must contain a sufficient threshold of polyunsaturated fatty acyl chains to support enzymatic and/or non-enzymatic lipid peroxidation. The peroxidizability of polyunsaturated fatty acids (PUFAs) is linearly dependent on the number of doubly allylic positions present in the molecules. The susceptibility of a cellular membrane to lipid peroxidation can be estimated using the peroxidizability index (PI), which is calculated from measured fatty acid composition (%, w/w) as follows: PI=(% dienoic×1)+(% trienoic×2)+(% tetraenoic×3)+(% pentaenoic×4)+(% hexaenoic×5). Alternatively, PI can be calculated as: PI=(% monoenoic acids×0.025)+(% dienoic acids×1)+(% trienoic acids×2)+(% tetraenoic acids×4)+(pentaenoic acids×6)+(hexaenoic acid×8). Lipidomic measurements of cellular membrane composition are used to determine the peroxidizability index. Cell lines with low PI values (<50) have low sensitivity to ferroptosis-inducing perturbations (e.g., GPX4 inhibition, GSH depletion, addition of pro-oxidant compounds). Cells are more susceptible to undergoing ferroptosis with increasing membrane PI values.

Cells grown in vitro have fatty acid profiles unlike those of cells in vivo and lower PI levels. Vertebrate cells are unable to synthesize PUFAs de novo and rely on dietary sources for such molecules. Typical cell culture methods use media supplemented with serum (typically 10%, v/v), which is the only source of exogenous lipids and contains 1% of the PUFAs available to cells in the body. As a result, cells grown in culture have half the PUFA levels of cells in vivo and double the amount of monounsaturated fatty acids (MUFAs).

The ferroptosis sensitivity of cell lines can be modulated by inclusion of fatty acids in the culture medium. Saturated fatty acids (SFAs), monounsaturated fatty acids (MUFAs), and deuterated PUFAs protect cells from undergoing ferroptosis while the addition of PUFAs increases cell sensitivity to ferroptosis-inducing perturbations. Supplementation of cell culture media with exogenous PUFAs can simulate in vivo PUFA concentrations and induce membrane compositions with higher PI values. Modulatory profiling assays with fatty acid supplementation and ferroptosis inducers allows for the experimental determination of specific membrane PUFA content and PI values sufficient for ferroptosis for a given cell line. For example, the peroxidizability index (PI) of sarcoma and other cancer cells is greater than nonmalignant tissue due to preferential uptake of PUFAs. Many sarcomas preferentially uptake PUFAs and incorporate polyunsaturated fatty acyl chains into membrane lipids, resulting in higher membrane peroxidizability index values (PI>100) versus nonmalignant tissue (average PI=91). The difference in membrane peroxidizability provides a therapeutic window for ferroptosis induction to selectively target sarcoma cells versus nonmalignant tissue. The more peroxidizable membrane state is consistent with observations of higher levels of lipid peroxidative stress in primary bone and soft tissue sarcoma. Addition of exogenous PUFAs can increase oxidative stress in osteogenic sarcoma cells and exhibit selective cytotoxic effects.

Provided herein are methods of identifying a ferroptosis-sensitive cell in a mammalian tissue by the peroxidizability index (PI). In some embodiments, methods provided herein comprise administering to a mammal an effective amount of a ferroptosis-inducing agent, wherein a plurality of cells of the mammalian tissue have a PI greater than the PI in cells of normal or healthy tissue; and ferroptosis is induced in the plurality of cells. In some embodiments, the PI in the plurality of cells of the mammalian tissue is greater than a predetermined PI. In some embodiments, the predetermined PI is about 50, 60, 70, 80, 90, 100, 110, 120, 130, 140, or 150. In some embodiments, the predetermined PI is about 90. In some embodiments, the PI in the plurality of cells of the mammalian tissue is greater than the PI in cells of healthy or non-malignant tissue by about 1%-10%, 10%-20%, 20%-30%, 30%-40%, 40%-50%, 50%-60%, 60%-70%, 70%-80%, 80%-90%, or 90%-100%.

(5) Mesenchymal Cell State

Therapy-resistant cells have three cellular and patient-derived signatures of high mesenchymal state. The first cellular signature is the expression of mesenchymal cell markers. Ferroptosis-sensitive cells exhibit a one or more marker of a mesenchymal cell state. Mesenchymal cell state markers that can be used to identify a ferroptosis-sensitive cell include but are not limited to: ZEB1, ACSL4, FADS2, PPARγ, Fsp1, SLC7A11, SLC3A2, and LPCAT3. The second cellular signature of a ferroptosis-sensitive cell is the reduced expression of endothelial cell markers as compared to normal cells. Non-limiting examples of endothelial cell markers include: vimentin, E-cadherin, and beta (β)-actin. The third cellular signature of a ferroptosis-sensitive cell is the sensitivity to GPX4 knockdown leading to cell death. GPX4 dependency is more pronounced in cancer cells adopting a therapy-resistant mesenchymal state as compared to normal mesenchymal cell lines. Methods of reducing or silencing GPX4 expression can be achieved, e.g., by CRISPR/Cas9, siRNA or shRNA, among others.

Provided herein are methods of identifying a ferroptosis-sensitive cell in a mammalian tissue by the expression of one or more mesenchymal cell state markers. In some embodiments, the methods provided herein comprise administering to a mammal an effective amount of a ferroptosis-inducing agent, wherein a plurality of cells of a mammalian tissue express one or more markers of a mesenchymal cell state; and ferroptosis is induced in the plurality of cells. In some embodiments, the expression of the mesenchymal cell marker in the plurality of cells of the mammalian tissue is greater than the expression of the mesenchymal cell marker in cells of healthy or non-malignant tissue by about 1%-10%, 10%-20%, 20%-30%, 30%-40%, 40%-50%, 50%-60%, 60%-70%, 70%-80%, 80%-90%, or 90%-100%.

(6) Additional Morphological Characteristics of Ferroptosis

Cells undergoing ferroptosis are characterized morphologically by the presence of smaller than normal mitochondria with condensed mitochondrial membrane densities, reduction or vanishing of mitochondria crista, and outer mitochondrial membrane rupture. Histology and immunoassays can be used to determine whether a tissue is cancerous, exhibits hyperplasia, or fibrosis, as well as identify ferroptosis-sensitive cells within a mammalian tissue. The cell membrane of cells in a ferroptotic state lack of rupture and blebbing of the plasma membrane normally associated with apoptosis. The nuclear size of ferroptotic cells is normal and lacks chromatin condensation.

In some embodiments, the methods provided herein comprise a step of obtaining a biological sample (e.g., blood sample or tissue biopsy) from a subject. In some embodiments, the methods provided herein further comprise fixing, processing, embedding, sectioning, and staining the biological sample for histological analysis. In some embodiments, the tissue comprises a histological abnormality. In some embodiments, the histological abnormality is determined by a tissue biopsy prior to or during the targeted, sustained administration of the ferroptosis-inducing agent to the tissue. In some embodiments, the histological abnormality is hyperplasia, vascularization/angiogenesis, or fibrosis. Hyperplasia is identified by an increased number of cells in a tissue as compared to a normal healthy tissue. Vascularization and angiogenesis are identified in a tissue sample by immunoassays for vascular markers, e.g., vascular endothelial growth factor (VEGF) and angiopoietin-2 (Ang2). Fibrosis is characterized by abnormal collagen deposits between cells identified in a tissue sample, e.g., by Masson's trichrome, Sirius red, or collagen staining.

Cell-Death and Ferroptosis-Inducing Agents

Provided herein are methods of inducing ferroptosis in a tissue in a subject, wherein the methods comprise: (a) sustained administration of a therapeutic amount of a ferroptosis-inducing agent; (b) contacting a tissue in vivo with an effective amount of an iron-dependent cell death agent for a duration of time; and/or (c) contacting a mammalian tissue with a priming agent and then contacting the mammalian tissue in vivo with an effective amount of a ferroptosis-inducing agent for a duration of time. Exemplary targets in the ferroptosis pathway are provided in FIG. 1.

The methods provided herein comprise administering to a cell, tissue, or subject an agent that modulates cell death. In some embodiments, the administering induces cell death. In some embodiments, the administering inhibits or rescues a cell from cell death. In some embodiments, the administering modulates ferroptosis. In some embodiments, the administering induces ferroptosis in vivo. In some embodiments, the administering inhibits ferroptosis in vivo. In some embodiments, the agent is a ferroptosis-inducing agent. In some embodiments, the agent is an iron-dependent cell death inducing agent. Agents useful in the induction of ferroptosis in vivo and for the treatment of a disease or disorder are discussed in further detail below.

(1) Ferroptosis-Inducing Agents and Iron Dependent Cell Death Inducing Agents

Provided herein are agents that induce ferroptosis in a tissue in a subject. In some embodiments, the agent is a small molecule, a peptide, or a nucleic acid. In some embodiments, the ferroptosis-inducing agent is an inhibitor of glutathione peroxidase 4 (GPX4), glutathione synthetase, glutamate-cysteine ligase, phosphoseryl-TRNA Kinase (PSTK), Eukaryotic Elongation Factor Selenocysteine-TRNA Specific (EEFSEC), Selenophosphate Synthetase 2 (SEPHS2), Sep (O-Phosphoserine) TRNA: Sec (Selenocysteine) TRNA Synthase (SEPSECS), or SECIS Binding Protein 2 (SECISBP2).

In some embodiments, the agent is an inhibitor of glutathione peroxidase 4 (GPX4). Glutathione peroxidase 4 (GPX4), also known as MCSP; SMDS; GPx-4; PHGPx; snGPx; GSHPx-4; snPHGPx, belongs to the glutathione peroxidase family, members of which catalyze the reduction of hydrogen peroxide, organic hydroperoxides and lipid hydroperoxides, and thereby protect cells against oxidative damage. GPX4 activation directly reduces phospholipid hydroperoxide levels in the cellular membrane. Several isozymes of this gene family exist in vertebrates, which vary in cellular location and substrate specificity. GPX4 has a high preference for lipid hydroperoxides and protects cells against membrane lipid peroxidation and cell death. This isozyme is also a selenoprotein, containing the rare amino acid selenocysteine (Sec) at its active site. Representative human GPX4 cDNA and human GPX4 protein sequences are publicly available from the National Center for Biotechnology Information (NCBI). Human glutathione peroxidase 4 peroxidase isoform B precursor (NM_001039847.3 and NP_001034936.1), isoform C (NM_001039848.4 and NP_001034937.1), isoform D (NM_001367832.1 and NP_001354761.1), isoform A precursor (NM_002085.5 and NP_002076.2).

Depletion of GPX4 induces lipid peroxidation-dependent cell death. Cancer cells in a drug-induced, therapy-resistant state have an enhanced dependence on the lipid peroxidase activity of GPX4 to prevent undergoing ferroptotic cell death. Lipophilic antioxidants, such as ferrostatin, can rescue cells from GPX4 inhibition-induced ferroptosis. For instance, mesenchymal state GPX4-knockout cells can survive in the presence of ferrostatin, however, when the supply of ferrostatin is terminated, these cells undergo ferroptosis. GPX4 inhibition can be rescued by blocking other components of the ferroptosis pathways, such as lipid ROS scavengers (ferrostatin, liproxstatin), lipoxygenase inhibitors, iron chelators and caspase inhibitors, which an apoptotic inhibitor does not rescue. Accordingly, a GPX4 inhibitor can be useful to induce ferroptotic cell death.

In some embodiments, the agent is an inhibitor of glutathione synthetase (GSS). Glutathione synthetase (GSS), also known as GSHS; HEL-S-64p; HEL-S-88n is a homodimer to catalyze the second step of glutathione biosynthesis, which is the ATP-dependent conversion of gamma-L-glutamyl-L-cysteine to glutathione. Representative human GSS cDNA and human GSS protein sequences are publicly available from the National Center for Biotechnology Information (NCBI). Human glutathione synthetase (NM_000178.4 and NP_000169.1, NM_001322494.1 and NP_001309423.1, NM_001322495.1 and NP_001309424.1).

In some embodiments, the agent is an inhibitor of glutamate-cysteine ligase (GCL). Glutamate-cysteine ligase (GCL), a central node in the ferroptosis pathway, has been overlooked as a target. Loss of GCL activity induces ferroptosis in sensitive cells and kills only the most ferroptosis-sensitive cells. Representative human GCL cDNA and human GCL protein sequences are publicly available from the National Center for Biotechnology Information (NCBI). Human glutamate-cysteine ligase catalytic subunit isoform b (NM_001197115.2 and NP_001184044.1, which lacks an in-frame exon in the 5' coding region, compared to variant 1. This results in a shorter protein (isoform b), compared to isoform a), and glutamate-cysteine ligase catalytic subunit isoform a (NM_001498.4 and NP_001489.1, which represents the longer transcript and encodes the longer isoform (a)).

In some embodiments, the agent is an inhibitor of phosphoseryl-TRNA Kinase (PSTK). PSTK is an enzyme that recruits selenocysteine, encoded by UGA. Sec is formed in a tRNA-dependent transformation of serine that is attached to tRNA Sec by seryl-tRNA synthetase. PSTK phosphorylates Ser-tRNA Sec to Sep-tRNA Sec which is then converted to Sec-tRNA Sec by Sep-tRNA: Sec-tRNA synthase (SepSecS). Representative human PSTK cDNA and human PSTK protein sequences are well-known in the art and are publicly available from the National Center for Biotechnology Information (NCBI). Human L-seryl-tRNA(Sec) kinase isoform 1 (NM_001363531.2 and NP_001350460.1), and L-seryl-tRNA(Sec) kinase isoform 2 (NM_153336.3 and NP_699167.2).

In some embodiments, the inhibitor is an inhibitor of Eukaryotic Elongation Factor Selenocysteine-TRNA Specific (EEFSEC). EEFSEC is also known as selenoprotein translation factor selb. Representative human EEFSEC cDNA and human EEFSEC protein sequences are publicly available from the National Center for Biotechnology Information (NCBI) as follows: selenocysteine-specific elongation factor (NM_021937.5 and NP_068756.2), selenocysteine-specific elongation factor isoform X4 (XM_024453695.1 and XP 024309463.1), selenocysteine-specific elongation factor isoform X3 (XM_024453694.1 and XP 024309462.1), selenocysteine-specific elongation factor isoform X1 (XM_024453692.1 and XP 024309460.1), selenocysteine-specific elongation factor isoform X2 (XM_024453693.1 and XP 024309461.1), selenocysteine-specific elongation factor isoform X5 (XM_005247696.3 and XP 005247753.1), selenocysteine-specific elongation factor isoform X7 (XM_011513066.2 and XP_011511368.1), and selenocysteine-specific elongation factor isoform X6 (XM_024453696.1 and XP_024309464.1). EEFSEC is a specialized translation elongation factor responsible for the co-translational incorporation of selenocysteine into proteins by recoding of a UGA stop codon in the presence of a downstream mRNA hairpin loop.

In some embodiments, the agent is an inhibitor of Selenophosphate Synthetase 2 (SEPHS2). Selenophosphate Synthetase 2 (SEPHS2) catalyzes the production of monoselenophosphate (MSP) from selenide and ATP. MSP is the selenium donor required for synthesis of selenocysteine (Sec), which is co-translationally incorporated into selenoproteins at in-frame UGA codons that normally signal translation termination. This protein is itself a selenoprotein containing a Sec residue at its active site, suggesting the existence of an autoregulatory mechanism. SEPHS2 is preferentially expressed in tissues implicated in the synthesis of selenoproteins and in sites of blood cell development. Further, genome-scale cancer-dependency profiling identifies selenoprotein synthesis enzymes as targets for ferroptosis induction. Loss of selenoprotein synthesis enzymes induces ferroptosis in sensitive cells. Moreover, Selenophosphate Synthetase 2 (SEPHS2) loss exhibits a novel two-pronged ferroptosis mechanism of action. SEPHS2 loss induced ferroptosis much more quickly than loss of other selenoprotein biosynthetic enzymes. SEPHS2 inhibitors can induce ferroptosis in certain diseases. For example, aggressive liver cancer is selectively targetable by SEPHS2 inhibition. Representative human SEPHS2 cDNA and human SEPHS2 protein sequences are well-known in the art and are publicly available from the National Center for Biotechnology Information (NCBI). Selenide, water dikinase 2 (NM_012248.4 and NP_036380.2).

In some embodiments, the agent is an inhibitor of Sep (O-Phosphoserine) TRNA: Sec (Selenocysteine) TRNA Synthase (SEPSECS). Sep (O-Phosphoserine) TRNA: Sec (Selenocysteine) TRNA Synthase (SEPSECS) catalyzes the third step in the process of selenocysteine synthesis, the conversion of O-phosphoseryl-tRNA(Sec) to selenocysteinyl-tRNA(Sec). Representative human SEPSECS cDNA and human SEPSECS protein sequences are publicly available from the National Center for Biotechnology Information (NCBI) as the follows: O-phosphoseryl-tRNA(Sec) selenium transferase (NM_016955.4 and NP_058651.3), O-phosphoseryl-tRNA(Sec) selenium transferase isoform X1 (XM_017008277.1 and XP_016863766.1), O-phosphoseryl-tRNA(Sec) selenium transferase isoform X5 (XM_017008278.1 and XP_016863767.1), O-phosphoseryl-tRNA(Sec) selenium transferase isoform X4 (XM_011513848.1 and XP_011512150.1), O-phosphoseryl-tRNA(Sec) selenium transferase isoform X2 (XM_011513846.2 and XP_011512148.1), and O-phosphoseryl-tRNA(Sec) selenium transferase isoform X3 (XM_011513847.2 and XP_011512149.1).

In some embodiments, the agent is an inhibitor of SECIS Binding Protein 2 (SECISBP2). SECISBP2 is one of the polypeptide components of the machinery involved in co-translational insertion of selenocysteine (Sec) into selenoproteins. Sec is encoded by the UGA codon, which normally signals translation termination. The recoding of UGA as Sec codon requires a Sec insertion sequence (SECIS) element; present in the 3' untranslated regions of eukaryotic selenoprotein mRNAs. This protein specifically binds to the SECIS element, which is stimulated by a Sec-specific translation elongation factor. Representative human SECISBP2 cDNA and human SECISBP2 protein sequences are publicly available from the National Center for Biotechnology Information (NCBI) as follows: Selenocysteine insertion sequence-binding protein 2 isoform 2 (NM_001282688.2 and NP_001269617.1), selenocysteine insertion sequence-binding protein 2 isoform 3 (NM_001282689.2 and NP_001269618.1), selenocysteine insertion sequence-binding protein 2 isoform 4 (NM_001282690.1 and NP_001269619.1), selenocysteine insertion sequence-binding protein 2 isoform 5 (NM_001354696.2 and NP_001341625.1), selenocysteine insertion sequence-binding protein 2 isoform 6 (NM_001354697.2 and NP_001341626.1), selenocysteine insertion sequence-binding protein 2 isoform 7 (NM_001354698.2 and NP_001341627.1), selenocysteine insertion sequence-binding protein 2 isoform 8 (NM_001354702.2 and NP_001341631.1), selenocysteine insertion sequence-binding protein 2 isoform 1 (NM_024077.5 and NP_076982.3), selenocysteine insertion sequence-binding protein 2 isoform X9 (XM_024447669.1 and XP_024303437.1), selenocysteine insertion sequence-binding protein 2 isoform X8 (XM_024447667.1 and XP_024303435.1), selenocysteine insertion sequence-binding protein 2 isoform X5 (XM_017015122.2 and XP_016870611.1), selenocysteine insertion sequence-binding protein 2 isoform X6 (XM_024447666.1 and XP_024303434.1), selenocysteine insertion sequence-binding protein 2 isoform X9 (XM_024447668.1 and XP_024303436.1), selenocysteine insertion sequence-binding protein 2 isoform X1 (XM_011519000.2 and XP_011517302.1), selenocysteine insertion sequence-binding protein 2 isoform X2 (XM_011519001.1 and XP_011517303.1), selenocysteine insertion sequence-binding protein 2 isoform X3 (XM_011519002.1 and XP_011517304.1), selenocysteine insertion sequence-binding protein 2 isoform X4 (XM_011519003.1 and XP_011517305.1), and selenocysteine insertion sequence-binding protein 2 isoform X7 (XM_006717282.2 and XP_006717345.1).

In some embodiments, the agent is an inhibitor of Nuclear factor-erythroid factor 2-related factor 2 (NRF2). NRF2 is a member of the cap 'n' collar (CNC) subfamily of basic region leucine zipper (bZip) transcription factors. NRF2 mediates induction of a set of drug-metabolizing enzymes, such as glutathione S-transferase (GST) and NAD(P)H: quinone oxidoreductase 1 (NQO1), by antioxidants and electrophiles. NRF2 also regulates GPX4 protein content, intracellular free iron content, and mitochondrial function, thereby modulating ferroptosis. NRF2 protein sequences are publicly available from the National Center for Biotechnology Information (NCBI) as the follows: Nrf2 [*Homo sapiens*], GenBank: AAB32188.1; and transcription factor Nrf2—human, PIR: 159340.

In some embodiments, the agent is an inhibitor of cystine transporter SLC7A11 (also called xCT). SLC7A11 (also commonly known as xCT) functions to import cystine for glutathione biosynthesis and antioxidant defense and is overexpressed in multiple human cancers. SLC7A11 (xCT) protein sequences are publicly available from the National Center for Biotechnology Information (NCBI) as the follows: cystine/glutamate transporter [*Homo sapiens*] NP_055146.1, and cystine/glutamate transporter isoform X1 [*Homo sapiens*] XP_011530104.1.

In some embodiments, the agent is an inhibitor of system Xc. System Xc-, also named cystine/glutamate antiporter, is an intracellular antioxidant element composed of the light chain SLC7A11 (xCT) and the heavy chain SLC3A2 (4F2hc) and functions as raw materials for the synthesis of glutathione (GSH). System Xc protein sequences are publicly available from the National Center for Biotechnology Information (NCBI) as the follows: cystine/glutamate transporter [*Homo sapiens*] NP_055146.1, cystine/glutamate transporter isoform X1 [*Homo sapiens*] XP_011530104.1, 4F2 cell-surface antigen heavy chain isoform f [*Homo sapiens*] NP_001013269.1, 4F2 cell-surface antigen heavy chain isoform c [*Homo sapiens*] NP_002385.3, 4F2 cell-surface antigen heavy chain isoform b [*Homo sapiens*] NP_001012680.1, and 4F2 cell-surface antigen heavy chain isoform e [*Homo sapiens*] NP_001012682.1.

In some embodiments, the agent is an inhibitor of thioredoxin reductase (TXNRD). TRXNRD is involved in reversible S-nitrosylation of cysteines in certain proteins. TRXNRD protein sequences are publicly available from the National Center for Biotechnology Information (NCBI) as the follows: thioredoxin reductase [*Homo sapiens*] AAB35418.1, thioredoxin reductase [*Homo sapiens*] AAF15900.1 GI: 6538774, thioredoxin reductase [*Homo sapiens*] AAD25167.1, thioredoxin reductase [*Homo sapiens*] AAD19597.1, and thioredoxin reductase [*Homo sapiens*] CAA04503.1.

In some embodiments, the agent is a statin. Exemplary statins include but are not limited to: atorvastatin, cerivastatin, fluvastatin, lovastatin, mevastatin, pitavastatin, pravastatin, rosuvastatin and simvastatin.

In some embodiments, the agent that induces ferroptosis in a tissue is selected from Table 1. Exemplary ferroptosis-inducing agents are provided in Table 1 along with their formula, chemical identifiers, and respective target and/or mechanism of action.

TABLE 1

Ferroptosis-inducing agents

| Name | Formula/ CAS | Structure | Target(s)/ Mechanism of Action |
|---|---|---|---|
| (1S,3R)-RSL3 | $C_{23}H_{21}ClN_2O_5$<br>Cas: 1219810-16-8 | 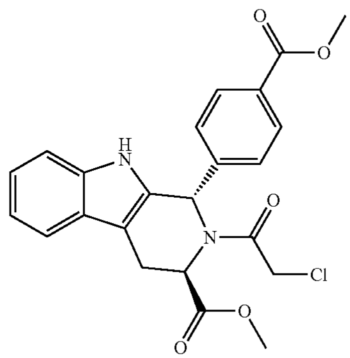 [SMILES: COC(=O)c1ccc([C@H]2c3[nH]c4ccccc4c3C[C@H](C(=O)OC)N2C(=O)CCl)cc1] | Ferroptosis inducer by GPX4 inhibition |
| altretamine | $C_9H_{18}N_6$<br>Cas: 645-05-6 | 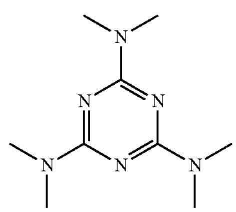 | Ferroptosis inducer by GPX4 inhibition |
| auranofin | $C_{20}H_{34}AuO_9PS$<br>Cas: 34031-32-8 | 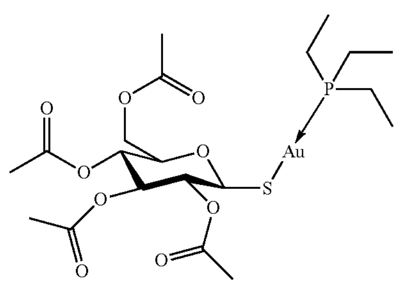 | Multiple modes of action including inhibition of thioredoxin reductase (TXNRD) |
| brusatol | $C_{26}H_{32}O_{11}$<br>Cas: 14907-98-3 | 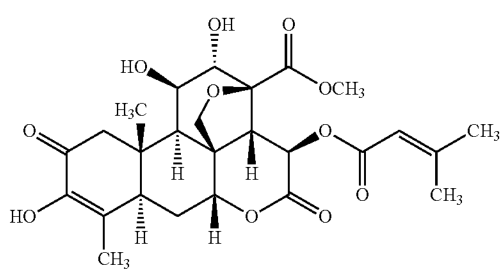 | Ferroptosis inducer by NRF2 inhibition. NRF2 is a transcriptional regulator of GPX4 protein content |
| Chlorido[N,N'-disalicylidene-1,2-phenylenediamine]iron(III) | $C_{20}H_{14}ClFeN_2O_2$<br>Cas: 39916-28-4 | 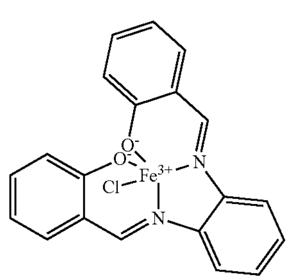 | Ferroptosis inducer by generating lipid-based reactive oxygen species (ROS) |

TABLE 1-continued

Ferroptosis-inducing agents

| Name | Formula/CAS | Structure | Target(s)/Mechanism of Action |
|---|---|---|---|
| CIL56 | $C_{23}H_{27}N_3O_5S_2$<br>Cas: 300802-28-2 | 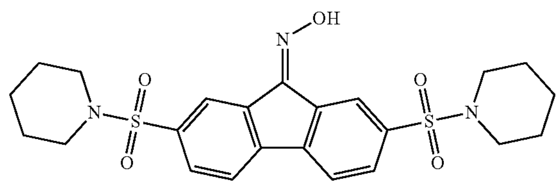 [SMILES: O=S(=O)(c1ccc2c(c1)C(=NO)c1cc(S(=O)(=O)N3CCCCC3)ccc1-2)N1CCCCC1] | Ferroptosis inducer by generating lipid-based reactive oxygen species (ROS) |
| Dihydroisotanshinone I | $C_{18}H_{14}O_3$<br>Cas: 20958-18-3 | | Ferroptosis inducer by increasing lipid peroxidation and GPX4 inhibition |
| erastin | $C_{30}H_{31}ClN_4O_4$<br>Cas: 571203-78-6 | 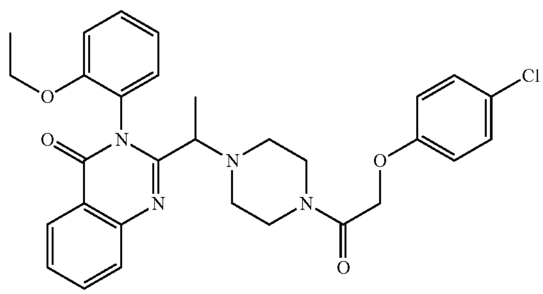 [SMILES: CCOc1ccccc1-n1c(C(C)N2CCN(C(=O)COc3ccc(Cl)cc3)CC2)nc2ccccc2c1=O] | Ferroptosis inducer by inhibition of cystine uptake by the system xc-cystine-glutamate transporter |
| Erastin-like-PE | $C_{35}H_{41}ClN_6O_4$ | 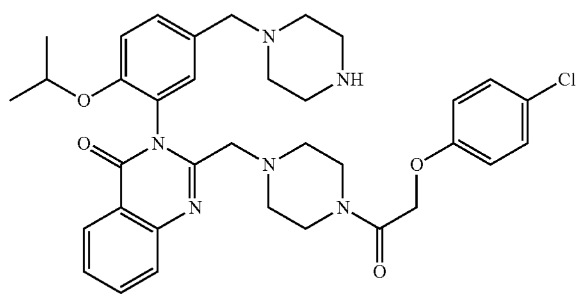 [SMILES: CC(C)Oc1ccc(CN2CCNCC2)cc1-n1c(CN2CCN(C(=O)COc3ccc(Cl)cc3)CC2)nc2ccccc2c1=O] | Ferroptosis inducer by inhibition of cystine uptake by the system xc-cystine-glutamate transporter |
| Erastin-like-IKE | $C_{35}H_{35}ClN_6O_5$ | 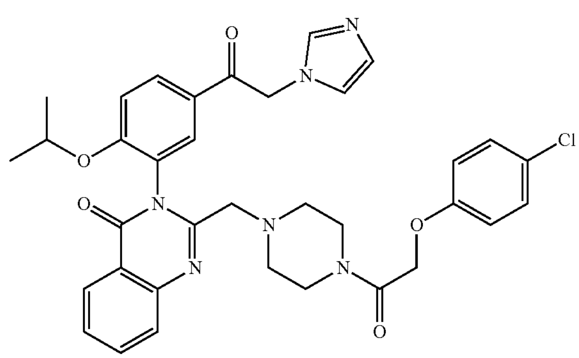 [SMILES: CC(C)Oc1ccc(C(=O)Cn2ccnc2)cc1-n1c(CN2CCN(C(=O)COc3ccc(Cl)cc3)CC2)nc2ccccc2c1=O] | Ferroptosis inducer by inhibition of cystine uptake by the system xc-cystine-glutamate transporter |

TABLE 1-continued

Ferroptosis-inducing agents

| Name | Formula/ CAS | Structure | Target(s)/ Mechanism of Action |
|---|---|---|---|
| erastin-related (Formula 1) | Formula I:, 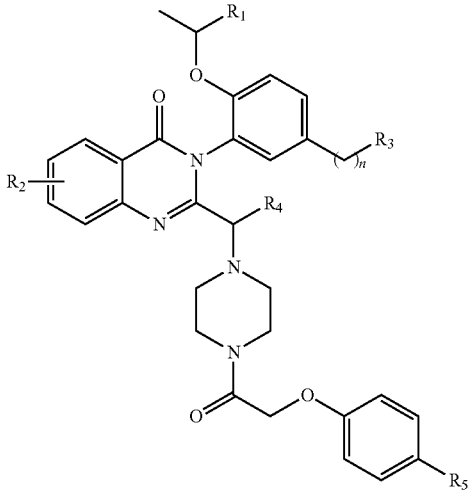 or an enantiomer, optical isomer, diastereomer, N-oxide, crystalline form, hydrate, or pharmaceutically acceptable salt thereof, wherein wherein $R_1$ is selected from the group consisting of H, $C_{1-4}$ alkyl, $C_{1-4}$ alkoxy, hydroxy, and halogen; $R_2$ is selected from the group consisting of H, halo, and Cl-4 alkyl; $R_3$ is selected from the group consisting of H, $C_{1-4}$ alkyl, $C_{1-4}$ alkoxy, 5-7 membered heterocycloalkyl, and 5-6 membered heteroaryl; $R_4$ is selected from the group consisting of H and $C_{1-4}$ alkyl; $R_5$ is halo; <br><br> is optionally substituted with = O; and n is an integer from 0-4. | | Ferroptosis inducer by inhibition of cystine uptake by the system xc-cystine-glutamate transporter |
| erastin-related (Formula II) | Formula II: 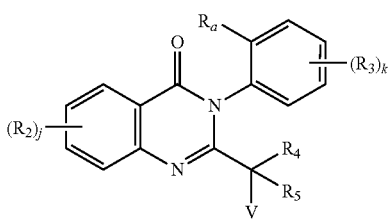 or an enantiomer, optical isomer, diastereomer, N-oxide, crystalline form, hydrate, or pharmaceutically acceptable salt thereof, wherein Ra is a halogen, substituted or unsubstituted alkyl, substituted or unsubstituted alkenyl, substituted or unsubstituted alkynyl, substituted or unsubstituted aryl-O—, substituted or unsubstituted alkyl-O—, substituted or unsubstituted alkenyl-O—or substituted or unsubstituted alkynyl-O—, where alkyl, alkenyl and alkynyl are optionally interrupted by NR, O or $S(O)_n$; each $R_2$ is independently selected from the group consisting of halogen, substituted or unsubstituted alkyl, substituted or unsubstituted aryl, substituted or unsubstituted non-aromatic heterocyclic, —CN, —COOR', —CON(R)$_2$, —NRC(O)R, —SO$_2$N(R)$_2$, —N(R)$_2$, —NO$_2$, —OH and —OR'; each $R_3$ is independently selected from | | Ferroptosis inducer by inhibition of cystine uptake by the system xc-cystine-glutamate transporter |

TABLE 1-continued

Ferroptosis-inducing agents

| Name | Formula/ CAS | Structure | Target(s)/ Mechanism of Action |
|---|---|---|---|
| | | the group consisting of halogen, substituted or unsubstituted alkyl, substituted or unsubstituted aryl, substituted or unsubstituted non-aromatic heterocyclic, —(CO)R, —CN, —COOR', —CON(R)$_2$, —NRC(O)R, —SO$_2$N(R)$_2$, —N(R)$_2$, —NO$_2$, —OH and —OR'; $R_4$ and $R_5$ are independently selected from the group consisting of —H, substituted or unsubstituted alkyl, substituted or unsubstituted alkenyl, substituted or unsubstituted alkynyl, substituted or unsubstituted non-aromatic heterocyclic and substituted or unsubstituted aryl, where alkyl, alkenyl and alkynyl are optionally interrupted by NR, O or S(O)$_n$; or $R_4$ and $R_5$ taken together form a carbocyclic or heterocyclic group; V is 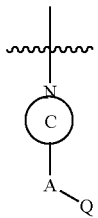 wherein Ring C is a substituted or unsubstituted heterocyclic aromatic or non-aromatic ring; A is NR or O; or A is a covalent bond; L is a substituted or unsubstituted hydrocarbyl group optionally interrupted by one or more heteroatoms selected from N, O and S; Q is selected from the group consisting of—R, —C(O)R', —C(O)N(R)2, —C(O)OR', and —S(O)2R'; each R is independently —H, alkyl, alkenyl, alkynyl, aryl, or non-aromatic heterocyclic, wherein said alkyl, alkenyl, alkynyl, aryl, or non-aromatic heterocyclic groups are substituted or unsubstituted; each R' is independently an alkyl, alkenyl, alkynyl group, non-aromatic heterocyclic or aryl group, wherein said alkyl, alkenyl, alkynyl, non-aromatic heterocyclic or aryl groups are substituted or unsubstituted; j is an integer from 0 to 4; k is an integer from 0 to 4, provided that at least one of j and k is an integer from 1 to 4; and each n is independently 0, 1 or 2. | |
| erastin-related (Formula III) | Formula III: | or an enantiomer, optical isomer, diastereomer, N-oxide, crystalline form, hydrate, or pharmaceutically acceptable salt thereof, wherein $R_1$, $R_2$, $R_3$, and $R_6$ are independently selected from H, $C_{1-8}$ alkyl, $C_{1-8}$ alkoxy, $C_{1-8}$ aralkyl, 3- to 8-membered carbocyclic, 3- to 8-membered heterocyclic, 3- to 8-membered aryl, or 3- to 8-membered heteroaryl, acyl, alkylsulfonyl, and arylsulfonyl, wherein each alkyl, alkoxy, aralkyl, carbocyclic, heterocyclic, aryl, heteroaryl, acyl, alkylsulfonyl, and arylsulfonyl is optionally substituted with at least one substituent; R4 and Rs are independently selected from H1 $C_{1-8}$ alkyl, $C_{1-8}$ alkoxy, 3- to 8-membered carbocyclic, 3- to 8-membered heterocyclic, 3- to 8-membered aryl, or 3- to 8-membered heteroaryl, carboxylate, ester, amide, | Ferroptosis inducer by inhibition of cystine uptake by the system xc-cystine-glutamate transporter |

TABLE 1-continued

Ferroptosis-inducing agents

| Name | Formula/ CAS | Structure | Target(s)/ Mechanism of Action |
|------|--------------|-----------|-------------------------------|
| | | carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether, wherein each alkyl, alkoxy, carbocyclic, heterocyclic, aryl, heteroaryl, carboxylate, ester, amide, carbohydrate, amino acid, acyl, alkoxy-substituted acyl, alditol, $NR^7R^8$, $OC(R^7)_2COOH$, $SC(R^7)_2COOH$, $NHCHR^7COOH$, $COR^8$, $CO_2R^8$, sulfate, sulfonamide, sulfoxide, sulfonate, sulfone, thioalkyl, thioester, and thioether is optionally substituted with at least one substituent; $R_7$ is selected from H, $C_{1-8}$ alkyl, carbocycle, aryl, heteroaryl, heterocycle, alkylaryl, alkylheteroaryl, and alkylheterocycle, wherein each alkyl, carbocycle, aryl, heteroaryl, heterocycle, alkylaryl, alkylheteroaryl, and alkylheterocycle may be optionally substituted with at least one substituent; $R_8$ is selected from H, $C_{1-8}$ alkyl, $C_{1-8}$ alkenyl, $C_{1-8}$ alkynyl, aryl, carbocycle, heteroaryl, heterocycle, alkylaryl, alkylheteroaryl, alkylheterocycle, and heteroaromatic, wherein each alkyl, alkenyl, alkynyl, aryl, carbocycle, heteroaryl, heterocycle, alkylaryl, alkylheteroaryl, alkylheterocycle, and heteroaromatic may be optionally substituted with at least one substituent; and X is 0-4 substituents on the ring to which it is attached. | |
| erastin-related (Formula IV) | Formula IV: | 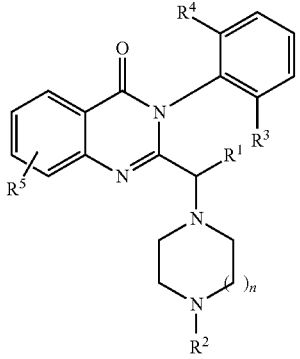

or an enantiomer, optical isomer, diastereomer, N-oxide, crystalline form, hydrate, or pharmaceutically acceptable salt thereof, wherein $R_1$ is selected from H and $C_{1-8}$ alkyl; $R_2$ is selected from H and $C_{1-8}$ alkyl; $R_3$ is selected from halogen, $C_{1-8}$ alkoxy and $C_{1-8}$ alkyl; $R_4$ is selected from H, halogen, $C_{1-8}$ alkoxy and $C_{1-8}$ alkyl; $R_5$ is selected from H, halogen and nitro; and n is 1 or 2. | Ferroptosis inducer by inhibition of cystine uptake by the system xc- cystine- glutamate transporter |

TABLE 1-continued

Ferroptosis-inducing agents

| Name | Formula/ CAS | Structure | Target(s)/ Mechanism of Action |
|---|---|---|---|
| erastin-related (Formula V) | Formula V: | 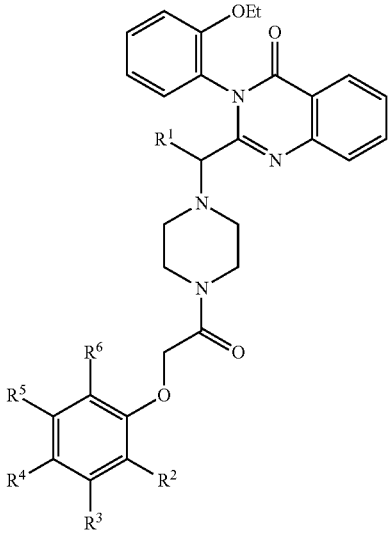 | Ferroptosis inducer by inhibition of cystine uptake by the system xc- cystine- glutamate transporter |
| erastin-like-AM | | 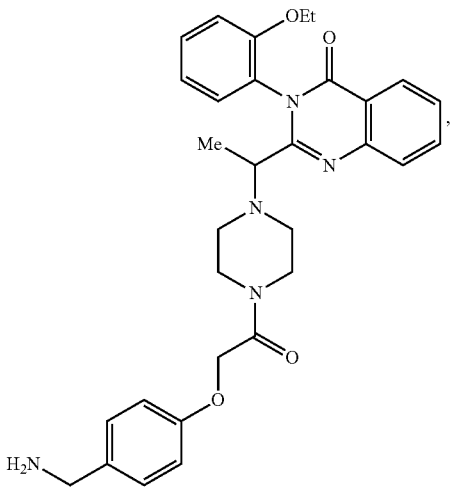 [SMILES: CCOc1ccccc1-n1c(C(C)N2CCN(C(=O)COc3ccc(CN)cc3)CC2)nc2ccccc2c1=O] | Ferroptosis inducer by inhibition of cystine uptake by the system xc- cystine- glutamate transporter | wherein, $R_1$ is selected from H, $C_{1-8}$alkyl, $C_{1-8}$ alkoxy, 3- to 8-membered carbocyclic or heterocyclic, aryl, heteroaryl, $C_{1-4}$ aralkyl, residues of glycolic acid, ethylene glycol/propylene glycol copolymers, carboxylate, ester, amide, carbohydrate, amino acid, alditol, $OC(R^7)_2COOH$, $SC(R^7)_2COOH$, $NHCHR^7COOH$, $COR^8$, $CO^2R^8$, sulfate, sulfonamide, sulfoxide, sulfonate, sulfone, thioalkyl, thioester, and thioether; $R_2$, $R_3$, $R_4$, $R_5$, and $R_6$ are independently selected from H, halo, $C_{1-4}$alkyl, $C_{1-4}$ alkylamino, acyl, and alkylsulfonyl; $R_7$ is selected from H, $C_{1-8}$alkyl, optionally substituted carbocycle, aryl, heteroaryl, heterocycle, alkylaryl, alkylheteroaryl, and alkylheterocycle; and $R_8$ is selected from optionally substituted $C_{1-8}$alkyl, $C_{1-8}$alkenyl, $C_{1-8}$alkynyl, aryl, carbocycle, heteroaryl, heterocycle, alkylaryl, alkylheteroaryl, alkylheterocycle, and heteroaromatic.

TABLE 1-continued
| | | Ferroptosis-inducing agents | | |
|---|---|---|---|---|
| Name | Formula/ CAS | Structure | | Target(s)/ Mechanism of Action |
| erastin-like-PHTL | | 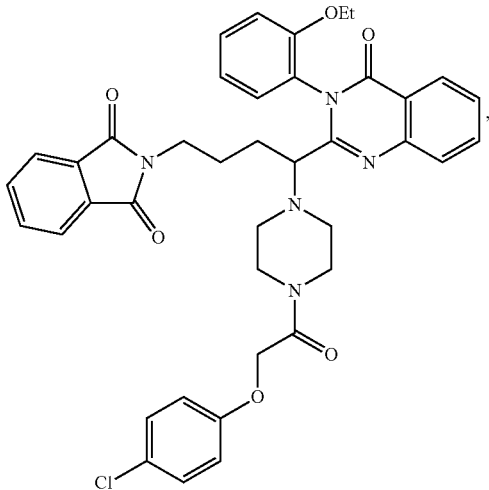 [SMILES: CCOc1ccccc1-n1c(C(CCCN2C(=O)c3ccccc3C2=O)N2CCN(C(=O)COc3ccc(Cl)cc3)CC2)nc2ccccc2c1=O] | | Ferroptosis inducer by inhibition of cystine uptake by the system xc-cystine-glutamate transporter |
| erastin-like-H2 | | 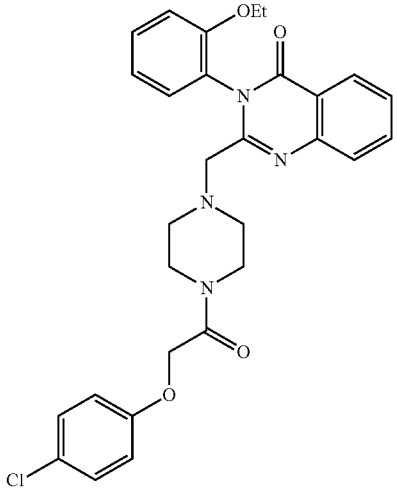 [SMILES: CCOc1ccccc1-n1c(CN2CCN(C(=O)COc3ccc(Cl)cc3)CC2)nc2ccccc2c1=O] | | Ferroptosis inducer by inhibition of cystine uptake by the system xc-cystine-glutamate transporter |

TABLE 1-continued

Ferroptosis-inducing agents

| Name | Formula/ CAS | Structure | Target(s)/ Mechanism of Action |
|---|---|---|---|
| erastin-related (Formula VI) | Formula VI: | 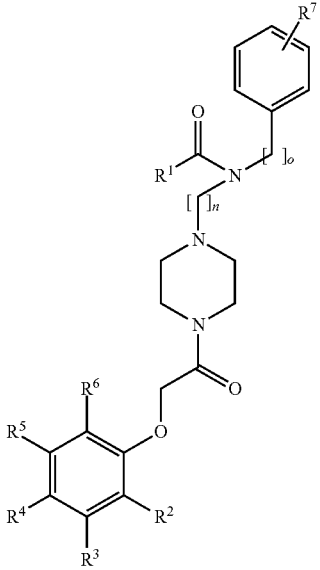 or an enantiomer, optical isomer, diastereomer, N-oxide, crystalline form, hydrate, or pharmaceutically acceptable salt thereof, wherein $R_1$ is selected from $C_{1-8}$alkyl, $C_{1-8}$alkyl-$OR^3$, 3- to 8-membered carbocyclic or heterocyclic, aryl, heteroaryl, $C_{1-4}$aralkyl, nitrogen substituted with $C_{1-6}$ alkyl, hydroxy substituted $C_{1-6}$alkyl, and $C_{1-4}$alkoxy; $R_2$, $R_3$, $R_4$, $R_5$, and $R_6$ are independently selected from H, halo, $C_{1-4}$ alkyl, $C_{1-4}$ alkylamino, acyl, and alkylsulfonyl; $R_7$ is selected from halo, $C_{1-8}$alkyl, $C_{1-8}$alkylamino. $C_{1-8}$ alkylthio, $C_{1-8}$ alkoxy, $C_{1-8}$ alkynyl, amide, amine, carbamate, carbonate, carboxy, acyl, ether, heteroalkyl, and aralkyl; and n and o are independently selected from an integer from 1 to 4. | Ferroptosis inducer by inhibition of cystine uptake by the system xc-cystine-glutamate transporter |
| erastin-related (Formula VII) | Formula VII: | 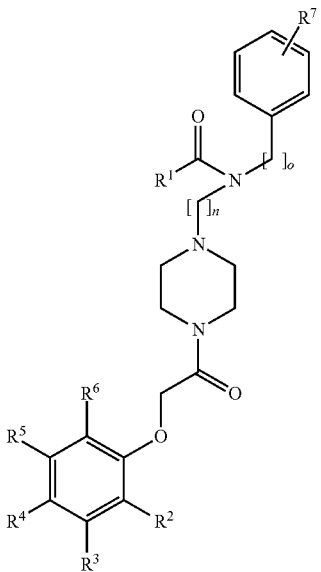 | Ferroptosis inducer by inhibition of cystine uptake by the system xc-cystine-glutamate transporter |

TABLE 1-continued

Ferroptosis-inducing agents

| Name | Formula/ CAS | Structure | Target(s)/ Mechanism of Action |
|---|---|---|---|
| | | or an enantiomer, optical isomer, diastereomer, N-oxide, crystalline form, hydrate, or pharmaceutically acceptable salt thereof, wherein $R_1$ is selected from methyl, ethyl, propyl, phenyl, and a substituted N; $R_2$, $R_3$, $R_4$, $R_5$, and $R_6$ are independently selected from H, halo, $C_{1-4}$alkyl, $C_{1-4}$ alkylamino, acyl, and alkylsulfonyl $R_7$ is F; n is 2; o is 1 | |
| RSL-like compound (Formula VIII) | | Formula VIII: [structure of fluorenone-bis-sulfonamide with $R_1$ on imine N, $R_2$, $R_2'$ on left sulfonamide N, $R_3$, $R_3'$ on right sulfonamide N] or an N-oxide, crystalline form, hydrate, or pharmaceutically acceptable salt thereof; wherein: $R_1$ is selected from the group consisting of H, OH, and $(-OCH_2CH_2)_xOH$; X is an integer from 1 to 6; and $R_2$, $R_{2'}$, $R_3$, and $R_{3'}$ independently are selected from the group consisting of H, $C_{3-8}$ cycloalkyl, and combinations thereof, or $R_2$ and $R_{2'}$ may be joined together to form a pyridinyl or pyranyl and $R_3$ and $R_{3'}$ may be joined together to form a pyridinyl or pyranyl; or an N-oxide, or pharmaceutically acceptable salt thereof. | Ferroptosis inducer by inhibition of cystine uptake by the system xc-cystine-glutamate transporter |
| RSL-like compound (Formula IX) | | Formula IX: [structure with tetrahydropyranyl/cyclohexyl groups $R_4$ and $R_5$ attached via NH-sulfonyl to fluorenone imine with $R_1$] $R_1$ is selected from the group consisting of OH and $(OCH_2CH_2)_xOH$; X is an integer from 1 to 6; and $R_4$ and $R_5$ are independently selected from the group consisting of $CH_2$ and O; or an N-oxide; or wherein: $R_1$ is OH and (1) $R_4$ and $R_5$ are both O; or (2) $R_4$ is $CH_2$ and $R_5$ is O; or (3) $R_4$ is O and $R_5$ is $CH_2$ or an N-oxide, or pharmaceutically acceptable salt thereof. | Ferroptosis inducer by GPX4 inhibition |
| RSL-like compound SRS8-18 | | [structure: fluorenone with =N-OH, bearing two sulfonamide-linked tetrahydropyranyl groups] | Ferroptosis inducer by GPX4 inhibition |

TABLE 1-continued

Ferroptosis-inducing agents

| Name | Formula/ CAS | Structure | Target(s)/ Mechanism of Action |
|---|---|---|---|
| RSL-like compound SRS11-31 | | 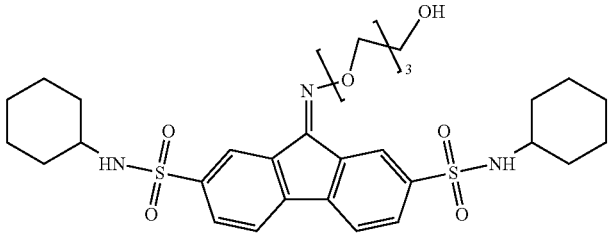 | Ferroptosis inducer by GPX4 inhibition |
| RSL-like compound SRSH-66 | | 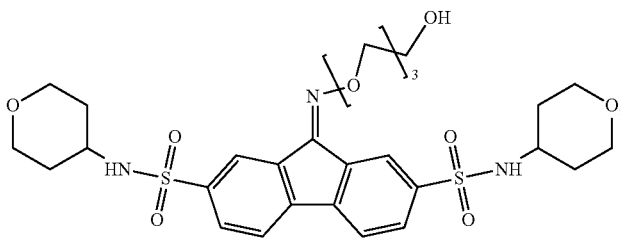 | Ferroptosis inducer by GPX4 inhibition |
| Ferroptosis inducer (Formula X) | Formula X: 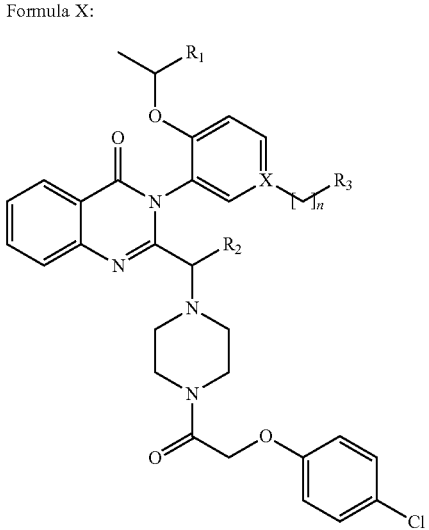 | | Ferroptosis inducer by GSH inhibition | wherein $R_1$ is selected from the group consisting of H, $C_{1-4}$ alkyl, $C_{1-4}$ alkoxy, hydroxy, and halogen; $R_2$ is selected from the group consisting of H, $C_{1-4}$ alkyl, $C_{1-4}$ alkoxy, $C_{3-8}$ cycloalkyl, $C_{3-8}$ heterocycloalkyl, aryl, heteroaryl, $C_{1-4}$ aralkyl; $R_3$ is selected from the group consisting of nothing, $C_{1-4}$ alkyl, $C_{1-4}$ alkoxy, carbonyl, $C_{3-8}$ cycloalkyl, and $C_{3-8}$ heterocycloalkyl; X is selected from the group consisting of C, N, and O; and n is an integer from 0-6, with the proviso that when X is C, n = 0, and $R_3$ is nothing, $R_1$ cannot be H when $R_2$ is $CH_3$, or an N-oxidecrystalline form, hydrate, or pharmaceutically acceptable salt thereof.

TABLE 1-continued

Ferroptosis-inducing agents

| Name | Formula/CAS | Structure | Target(s)/Mechanism of Action |
|---|---|---|---|
| Ferroptosis Inducer (Formula XI) | Formula XI: | 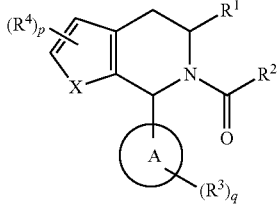<br><br>wherein: ring A is $C_4$-$C_{10}$cycloalkyl, heterocyclyl, aryl, or heteroaryl; X is —O—, —S—, —$NR_9$—, —$CR^5$=$CR^5$—, or —$CR^5$=N—; p is 0, 1 or 2; q is 0, 1, 2 or 3; $R_1$ is $C_1$-$C_3$alkyl, $C_2$-$C_6$alkenyl, $C_2$-$C_6$alkynyl, $C_1$-$C_6$haloalkyl, $C_3$-$C_{10}$cycloalkyl, —CN, —$OR^7$, —C(O)$OR^6$, —C(O)N($R^7$)$_2$, —OC(O)$R^6$, —S(O)$_2R^8$, —S(O)$_2$N($R^7$)$_2$, —S(O)N($R^7$)$_2$, —S(O)$R^8$, —N($R^7$)$_2$, —$NO_2$, —$C_1$-$C_6$alkyl—$OR^7$, or —Si($R^{15}$)$_3$; $R_2$ is —$C_1$-$C_2$haloalkyl, —$C_2$-$C_3$alkenyl, —$C_2$-$C_3$haloalkenyl, $C_2$alkynyl, or —$CH_2$OS(O)$_2$-phenyl, wherein the $C_1$-$C_2$alkylhalo and —$C_2$-$C_3$alkenylhalo are optionally substituted with one or two —$CH_3$, and the $C_2$alkynyl and phenyl are optionally substituted with one —$CH_3$; each $R_3$ is independently halo, —CN, —OH, —$OR^8$, —$NH_2$, —$NHR^8$, —N($R^8$)$_2$, —S(O)$_2R^8$, —S(O)$R^8$, —S(O)$_2$N($R^7$)$_2$, —S(O)N($R^7$)$_2$, —$NO_2$, —Si($R^{12}$)$_3$, —$SF_5$, —C(O)$OR^6$, —C(O)N($R^7$)$_2$, —$NR^{12}$C(O)$R_8$, —$NR^{12}$C(O)$OR^8$, —OC(O)N($R^7$)$_2$, —OC(O)$R^8$, —C(O)$R^6$, —OC(O)$CHR^8$N($R^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_3$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl $C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteroaryl, or —$C_2$-$C_6$alkenylheteroaryl of $R_3$ is independently optionally substituted with one to three $R_{10}$; each $R^4$ is independently halo, —CN, —OH, —$OR^8$, —NH2, —$NHR^8$, —N($R^8$)$_2$, —S(O)$_2R^8$, —S(O)$R^8$, —S(O)$_2$N($R^7$)$_2$, —S(O)N($R^7$)$_2$, —$NO_2$, —Si($R^5$)$_3$, —C(O)$OR^6$, —C(O)N($R^7$)$_2$, —$NR^{12}$C(O)$R^8$, —OC(O)R, —C(O)$R^6$, —$NR^{12}$C(O)$OR^8$, —OC(O)N($R^7$)$_2$, —OC(O)$CHR^8$N($R^{12}$)$_2$, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl of $R^4$ is optionally independently optionally substituted with one to three $R^{10}$; each $R^5$ is independently hydrogen, halo, —CN, —OH, —$OR^8$, —$NH_2$, —$NHR^8$, —N($R^8$)$_2$, —S(O)$_2R^8$, —S(O)$R^8$, —S(O)N($R^7$)$_2$, —S(O)N($R^7$)$_2$, —$NO_2$, —Si($R^5$)$_3$, —C(O)$OR^6$, —C(O)N($R^7$)$_2$, —$NR^{12}$C(O)$R^8$, —OC(O)$R^8$, —C(O)$R^6$, —$NR^{12}$C(O)$OR^8$, —OC(O)N($R^7$)$_2$, —OC(O)$CHR^8$N($R^{12}$), $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$- | Ferroptosis inducer by GPX4 inhibition |

| Name | Formula/ CAS | Structure | Target(s)/ Mechanism of Action |
|---|---|---|---|
| | | $C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, $C_1$-$C_6$alkylheteroaryl, or —$C_2$-$C_6$alkenylheteroaryl; wherein each $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenytheterocyclyl, —$C_1$-$C_6$alkylaryl, —$C_2$-$C_6$alkenylary, $C_1$-$C_6$alkylheteroaryl, or —$C_2$-$C_6$alkenylheteroaryl of R is optionally independently optionally substituted with one to three $R^{10}$; each $R^6$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, $C_2$-$C_6$alkenylheterocyclyl, —$C_1$-$C_6$alkylaryl, —$C_2$-$C_6$alkenylaryl, $C_1$-$C_6$alkytheteroaryl, or —$C_2$-$C_6$alkenylheteroaryl; wherein each $R^6$ is independently further substituted with one to three $R^{11}$; each $R^7$ is independently hydrogen, $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_6$cycloalkyl, —$C_2$-$C_6$alkenyl$C_3$-$C_6$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylatyl, —$C_1$-$C_6$alkytheteroaryl, —$C_2$-$C_6$alkenylheteroaryl, or two $R^7$ together with the nitrogen atom to which they are attached, form a 4 to 7 membered heterocyclyl; wherein each $R^7$ or ring formed thereby is independently further substituted with one to three $R^{11}$; each $R^8$ is independently $C_1$-$C_6$alkyl, $C_2$-$C_6$alkenyl, $C_2$-$C_6$alkynyl, $C_3$-$C_{10}$cycloalkyl, heterocyclyl, aryl, heteroaryl, —$C_1$-$C_6$alkyl$C_3$-$C_{10}$cycloalkyl, —$C_2$-$C_6$alkenyl$C_3$-$C_{10}$cycloalkyl, —$C_1$-$C_6$alkylheterocyclyl, —$C_2$-$C_6$alkenylheterocyclyl, —$C_1$-$C_6$alkylaryl, —$C_2$-$C_6$alkenylaryl, —$C_1$-$C_6$alkylheteraryl, or —$C_2$-$C_6$alkenylheteroaryl; wherein each $R^8$ is independently further substituted with one to three $R^{11}$; $R^9$ is hydrogen or $C_1$-$C_6$alkyl; each $R^{10}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(Q)R^{12}$, —$C(O)OR^{12}$, —$C(O)N(R^{12})_2$, —$NR^{12}C(O)R^{12}$, —$OC(O)R^{12}$, —$OC(O)R^{12}$, —$OC(O)N(R^{12})_2$, —$NR^{12}C(O)OR^{12}$, —$OC(O)CHR^{12}N(R^{12})$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl, wherein each $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl of $R^{10}$ is optionally independently substituted with one to three $R^{I1}$; each $R^{11}$ is independently halo, —CN, —$OR^{12}$, —$NO_2$, —$N(R^{12})_2$, —$S(O)R^3$, —$S(O)_2R^{13}$, —$S(O)N(R^{12})_2$, —$S(O)_2N(R^{12})_2$, —$Si(R^{12})_3$, —$C(O)R^{12}$, —$C(O)OR^{12}$, —$C(O)N(R^{12})_2$, —$NR^{12}C(O)R^{12}$, —$OC(O)R^{12}$, —$OC(O)OR^{12}$, —$OC(O)N(R^{12})_2$, —$NR^{12}C(O)OR^{12}$, —$OC(O)CHR^{12}N(R^{12})_2$, $C_1$-$C_6$alkyl, $C_1$-$C_6$haloalkyl, $C_2$-$C_6$alkenyl, $C_2$-$C_6$alkynyl, $C_3$-$C_{10}$cycloalkyl, heterocyclyl, aryl, or heteroaryl; each $R^{12}$ is independently hydrogen. $C_1$-$C_6$alkyl or $C_3$-$C_{10}$cycloalkyl; each $R^{13}$ is independently $C_1$-$C_6$alkyl or $C_3$-$C_{10}$cycloalkyl; and each $R^{13}$ is independently $C_1$-$C_6$alkyl, $C_2$-$C_6$alkenyl, aryl, heteroaryl, —$C_1$-$C_6$alkylaryl, —$C_2$-$C_6$alkenylary, —$C_1$-$C_6$alkylheteroaryl, and —$C_2$-$C_6$alkenytheteroaryl; provided that at least one of the following is true: 1) $R^1$ is other than —$C(O)OCH_3$; 2) $R^2$ is —$C_2$alkynyl optionally substituted with one $CH_3$; or | |

TABLE 1-continued

Ferroptosis-inducing agents

| Name | Formula/ CAS | Structure | Target(s)/ Mechanism of Action |
|---|---|---|---|

3) when $R^1$ is —C(O)OCH$_3$ stud $R^2$ is —CH$_2$Cl, then the moiety

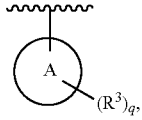

is other than 1,3-benzodioxol-5-yl, 4-nitrophenyl, 4-bromophenyl, cyclohexyl, furyl or 4-methoxyphenyl Ferroptosis Inducer (Formula XII)

Formula XII:

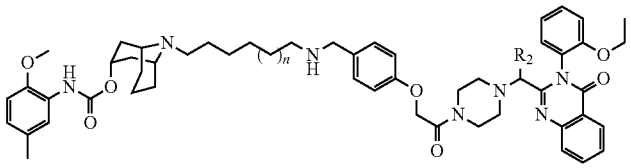

or an enanomer, optical isomer, diastereomer, N-oxide, crystalline form, hydrate, or pharmaceutically acceptable salt thereof, wherein n is an integer chosen from 1, 2, 3, 4, 5, and $R_2$ is H, or CH$_3$.

Induces ferroptosis by binding the Sigma-2 receptor and having GPX4 inhibitor activity.

Ferroptosis Inducer (Formula XIII)

Formula XIII:

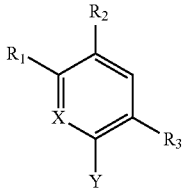

or an enantiomer, optical isomer, diastereomer, N-oxide, crystalline form, hydrate, or pharmaceutically acceptable salt thereof,
wherein X is N; Y is H, halo, or C$_{1-4}$ alkyl; $R_1$ is NR$_4$R$_5$, and at least one of R$_4$ and R$_5$ has a ring structure as defined below; $R_2$ is NR$_6$R$_7$; $R_3$ is selected from the group consisting of H,

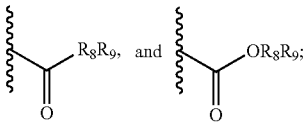

R$_4$ and R$_5$ are independently selected from the group consisting of H, C$_{1-12}$alkyl, C$_{3-12}$ cycloalkyl, and aryl, wherein one or more of the ring carbons of the cycloalkyl are optionally substituted with one or more heteroatoms, and the cycloalkyl optionally comprises one or more pendant groups selected from the group consisting of H, F, NR$_{10}$R$_{11}$, Boc, COOR$_{12}$, and C$_{1-8}$alkyl;
R$_6$ and R$_7$ are independently selected from the group consisting of H, C$_{1-6}$alkyl, Boc, O, COOR$_{12}$, Ferroptosis inducer by reducing reactive oxygen species (ROS) in a cell TABLE 1-continued Ferroptosis-inducing agents

| Name | Formula/ CAS | Structure | Target(s)/ Mechanism of Action |
|---|---|---|---|
| | | [structure: $-C(=O)-R_{12}$ fragment] and $C_{1-3}$ alkyl-aryl, wherein one or more of the ring carbprons of the alkyl-aryl are optionally substituted with one or more nitrogen atoms, and the alkyl-aryl optionally comprises one or more pendant groups selected from the group consisting of H, halo, CN, $NO_2$, $C_{1-4}$ ether, $C_{1-4}$ ester, $OCOOR_{12}$, and $C_{1-8}$ alkyl, which $C_{1-8}$ alkyl is optionally further substituted with one or more halo; $R_8$ and $R_9$ are independently selected from the group consisting of no atom, O, N, $NHR_{12}$, $C_{1-10}$ alkyl, and $C_{1-10}$ ether, wherein the alkyl and the ether are optionally substituted with $NH_2$, NHBoc, or $C_{3-12}$ cycloalkyl, wherein one or more of the ring carbons of the cycloalkyl are optionally substituted with one or more heteroatoms; $R_{10}$ and $R_{11}$ are independently selected from H and Boc; and $R_{12}$ is a $C_{1-4}$ alkyl optionally substituted with aryl. | |
| Ferroptosis Modulator X | | [structure: quinoxaline-spiropiperidine with 2-chlorobenzylamine] | Modulates ferroptosis by altering reactive oxygen species (ROS) |
| Ferroptosis Modulator Y | | [structure: quinoxaline-spiropiperidine with 3-chlorobenzylamine] | Modulates ferroptosis by altering reactive oxygen species (ROS) |
| FIN56 | $C_{25}H_{31}N_3O_5S_2$ Cas: 1083162-61-1 | [structure: fluorenone oxime bis-sulfonamide with cyclohexyl groups] | Induces ferroptosis by: (1) promoting the degradation of GPX4 and (2) reducing the abundance of CoQ10 (i.e., an antioxidant in the cell) |
| $FINO_2$ | $C_{15}H_{28}O_3$ Cas: 869298-31-7 | [structure: spirocyclic endoperoxide with tert-butyl and hydroxyethyl] | Induces ferroptosis by increasing lipid peroxidation and inhibiting GPX4 activity |
| glutamate | $C_5H_9NO_4$ Cas: 139883-82-2 | [structure: L-glutamic acid] | High extracellular glutamate concentrations prevent cystine import, causes GSH depletion increasing ferroptosis sensitivity and induction |

TABLE 1-continued

Ferroptosis-inducing agents

| Name | Formula/ CAS | Structure | Target(s)/ Mechanism of Action |
|---|---|---|---|
| GPX4-IN-3 | C$_{29}$H$_{24}$ClN$_3$O$_3$S | 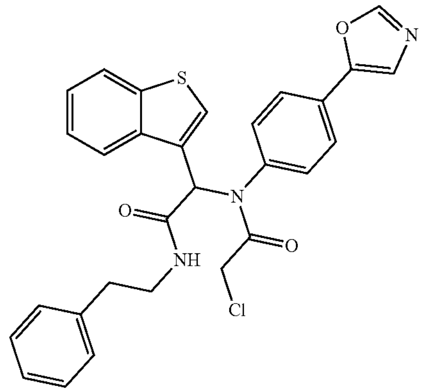 [SMILES: O=C(NCCc1ccccc1)C(c1csc2ccccc12)N(C(=O)CCl)c1ccc(-c2cnco2)cc1] | Ferroptosis inducer by GPX4 inhibition |
| jacaric acid | C$_{18}$H$_{30}$O$_2$<br>Cas: 28872-28-8 | 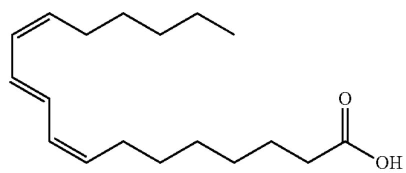 [SMILES: CCCCC\C=C/C=C/C=C\CCCCCCC(=O)O] | Induces ferroptosis by modulating the production of reactive oxygen species |
| JKE-1674 | C$_{20}$H$_{20}$Cl$_2$N$_4$O$_4$<br>Cas: 2421119-60-8 | 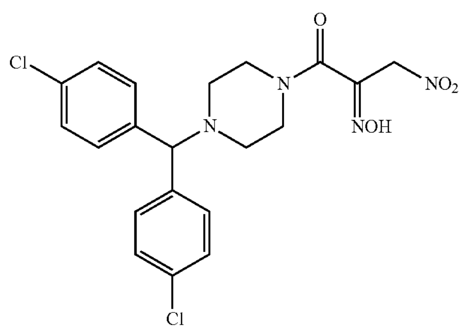 | Ferroptosis inducer by GPX4 inhibition |
| JKE-1716 | C$_{20}$H$_{20}$C$_{12}$N$_4$O$_4$<br>Cas: 2421118-05-8 | 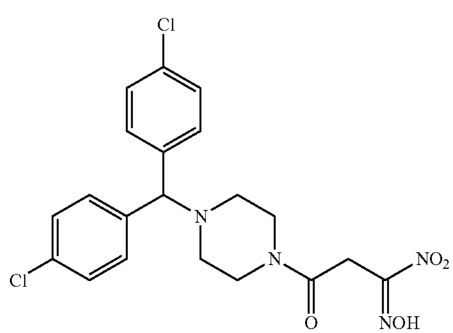 | Ferroptosis inducer by GPX4 inhibition |
| L-buthionine sulfoximine (L-BSO) | C$_8$H$_{18}$N$_2$O$_3$S<br>Cas: 83730-53-4 | 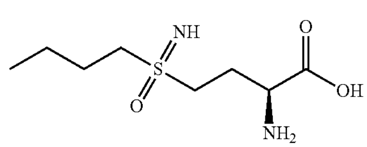 | Ferroptosis inducer by GCL and GSS inhibition |

TABLE 1-continued

Ferroptosis-inducing agents

| Name | Formula/ CAS | Structure | Target(s)/ Mechanism of Action |
| --- | --- | --- | --- |
| ML-162 | $C_{23}H_{22}Cl_2N_2O_3S$ Cas: 1035072-16-2 | [chemical structure] | Ferroptosis inducer by GPX4 inhibition |
| ML-210 | $C_{22}H_{20}Cl_2N_4O_4$ Cas: 1360705-96-9 | [chemical structure] | Ferroptosis inducer by GPX4 inhibition |
| RSL3-like (Formula XIV) | Formula XIV: [chemical structure] $R_1$ is selected from the group consisting of H, OH, and —$(OCH_2CH_2)_xOH$; X is an integer from 1 to 6; and $R_2$, $R_2'$, $R_3$, and $R_3'$ independently are selected from the group consisting of H, $C_{3-8}$ cycloalkyl, and combinations thereof, or $R_2$ and $R_2'$ may be joined together to form a pyridinyl or pyranyl and $R_3$ and $R_3'$ may be joined together to form a pyridinyl or pyranyl. | Ferroptosis inducer by GPX4 inhibition |
| RSL3-like (Formula XV) | Formula XV: [chemical structure] or an N-oxide, crystalline form, hydrate, or pharmaceutically acceptable salt thereof; wherein: n is 2, 3 or 4; and R is a substituted or unsubstituted $C_1$-$C_6$ alkyl group, a substituted or unsubstituted $C_3$-$C_{10}$ | Ferroptosis inducer by GPX4 inhibition |

TABLE 1-continued

Ferroptosis-inducing agents

| Name | Formula/CAS | Structure | Target(s)/Mechanism of Action |
|---|---|---|---|
| | | cycloalkyl group, a substituted or unsubstituted $C_2$-$C_8$ heterocycloalkyl group, a substituted or unsubstituted $C_6$-$C_{10}$ aromatic ring group, or a substituted or unsubstituted $C_3$-$C_8$ heteroaryl ring group; wherein the substitution means that one or more hydrogen atoms in each group are substituted by the following groups selected from the group consisting of: halogen, cyano, nitro, hydroxy, $C_1$-$C_6$ alkyl, halogenated $C_1$-$C_6$ alkyl, $C_1$-$C_6$ alkoxy, halogenated $C_1$-$C_6$ alkoxy, COOH (carboxy), COOC$_1$-$C_6$ alkyl, OCOC$_1$-$C_6$ alkyl. | |
| Se-Methylselenocysteine (hydrochloride) | $C_4H_9NO_2Se•HCl$ Cas: 863394-07-4 | 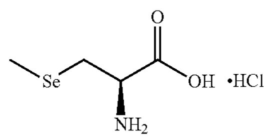 | Ferroptosis inducer by preventing increases in glutathione reductase and glutathione peroxidase (GPX) activity |
| simvastatin | $C_{25}H_{38}O_5$ Cas: 79902-63-9 | 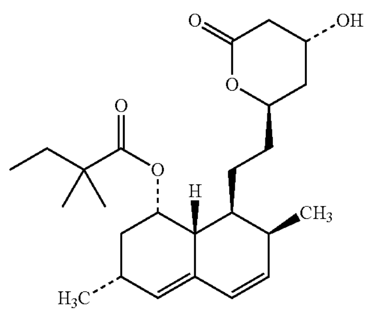 [SMILES: CCC(C)(C)C(=O)O[C@H]1C[C@@H](C)C=C2C=C[C@H](C)[C@H](CC[C@@H]3C[C@@H](O)CC(=O)O3)[C@H]21] | Ferroptosis inducer by GPX4 inhibition |
| sorafenib | $C_{21}H_{16}ClF_3N_4O_3$ Cas: 284461-73-0 | 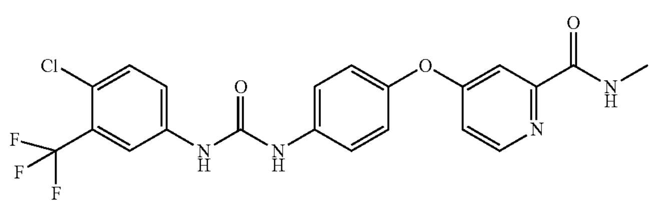 [SMILES: CNC(=O)c1cc(Oc2ccc(NC(=O)Nc3ccc(Cl)c(C(F)(F)F)c3)cc2)ccn1] | Induces ferroptosis by inhibiting multiple kinases |
| sulfasalazine | $C_{18}H_{14}N_4O_5S$ Cas: 599-79-1 | 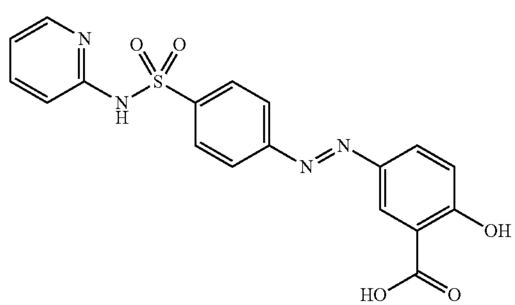 [SMILES: O=C(O)c1cc(/N=N/c2ccc(S(=O)(=O)Nc3ccccn3)cc2)ccc1O] | Ferroptosis inducer by xCT inhibition |
| trigonelline | $C_7H_8NO_2•Cl$ Cas: 6138-41-6 | 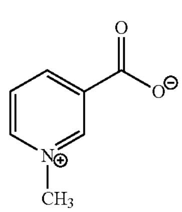 | Ferroptosis inducer by NRF2 inhibition. NRF2 is a transcriptional regulator of GPX4 protein content |

In some embodiments, the ferroptosis-inducing agent is selected from the group consisting of: (1S,3R)-RSL3, ML-162, ML-210, JKE-1674, JKE-1716, erastin, jacaric acid, buthionine sulfoximine (BSO), trigonelline, glutamate, sulfasalazine, auranofin, brusatol, sorafenib, sorafenib-d3, sorafenib tosylate, trigonelline, FIN56, $FINO_2$, CIL56, dihydroisotanshinone I, GPX4-IN-3, analogs, salts, or derivatives thereof. In some embodiments, the agent in Table 1 is a pharmaceutically acceptable salt form of the small molecule.

(2) Priming Agents

Provided herein are methods of inducing targeted cell death in a mammalian tissue in vivo, the methods comprising: (a) contacting a mammalian tissue with a priming agent; (b) contacting the mammalian tissue in vivo with an effective amount of a ferroptosis-inducing agent for a duration of time of at least 4 hours, when a plurality of cells within the mammalian tissue are responsive to the priming agent as determined by detecting in the mammalian tissue: (i) a plurality of cells comprising a concentration of selenium greater than a selenium concentration in the mammalian tissue prior to contacting with the priming agent; (ii) a plurality of cells comprising a concentration of iron greater than an iron concentration in the mammalian tissue prior to contacting with the priming agent; (iii) a plurality of cells comprising a PUFA concentration greater than a PUFA concentration in the mammalian tissue prior to contacting with the priming agent; (iv) a plurality of cells expressing one or more markers indicative of a mesenchymal state; (v) a plurality of cells comprising a peroxidizability index (PI) greater than a PI in the mammalian tissue prior to contacting with the priming agent; and/or (vi) hyperproliferation of cells in the mammalian tissue, wherein the ferroptosis-inducing agent induces targeted cell death in the mammalian tissue in vivo. In some embodiments, a priming agent is administered prior to the administration of a ferroptosis-inducing agent provided herein. In some embodiments, the priming agent is administered in vivo, in vitro, or ex vivo. A priming agent is an agent that prepares a subject or tissue for administration of a therapeutically effective dose of a ferroptosis-inducing agent provided herein. In some embodiments, the priming agent is a ferroptosis-inhibitor. In some embodiments, the priming agent renders a cell within a tissue as ferroptosis-sensitive. In some embodiments, the priming agent is a lipophilic antioxidant or radical trapping agent. In some embodiments, the priming agent is a polyunsaturated fatty acid. In some embodiments, the priming agent is an iron chelator. In some embodiments, the priming agent is a lipid peroxidation inhibitor. In some embodiments, the priming agent modulates blood oxygen levels. In some embodiments the priming agent is a hydroperoxide. In some embodiments, the priming agent is selected from the group consisting of: liproxstatin-1, ferrostatin-1, deferoxamine (DFO), iron, selenium, vitamin E, erythropoietin, a polyunsaturated fatty acid, N-acetylcysteine, pifithrin-alpha-HBr, and methylnaphthalene-4-propionate endoperoxide (MNPE). In some embodiments, the polyunsaturated fatty acid is selected from the group consisting of: hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, Timnodonic acid), heneicosapentaenoic acid (HPA), docosapentaenoic acid (DPA, Clupanodonic acid), docosahexaenoic acid (DHA, Cervonic acid), tetracosahexaenoic acid (Nisinic acid), tetracosapentaenoic acid, linoleic acid (LA), gamma-linolenic acid (GLA), eicosadienoic acid, dihomo-gamma-linolenic acid (DGLA), arachidonic acid (AA), docosadienoic acid, adrenic acid (AdA), docosapentaenoic acid (Osbond acid), tetracosatetraenoic acid, and tetracosapentaenoic acid. Non-limiting examples of priming agents are provided in Table 2.

TABLE 2

Priming Agents.

| Name | Chemical Formula/CAS | Chemical Structure | Target/Mechanism of Action |
|---|---|---|---|
| liproxstatin-1 | $C_{19}H_{21}ClN_4$<br>Cas: 950455-15-9 | 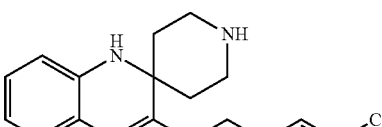 | Modulates ferroptosis by inhibiting GCL and GSS |
| ferrostatin-1 | $C_{15}H_{22}N_2O_2$<br>Cas: 347174-05-4 | 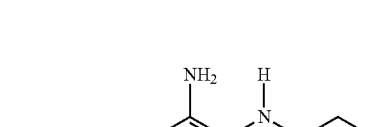 | Modulates ferroptosis by inhibiting lipid peroxidation |

TABLE 2-continued

Priming Agents.

| Name | Chemical Formula/CAS | Chemical Structure | Target/Mechanism of Action |
|---|---|---|---|
| deferoxamine mesylate (DFO) | $C_{26}H_{52}N_6O_{11}S$ Cas: 138-14-7 | •CH3SO3H | Modulates ferroptosis by chelating iron |
| iron | Fe | $Fe^{2+}$ | Modulates ferroptosis iron-dependent cell death by multiple mechanisms |
| selenium | Se | Se | Modulates ferroptosis by increasing cellular glutathione peroxidase activity and reduces susceptibility to lipid peroxidation |
| Se-Methylselenocysteine (hydrochloride) | $C_4H_9NO_2Se$•HCl Cas: 863394-07-4 | 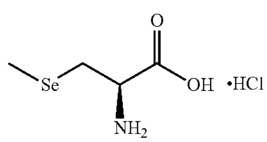 | Modulates ferroptosis by preventing increases in glutathione reductase and glutathione peroxidase (GPX) activity, as well as decreases in glutathione (GSH) levels |
| vitamin E (α-tocopherol) | $C_{31}H_{52}O_3$ Cas: 7695-91-2 | 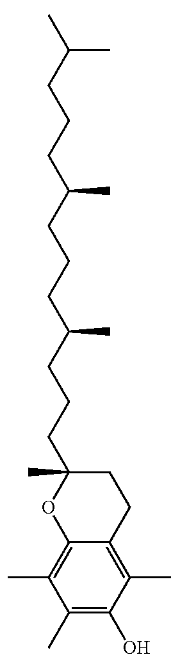 | Modulates ferroptosis by lipoxygenase inhibition |

TABLE 2-continued

Priming Agents.

| Name | Chemical Formula/CAS | Chemical Structure | Target/Mechanism of Action |
| --- | --- | --- | --- |
| α-tocotrienol | $C_{29}H_{44}O_2$ Cas: 58864-81-6 | *(chemical structure)* | Modulates ferroptosis by lipoxygenase inhibition |
| Trolox | $C_{14}H_{18}O_4$ Cas: 53188-07-1 | *(chemical structure)* | Derivative of vitamin E with potent antioxidant properties. Modulates ferroptosis by lipoxygenase inhibition |
| erythropoietin polypeptide | | erythropoietin precursor [Homo sapiens] NCBI Reference Sequence: NP 000790.2 MGVHECPAWLWLLLSLLSLPLGLPVLGAPPR LICDSRVLERYLLEAKEAENITTGCAEHCSL NEN1T VP DT KVN FYAWKRMEVGQQAVEVWQG LALLSEAVLRGQALLVNSSQPWEPLQLHVDK AVSGLRSLTTLLRALGAQKEAISPPDAASAA PLRTITADTFRKLFRVYSNFLRGKLKLYTGE ACRTGDR<br>erythropoietin [Homo sapiens] NCBI Reference Sequence: GenBank: AGW15567.1 MGVHECPAWLWLLLSLLSLPLGLPVLGAPPR LICDSRVLERYLLEAKEAENITTGCAEHCSL NENITVPDTKVNFYAWKRMEVGQQAVEVWQG LALLSEAVLRGQALLVNSSQPWEPLQLHVDK AVSGLRSLTTLLRALGAQKEAISPPDAASAA PLRTITADTFRKLFRVYSNFLRGKLKLYTGE ACRTGDRV | glycoprotein cytokine that modulates ferroptosis by increasing systemic oxygen capacity by stimulating the activity of GPX4 and inhibiting lipid peroxides |
| N-Acetylcysteine amide | $C_5H_{10}N_2O_2S$ Cas: 38520-57-9 | *(chemical structure)* | Modulates ferroptosis by inhibiting glutamate-induced cytotoxicity, decreases in intracellular glutathione (GSH) levels, and increases in intracellular reactive oxygen species (ROS) levels |

TABLE 2-continued

Priming Agents.

| Name | Chemical Formula/CAS | Chemical Structure | Target/Mechanism of Action |
|---|---|---|---|
| pifithrin-alpha-HBr | C$_{16}$H$_{18}$N$_2$OS•xHBr Cas: 63208-82-2 | 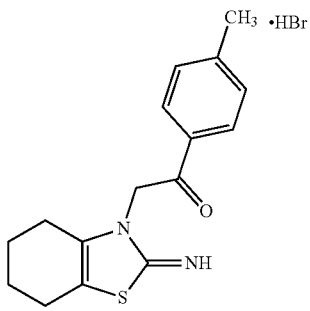 [SMILES: Cc1ccc(C(=O)Cn2c3c(sc2=N)CCCC3)cc1 ; Br] | Modulates cell death and ferroptosis by p53 inhibition |
| RC574 | C$_{18}$H$_{24}$OSSe Cas: 2584411-87-8 | 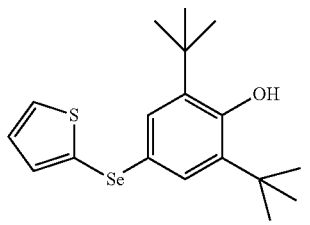 | Increase glutathione peroxidase 1 (GPX1) levels and GPX activity, inhibits ferroptosis induced by GPX4 inhibition |

In some embodiments, methods provided herein comprise administering any one of the agents listed in Table 2. Further provided herein are pharmaceutical compositions, wherein the compositions comprise a ferroptosis-inducing agent and a priming agent. In some embodiments, the pharmaceutical compositions further comprise a chemotherapeutic agent.

(3) Additional Treatments and Cell Death-Inducing Agents

In some embodiments, the methods provided herein comprise administering at least one additional treatment to a subject. In some embodiments, the additional treatment is surgery. In some embodiments, the additional treatment is radiation therapy. In some embodiments, the additional treatment is a dietary supplement. Non-limiting examples of dietary supplements include: probiotics, selenium, iron, vitamins (e.g., vitamin A, vitamin C, vitamin E), curcumin, fish oils, beta carotene, hydrogen sulfides, fatty acids, methionine, cysteine, homocysteine, taurine, cystine or di-cysteine. In some embodiments, the dietary supplement is a high-selenium nutritional supplement.

In some embodiments, the additional treatment is an additional therapeutic agent. In some embodiments, the methods provided herein comprise administering an additional agent in combination with a ferroptosis-inducing agent, an iron-dependent cell death inducing agent, and/or a priming agent provided herein. In some embodiments, the additional agent is a cell-death inducing agent. In some embodiments, the additional agent is an anti-cancer agent. In some embodiments, the anti-cancer agent is a chemotherapeutic agent. A chemotherapeutic agent or compound is any agent or compound useful in the treatment of cancer. The chemotherapeutic cancer agents that can be used in combination with ferroptosis-inducing agents or iron-dependent cell death agents provided herein include, but are not limited to, mitotic inhibitors (*vinca* alkaloids). These include vincristine, vinblastine, vindesine and Navelbine™ (vinorelbine, 5'-noranhydroblastine). In yet other cases, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein are podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that may be used in the methods and compositions disclosed herein include antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The disclosed agents provided herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/ anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the ferroptosis-inducing agents provided herein can include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; avastin; azacitidine; azetepa; azotomycin; batimastat; benzodepa; bevacizumab; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; folinic acid; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; erythrocyte gene therapy; velaresol; veramine; verdins; verteporfin; vinorelbine; vinxaltine; vitaxin; vorozole; zanoterone; zeniplatin; zilascorb; and zinostatin stimalamer. Any of the aforementioned chemotherapeutics can be administered at a clinically effective dose. A chemotherapeutic can also be administered from about day: −14, −13, −12, −11, −10, −9, −8, −7, −6, −5, −4, −3, −2, −1, 0, 1, 2, 3, 4, 5, 6, 7, 8, 9, 10, 11, 12, 13, or up to about day 14 after administration of an agent provided herein. In some cases, a subject can have a refractory cancer that is unresponsive to a chemotherapeutic.

Pharmaceutical Compositions

Provided herein are pharmaceutical compositions, wherein the pharmaceutical compositions comprise an agent selected from Table 1 or a combination of agents selected from Table 1 and/or Table 2; and a pharmaceutically acceptable excipient. In some embodiments, the pharmaceutical composition further comprises a cell death inducing agent. In some embodiments, the pharmaceutical composition further comprises a chemotherapeutic agent. In some embodiments, pharmaceutical compositions provided herein are in a suspension, optionally a homogeneous suspension. In some embodiments, pharmaceutical compositions provided herein are in an emulsion form. In some embodiments, pharmaceutical compositions provided herein comprise a salt form of any one of the agents provided herein. In some embodiments, the salt is a methanesulfonate salt.

Also provided herein is a pharmaceutical composition comprising a ferroptosis-inducing agent or an iron-dependent cell death agent provided herein. In some embodiments, agents provided herein are combined with pharmaceutically acceptable salts, excipients, and/or carriers to form a pharmaceutical composition. Pharmaceutical salts, excipients, and carriers may be chosen based on the route of administration, the location of the target issue, and the time course of delivery of the drug. A pharmaceutically acceptable carrier or excipient may include solvents, dispersion media, coatings, antibacterial and antifungal agents, isotonic and absorption delaying agents, etc., compatible with pharmaceutical administration.

In some embodiments, the pharmaceutical composition is in the form of a solid, semi-solid, liquid or gas (aerosol). Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent. Among the acceptable vehicles and solvents that may be employed are water, Ringer's solution, U.S.P., and isotonic sodium chloride solution. In addition, sterile, fixed oils are employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Exemplary carriers and excipients can include dextrose, sodium chloride, sucrose, lactose, cellulose, xylitol, sorbitol, malitol, gelatin, polymers, polyethylene glycol (PEG), polyvinylpyrrolidone (PVP), and any combination thereof. In some embodiments, an excipient such as dextrose or sodium chloride can be at a percent from about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or up to about 15%.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable carriers and additives, for example, suspending agents, e.g., sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Formulations suitable for buccal (sublingual) administration include, for example, lozenges containing the active compound in a flavored base, usually sucrose and acacia or tragacanth; and pastilles containing the compound in an inert base such as gelatin and glycerin or sucrose and acacia.

Ferroptosis-inducing agents provided herein can be formulated as a rectal composition, for example, suppositories or retention enemas, for example, containing conventional suppository bases, for example, cocoa butter or other glycerides, or gel forming agents, such as carbomers.

Pharmaceutical compositions also can be administered by controlled release formulations and/or delivery devices (see, e.g., in U.S. Pat. No. 5,733,566).

Various delivery vehicles are known and can be used to administer ferroptosis-inducing agents provided herein, such as but not limited to, encapsulation in liposomes, microparticles, microcapsules, nanoparticles, vectors, and recombinant cells. Liposomes and/or nanoparticles also can be employed with administration of compositions herein. Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 angstroms containing an aqueous solution in the core.

Phospholipids can form a variety of structures other than liposomes when dispersed in water, depending on the molar ratio of lipid to water. At low ratios, the liposomes form. Physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one can operate at the same time. Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles can also be used as a delivery vehicle.

Nanoparticle carriers that specifically target a tissue provided herein may also be used as a pharmaceutically acceptable carrier. In some embodiments, the nanoparticle is a gold nanoparticle, a platinum nanoparticle, an iron-oxide nanoparticle, a lipid nanoparticle, a selenium nanoparticle, a tumor-targeting glycol chitosan nanoparticle (CNP), a cathepsin B sensitive nanoparticle, a hyaluronic acid nanoparticle, a paramagnetic nanoparticle, or a polymeric nanoparticle.

Suitable pharmaceutical formulations of ferroptosis-inducing agents for transdermal application include an effective amount of an agent with a carrier. Carriers include absorbable pharmacologically acceptable solvents to assist passage through the skin of the subject. For example, transdermal devices are in the form of a bandage or patch comprising a backing member, a reservoir containing the compound optionally with carriers, optionally a rate controlling barrier to deliver the compound to the skin of the host at a controlled and predetermined rate over a prolonged period of time, and a means to secure the device to the skin. Matrix transdermal formulations may also be used. Suitable formulations for topical application, e.g., to the skin and eyes, are preferably aqueous solutions, ointments, creams or gels well-known in the art. The formulations may contain solubilizers, stabilizers, tonicity enhancing agents, buffers and preservatives.

In certain embodiments, ferroptosis-inducing agents provided herein are formulated as a depot composition. Such long-acting formulations can be administered by implantation (for example, subcutaneously or intramuscularly) or by intramuscular injection. The ferroptosis-inducing agents can be formulated with suitable polymeric or hydrophobic materials (for example as an emulsion in an acceptable oil), ion exchange resins, biodegradable polymers, or as sparingly soluble derivatives, for example, as a sparingly soluble salt.

In some embodiments, one or more agent provided herein is formulated as a pharmaceutical food composition (also referred to as a medical food). The food composition can be for consumption by a mammal, for example by a human or a non-human mammal. Agents provided herein can be formulated as a dietary supplement or a medical food. In some embodiments, agents provided herein are administered with a food ingredient. A food ingredient is any product, composition, or a component of a food known to have or disclosed as having a nutritional effect. Food can include various meats (e.g., beef, pork, poultry, fish, etc.), dairy products (e.g., milk, cheese, eggs), fruits, vegetables, cereals, breads, etc., and components thereof. Food can be fresh or preserved, e.g., by canning, dehydration, freezing, or smoking. Food can be provided in raw, unprepared and/or natural states or in cooked, prepared, and/or combined states. In some embodiments, the food ingredient is selected from the group consisting of: fat, carbohydrates, protein, fiber, nutritional balancing agent, and mixtures thereof. In some embodiments, the pharmaceutical food composition provided herein further comprises one or more of a protein or an amino acid. In some embodiments of any of the aspects, the pharmaceutical food composition further comprises adenine, one or more vitamins (e.g., vitamin E), potassium, fatty acids, and/or calcium carbonate.

Methods of Administering an Agent

Provided herein can be methods for administering a therapeutic regime to a subject having a disease or disorder (e.g., cancer, an autoimmune disease, or fibrosis). In some embodiments, the administering is sustained administration of a therapeutically effective amount of a ferroptosis-inducing agent. In some embodiments, the sustained administration of the ferroptosis-inducing agent comprises providing to a tissue the ferroptosis-inducing agent in an amount sufficient to achieve a distribution of at least about 10 ng/mm$^2$ within said tissue for a period of at least 4 hours, thereby inducing ferroptosis in the tissue. In some embodiments, the sustained administration further forms a gradient of a subtherapeutic amount of the ferroptosis-inducing agent adjacent to an administration site within the tissue. In some embodiments, sustained administration of the ferroptosis-inducing agent comprises additional administration steps. In some embodiments, the ferroptosis-inducing agent is administered more than once. In some embodiments, the administering is via a system provided herein. In some embodiments, the administering local administration within a tissue. In some embodiments, the tissue is contacted in vivo with an effective amount of an iron-dependent cell death agent for a duration of time of at least 4 hours. In some embodiments, the administering comprises contacting a mammalian tissue with a priming agent and contacting the mammalian tissue with an effective amount of a ferroptosis-inducing agent provided herein, wherein the ferroptosis-inducing agent induces targeted cell death in the mammalian tissue in vivo. In some embodiments, the administering is local administration or systemic administration. In some embodiments, the administering or contacting step is via intratumoral injection, oral administration, transdermal injection, inhalation, nasal administration, topical administration, vaginal administration, ophthalmic administration, intracerebral administration, rectal administration.

In some instances, an agent or combination of agents provided herein are administered as a unit dosage form. Many agents can be administered orally as liquids, capsules, tablets, or chewable tablets. Because the oral route is the most convenient and usually the safest and least expensive, it is the one most often used. However, it has limitations because of the way a drug typically moves through the digestive tract. For agents administered orally, absorption may begin in the mouth and stomach. However, most agents are usually absorbed from the small intestine. The drug passes through the intestinal wall and travels to the liver before being transported via the bloodstream to its target site. The intestinal wall and liver chemically alter (metabolize) many agents, decreasing the amount of drug reaching the bloodstream. Consequently, these agents are often given in smaller doses when injected intravenously to produce the same effect.

In some embodiments, an agent provided herein is formulated for oral administration. In some embodiments, an agent provided herein is formulated for administration/for use in administration via a subcutaneous, intradermal, intramuscular, inhalation, intravenous, intraperitoneal, intracranial, intrathecal, intratumoral, or oral route. For a subcutaneous route, a needle is inserted into fatty tissue just beneath the skin. After a drug is injected, it then moves into small blood vessels (capillaries) and is carried away by the bloodstream. Alternatively, a drug reaches the bloodstream through the lymphatic vessels. The intramuscular route is preferred to the subcutaneous route when larger volumes of a drug product are needed. Because the muscles lie below the skin and fatty tissues, a longer needle is used. Agents are usually injected into the muscle of the upper arm, thigh, or buttock. How quickly the drug is absorbed into the bloodstream depends, in part, on the blood supply to the muscle: The sparser the blood supply, the longer it takes for the drug to be absorbed. For the intravenous route, a needle is inserted directly into a vein. A solution containing the drug may be given in a single dose or by continuous infusion. For infusion, the solution is moved by gravity (from a collapsible plastic bag) or, more commonly, by an infusion pump through thin flexible tubing to a tube (catheter) inserted in a vein, usually in the forearm. In some cases, agents or therapeutic regimes are administered as infusions. An infusion can take place over a period of time. For example, an infusion can be an administration of an agent or therapeutic regime over a period of about 5 minutes to about 5 hours. An infusion can take place over a period of about 5 min, 10 min, 20 min, 30 min, 40 min, 50 min, 1 hour, 1.5 hours, 2 hours, 2.5 hours, 3 hours, 3.5 hours, 4 hours, 4.5 hours, or up to about 5 hours.

In some embodiments, intravenous administration is used to deliver a precise dose quickly and in a well-controlled manner throughout the body. It is also used for irritating solutions, which would cause pain and damage tissues if given by subcutaneous or intramuscular injection. An intravenous injection can be more difficult to administer than a subcutaneous or intramuscular injection because inserting a needle or catheter into a vein may be difficult, especially if the person is obese. When given intravenously, a drug is delivered immediately to the bloodstream and tends to take effect more quickly than when given by any other route.

Consequently, health care practitioners closely monitor people who receive an intravenous injection for signs that the drug is working or is causing undesired side effects. Also, the effect of a drug given by this route tends to last for a shorter time. Therefore, some agents must be given by continuous infusion to keep their effect constant. For the intrathecal route, a needle is inserted between two vertebrae in the lower spine and into the space around the spinal cord. The drug is then injected into the spinal canal. A small amount of local anesthetic is often used to numb the injection site. This route is used when a drug is needed to produce rapid or local effects on the brain, spinal cord, or the layers of tissue covering them (meninges)—for example, to treat infections of these structures.

For administration by inhalation, the ferroptosis-inducing agent provided herein can be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. Agents administered by inhalation through the mouth can be atomized into smaller droplets than those administered by the nasal route, so that the agents can pass through the windpipe (trachea) and into the lungs. How deeply into the lungs the agents go depends on the size of the droplets. Smaller droplets go deeper, which increases the amount of drug absorbed. Inside the lungs, they are absorbed into the bloodstream.

Agents applied to the skin are usually used for their local effects and thus are most commonly used to treat superficial skin disorders, such as psoriasis, eczema, skin infections (viral, bacterial, and fungal), itching, and dry skin. The drug is mixed with inactive substances. Depending on the consistency of the inactive substances, the formulation may be an ointment, cream, lotion, solution, powder, or gel.

In some cases, a treatment regime may be dosed according to a body weight of a subject. In subjects who are determined obese (BMI>35) a practical weight may need to be utilized. BMI is calculated by: BMI=weight (kg)/[height (m)]$^2$.

In some cases, a therapeutic regime can be administered along with a carrier or excipient. Ferroptosis-inducing agents provided herein can be administered with one or more of a second agent, sequentially, or concurrently, either by the same route or by different routes of administration. When administered sequentially, the time between administrations is selected to benefit, among others, the therapeutic efficacy and/or safety of the combination treatment. In certain embodiments, the agents provided herein can be administered first followed by a second agent, or alternatively, the second agent is administered first followed by the agents of the present disclosure (e.g., ferroptosis-inducing agents of Table 1). By way of example and not limitation, the time between administrations is about 1 hr, about 2 hr, about 4 hr, about 6 hr, about 12 hr, about 16 hr or about 20 hr. In certain embodiments, the time between administrations is about 1, about 2, about 3, about 4, about 5, about 6, or about 7 more days. In some embodiments, the time between administrations is about 1 week, 2 weeks, 3 weeks, or 4 weeks or more. In some embodiments, the time between administrations is about 1 month or 2 months or more.

In some embodiments, ferroptosis-inducing agents provided herein contact the mammalian tissue for at least about 4 hours, at least about 6 hours, at least about 10 hours, at least about 12 hours, at least about 14 hours, at least about 16 hours, at least about 18 hours, at least about 20 hours, at least about 22 hours, at least about 24 hours, at least about 26 hours, at least about 28 hours, at least about 30 hours, at least about 36 hours, at least about 48 hours, up to 72 hours. In some embodiments, ferroptosis-inducing agents provided herein contact the mammalian tissue for about 4 hours. In some embodiments, ferroptosis-inducing agents provided herein contact the mammalian tissue for about 6 hours. In some embodiments, ferroptosis-inducing agents provided herein contact the mammalian tissue for about 10 hours. In some embodiments, ferroptosis-inducing agents provided herein contact the mammalian tissue for about 12 hours. In some embodiments, ferroptosis-inducing agents provided herein contact the mammalian tissue for about 24 hours. In some embodiments, ferroptosis-inducing agents provided herein contact the mammalian tissue for about 48 hours. In some embodiments, ferroptosis-inducing agents provided herein contact the mammalian tissue for about 72 hours.

When administered concurrently, the agent can be administered separately, at the same time as the second agent, by the same or different routes, or administered in a single pharmaceutical composition by the same route. In certain embodiments, the amount and frequency of administration of the second agent can used standard dosages and standard administration frequencies used for the particular compound.

Dosing and Tissue Distribution

The methods provided herein comprise administering to a subject an agent or pharmaceutical composition provided herein in an amount effective to induce ferroptosis in a tissue in vivo. Agents and pharmaceutical compositions for administering to a subject in need thereof may be formulated in dosage unit form for ease of administration and uniformity of dosage. A dosage unit form is a physically discrete unit of a composition provided herein appropriate for a subject to be treated. It will be understood, however, that the total usage of compositions provided herein will be decided by the attending physician within the scope of sound medical judgment. For any composition provided herein the therapeutically effective dose can be estimated initially either in cell culture assays or in animal models, such as mice, rabbits, dogs, pigs, or non-human primates. The animal model may also be used to achieve a desirable concentration range and route of administration. Such information can then be used to determine useful doses and routes for administration in humans. Therapeutic efficacy and toxicity of compositions provided herein can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies may be used in formulating a range of dosage for human use.

A typical human dose of an agent provided herein (e.g., a ferroptosis-inducing agent) may be from about 10 μg/kg body weight/day to 10,000 mg/kg/day. In some embodiments, the dose of an agent provided herein is from about 0.1 mg/kg to about 1000 mg/kg, from 1 mg/kg to 1000 mg/kg, 1 mg/kg to 800 mg/kg, from about 1 mg/kg to about 700 mg/kg, from about 2 mg/kg to about 500 mg/kg, from about 3 mg/kg to about 400 mg/kg, 4 mg/kg to about 300 mg/kg, or from about 5 mg/kg to about 200 mg/kg. In certain embodiments, the suitable dosages of the agent can be about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 2,000 mg/kg, 3,000 mg/kg, 4,000 mg/kg, 5,000 mg/kg, 6,000 mg/kg, 7,000/mg/kg, 8,000 mg/kg, 9,000 mg/kg, up to 9,600 mg/kg. In some embodiments, the dose of an agent provided herein is from about 100 mg/kg/day to about 6,400 mg/kg/day four times per day. In some embodiments, the dose of an agent provided herein is from about 50 mg/kg/day to about 25 mg/kg/day. In some embodiments, the dose of an agent provided herein is from about 400 mg/kg/day to about 800 mg/kg/day. In certain embodiments, the dose of the agent can be administered once per day or divided into subdoses and administered in multiple doses, e.g., twice, three times, or four times per day.

In some embodiments, agents provided herein are administered in an amount of at least about 10 nanograms (ng) or more, about 20 ng or more, about 30 ng or more, about 40 ng or more, about 50 ng or more, about 60 ng or more, about 70 ng or more, about 80 ng or more, about 90 ng or more, up to 100 ng. In some embodiments, the agent is administered in an amount of at least about 1 microgram (µg) or more, about 5 µg or more, about 10 µg or more, about 20 µg or more, about 30 µg or more, about 40 µg or more, about 50 µg or more, about 60 µg or more, about 70 or more, about 80 µg or more, about 90 µg or more, up to 100 µg.

In some embodiments, agents provided herein are administered at a concentration of at least about 0.1 micromolar (04) or more, about 1 µM or more, about 2 µM or more, about 3 µM or more, about 4 µM or more, about 5 µM or more, about 6 µM or more, about 7 µM or more, about 8 µM or more, about 9 µM or more, about 10 µM or more, about 15 µM or more, about 20 µM or more, about 25 µM or more, about 30 µM or more, about 35 µM or more, about 40 µM or more, about 45 µM or more, about 50 µM or more, about 55 µM or more, about 60 µM or more, about 65 µM or more, about 70 µM or more, about 75 µM or more, about 80 µM or more, about 85 µM or more, about 90 µM or more, about 95 µM or more, about 100 µM or more, about 110 µM or more, about 120 µM or more, about 130 µM or more, about 140 µM or more, about 150 µM or more, about 160 µM or more, about 170 µM or more, about 180 µM or more, about 190 µM or more, about 200 µM or more, about 300 µM or more, about 400 µM or more, about 500 µM or more, up to 1 mM. In some embodiments, agents provided herein are administered at a concentration of at least about 0.1 µM up to about 500 µM. In some embodiments, agents provided herein are administered at a concentration of at least about 1 µM up to 500 µM. In some embodiments, agents provided herein are administered at a concentration of at least about 0.1 µM up to 10 µM. In some embodiments, agents provided herein are administered at a concentration of at least about 1 µM up to 10 µM.

In some embodiments, ferroptosis-inducing agents provided herein are administered intravenously. In some embodiments, ferroptosis-inducing agents provided herein are administered intravenously at a concentration of at least about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, about 1000 mg/kg, about 1100 mg/kg, about 1200 mg/kg, about 1300 mg/kg, about 1400 mg/kg, about 1500 mg/kg, about 2000 mg/kg, about 2200 mg/kg, about 2400 mg/kg, up to about 2500 mg/kg. In some embodiments, ferroptosis-inducing agents provided herein are administered intravenously at a concentration of about 25 mg/kg once per day. In some embodiments, ferroptosis-inducing agents provided herein are administered intravenously at a concentration of about 25 mg/kg twice per day. In some embodiments, ferroptosis-inducing agents provided herein are administered intravenously at a concentration of about 450 mg/kg/day. In some embodiments, ferroptosis-inducing agents provided herein are administered intravenously at a concentration of about 650 mg/kg/day. In some embodiments, ferroptosis-inducing agents provided herein are administered intravenously at a concentration of about 650 mg/kg/day for 3 continuous days. In some embodiments, ferroptosis-inducing agents provided herein are administered intravenously at a concentration of about 1300 mg/kg/day. In some embodiments, ferroptosis-inducing agents provided herein are administered intravenously at a concentration of about 2400 mg/kg/day.

In some embodiments, ferroptosis-inducing agents provided herein are administered orally. In some embodiments, ferroptosis-inducing agents provided herein are administered orally at a concentration of at least about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, about 1000 mg/kg, about 1100 mg/kg, about 1200 mg/kg, about 1300 mg/kg, about 1400 mg/kg, about 1500 mg/kg, about 2000 mg/kg, about 2200 mg/kg, about 2400 mg/kg, up to about 2500 mg/kg. In some embodiments, ferroptosis-inducing agents provided herein are administered orally at a concentration of about 25 mg/kg once per day. In some embodiments, ferroptosis-inducing agents provided herein are administered orally at a concentration of about 25 mg/kg twice per day. In some embodiments, ferroptosis-inducing agents provided herein are administered orally at a concentration of about 1300 mg/kg/day. In some embodiments, ferroptosis-inducing agents provided herein are administered orally at a concentration of about 2400 mg/kg/day.

The methods provided herein can be characterized by or further comprise measuring the distribution of an agent in a target tissue. Distribution of an agent provided herein can be determined by the amount or concentration of the agent within a square millimeter ($mm^2$) or cubic millimeter ($mm^3$) of tissue. For example, for local administration of an agent to a tumor, the tissue may be from about 6 to 7 mm in diameter, 36 to 42 $mm^2$, or 216 to 294 $mm^3$. The data obtained from animal studies may be used in formulating a range of drug distribution in a mammalian tissue. Methods of determining tissue distribution of a drug or agent include, for example, mass spectrometry, chromatography, imaging techniques, and immunoassays. The distribution of an agent provided herein can be determined using a system provided herein.

In some embodiments, the tissue is administered a therapeutic amount of a ferroptosis-inducing agent, wherein administration of comprises providing to a tissue the ferroptosis-inducing agent in an amount sufficient to achieve a desired drug distribution. In some embodiments, agents provided herein achieve a distribution within a tissue of at least about 1 $ng/mm^2$ or more, about 5 $ng/mm^2$ or more, about 10 $ng/mm^2$ or more, about 15 $ng/mm^2$ or more, about 20 $ng/mm^2$ or more, about 25 $ng/mm^2$ or more, about 30 $ng/mm^2$ or more, about 35 $ng/mm^2$ or more, about 40 $ng/mm^2$ or more, about 45 $ng/mm^2$ or more, about 50 $ng/mm^2$ or more, about 55 $ng/mm^2$ or more, about 60 $ng/mm^2$ or more, about 65 $ng/mm^2$ or more, about 70 $ng/mm^2$ or more, about 75 $ng/mm^2$ or more, about 80 $ng/mm^2$ or more, about 85 $ng/mm^2$ or more, about 90 $ng/mm^2$ or more, about 95 $ng/mm^2$ or more, about 100 $ng/mm^2$ or more, about 110 $ng/mm^2$ or more, about 120 $ng/mm^2$ or more, about 130 $ng/mm^2$ or more, about 140 $ng/mm^2$ or more, about 150 $ng/mm^2$ or more, about 160 $ng/mm^2$ or more, about 170 $ng/mm^2$ or more, about 180 $ng/mm^2$ or more, about 190 $ng/mm^2$ or more, about 200 $ng/mm^2$ or more, about 300 $ng/mm^2$ or more, about 400 $ng/mm^2$ or more, up to 500 $ng/mm^2$. In some embodiments, agents provided herein achieve a distribution within a tissue of at least about 1 $ng/mm^3$ or more, about 5 $ng/mm^3$ or more, about 10 $ng/mm^3$ or more, about 15 $ng/mm^3$ or more, about 20 $ng/mm^3$ or more, about 25 $ng/mm^3$ or more, about 30 $ng/mm^3$ or more, about 35 $ng/mm^3$ or more, about 40 $ng/mm^3$ or more, about 45 $ng/mm^3$ or more, about 50 $ng/mm^3$ or more, about 55 $ng/mm^3$ or more, about 60 $ng/mm^3$ or more, about 65 $ng/mm^3$ or more, about 70 $ng/mm^3$ or more, about 75 $ng/mm^3$ or more, about 80 $ng/mm^3$ or more, about 85 $ng/mm^3$ or more, about 90 $ng/mm^3$ or more, about 95 $ng/mm^3$ or more, about 100 $ng/mm^3$ or more, about 110 $ng/mm^3$ or more, about 120 $ng/mm^3$ or more, about 130 $ng/mm^3$ or more, about 140 $ng/mm^3$ or more, about 150 $ng/mm^3$ or more, about 160 $ng/mm^3$ or more, about 170 $ng/mm^3$ or more, about 180 $ng/mm^3$ or more, about 190 $ng/mm^3$ or more, about 200 $ng/mm^3$ or more, about 300 $ng/mm^3$ or more, about 400 $ng/mm^3$ or more, up to 500 $ng/mm^3$.

In some embodiments, ferroptosis-inducing agents provided herein are administered at least about once per day, twice per day, three times per day, four times per day, or five times per day. In some embodiments of any of the aspects, ferroptosis-inducing agents are administered at least about every week, at least about every 2 weeks, or at least about every 3 weeks. The amount of drug administered depends on the size of the tissue, the type of disease being treated, and the type of administration (e.g., local administration to a tissue in vivo using a system provided herein). Effective doses will vary, depending on the types of diseases treated, route of administration, excipient usage, and the possibility of co-usage with other therapeutic treatments.

Efficacy

Therapeutic efficacy of an agent and/or pharmaceutical composition provided herein may be determined by evaluating and comparing patient symptoms and quality of life pre- and post-administration. Such methods apply irrespective of the mode of administration. In some embodiments, pre-administration refers to evaluating patient symptoms and quality of life prior to onset of therapy and post-administration refers to evaluating patient symptoms and quality of life at least 1, 2, 3, 4, 5, 6, 7, 8, 9, 10, 11, 12, 13, 14, 15, 16, 17, 18, 19, 20 weeks after onset of therapy. In a particular embodiment, the post-administration evaluating is performed about 2-8, 2-6, 4-6, or 4 weeks after onset of therapy. In a particular embodiment, patient symptoms (e.g., symptoms related to cancer, fibrosis, or autoimmune disease) and quality of life pre- and post-administration are evaluated clinically and by questionnaire assessment.

The agents and methods provided herein can be used to reduce cancer cell proliferation or survival in vivo or in vitro. Methods of evaluating tumor progression or cell proliferation are known in the art. In some embodiments, overall response is assessed from time-point response assessments (based on tumor burden) as follows:

Complete Response (CR): Disappearance of all target lesions. Any pathological lymph nodes (whether target or non-target) must have reduction in short axis to <10 mm.

Partial Response (PR): At least a 30% decrease in the sum of diameters of target lesions, taking as reference the baseline sum diameters.

Progressive Disease (PD): At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression).

Stable Disease (SD): Neither sufficient shrinkage to qualify for PR nor sufficient increase to qualify for PD, taking as reference the smallest sum diameters while on study.

In some embodiments, an in vitro cell proliferation assay is used to assess the efficacy of a one or more ferroptosis-inducing agents provided herein. The compositions and methods provided herein result in a reduction in the proliferation or survival of a plurality of cells. For example, after treatment with one or more of the agents provided herein, cell proliferation or survival is reduced by 5% or greater (e.g., 10%, 20%, 30%, 40%, 50%, 60%, 70%, 80%, 90% or greater) relative to cell proliferation or survival prior to treatment.

In some embodiments, animal models are used to assess the efficacy of a one or more ferroptosis-inducing agents provided herein in vivo. The ferroptosis-inducing agents and methods provided herein can result in a reduction in size or volume of a hyperproliferating tissue (e.g., a tumor). For example, after treatment, tissue size is reduced by 5% or greater (e.g., 10%, 20%, 30%, 40%, 50%, 60%, 70%, 80%, 90% or greater) relative to its size prior to treatment. Size of a tissue (e.g., a tumor) may be measured by any reproducible means of measurement. The size of a tissue may be measured as a diameter of the tumor or by any reproducible means of measurement. Ferroptosis inhibitors (e.g., an agent in Table 2) may be used to determine the efficacy of a particular test agent (also referred to herein as an active agent) for inducing ferroptosis in a tissue. For example, the combination of a ferroptosis inducer paired with a ferroptosis inhibitor (e.g., liproxstatin-1) can be used to determine whether the test agent targets a protein or nucleic acid involved in the ferroptosis pathway (see FIG. 1). Further provided herein is a method of rescuing a cell or plurality of cells from cell death and/or ferroptosis in vivo, the method comprising: administering to a subject a ferroptosis inhibitor. In some embodiments, the method further comprises administering a ferroptosis-inducing agent. Further provided herein is a method of screening a plurality of cells in a tissue for ferroptosis-sensitivity, the method comprising: contacting the tissue with a ferroptosis-inducing agent and a ferroptosis inhibitor; and measuring one or more parameters indicative of ferroptosis. In some embodiments, the ferroptosis-inducing agent is an agent in Table 1 or a test agent. In some embodiments, the ferroptosis inhibitor is any agent listed in Table 2. In some embodiments, the ferroptosis inhibitor is liproxstatin-1. In some embodiments, the one or more parameters indicative of ferroptosis are PUFA concentration, PI index, modulation of mesenchymal cell state marker expression, or modulation of iron or selenium concentration. The screening method provided herein can be readily scaled for high throughput analyses, that permit evaluation or prediction of the ferroptosis-inducing activity of test agents. Similarly, the screening method can be performed in animal models as discussed above in the presence and absence of a ferroptosis inhibitor.

Treating a disease or disorder (e.g., cancer) can further result in a decrease in number of hyperproliferative tissues (e.g., tumors). For example, after treatment, hyperproliferative tissue or tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement. The number of tumors may be measured by counting tumors visible to the naked eye or at a specified magnification (e.g., 2×, 3×, 4×, 5×, 10×, or 50×). In some embodiments, methods and ferroptosis-inducing agents provided herein increase the number or activity of leukocytes in a tumor microenvironment. In some embodiments, the leukocytes specifically target cancer cells with a high PUFA concentration as compared with normal cells.

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. The number of metastatic nodules may be measured by counting metastatic nodules visible to the naked eye or at a specified magnification (e.g., 2×, 10×, or 50×).

Treating a disease or disorder (e.g., cancer) can result in an increase in average survival time of a population of subjects treated according to the present invention in comparison to a population of untreated subjects. For example, the average survival time is increased by more than 30 days (more than 60 days, 90 days, 120 days or longer). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with the compound of the invention.

Treating a disease or disorder (e.g., cancer) can also result in a decrease in the mortality rate of a population of treated subjects in comparison to an untreated population. For example, the mortality rate is decreased by more than 2% (e.g., more than 5%, 10%, 25%, or greater). A decrease in the mortality rate of a population of treated subjects may be measured by any reproducible means, for example, by calculating for a population the average number of disease-related deaths per unit time following initiation of treatment with the compound of the invention. A decrease in the mortality rate of a population may also be measured, for example, by calculating for a population the average number of disease-related deaths per unit time following completion of a first round of treatment with a ferroptosis-inducing agent.

Treating a disease or disorder can also result in a decrease in at least one symptom associated with the disease, disorder, or condition. In some embodiments, the methods provided herein reduce at least one symptom of a disease or disorder by at least 10%, 20%, 30%, 40%, 50%, 70%, 80%, 90% or greater relative to number prior to treatment. In some embodiments, following contact with a mammalian tissue or administration of a ferroptosis-inducing agent, cell death can be detected at a time point at or after contacting the mammalian tissue with the ferroptosis-inducing agent. In some embodiments, the methods provided herein increase cell death by at least 5%, 10%, 20%, 30%, 40%, 50%, 60%, 70%, 80%, 90% or greater relative to number prior to treatment.

Therapeutic Applications

Provided herein are methods of treating a disease or a disorder in a subject. In some embodiments, the subject has, is suspected of having, or is at risk of developing a hyperproliferative disease or condition. In some embodiments, methods provided herein further comprise a step of obtaining a biopsy of the tissue for histological analysis. In some embodiments, the tissue comprises a histological abnormality, wherein the histological abnormality is hyperplasia or fibrosis.

In some embodiments, the subject has, is suspected of having, or is at risk of developing a disease or condition associated with abnormal angiogenesis or vascularization. Diseases or conditions associated with abnormal angiogenesis or vascularization can include but are not limited to: ocular neovascularization, macular degeneration, retinopathy, sarcomas, polycystic kidney disease, benign hyperplasias, leiomyomas, adenomas, lipomas, hemangiomas, fibromas, vascular occlusion, restenosis, atherosclerosis, pre-neoplastic lesions, carcinoma in situ, and cancer. In some embodiments, the subject has, is suspected of having, or is at risk of developing an autoimmune disease. Non-limiting examples of relevant autoimmune diseases include: rheumatoid arthritis, inflammatory bowel disease, osteoarthritis, oral hairy leukoplakia, and psoriasis. In some embodiments, the subject has, is suspected of having, or is at risk of developing fibrosis. Non-limiting examples of diseases and conditions associated with fibrosis include: keloid scars, hypertrophic scars, systemic sclerosis, pulmonary arterial hypertension, cardiac fibrosis, hypertrophic cardiomyopathy valvular disease, myelofibrosis, myelodysplastic syndrome, chronic myelogenous leukemia, portal hypertension, hepatocellular carcinoma, retroperitoneal fibrosis, intestinal fibrosis, enteropathies, subretinal fibrosis, epiretinal fibrosis, cystic fibrosis, emphysema, pancreatic fibrosis, chronic pancreatitis, duct obstruction, arthrofibrosis, renal fibrosis, nephrogenic systemic fibrosis, renal anemia, chronic kidney disease, Dupuytren's disease, Ledderhose disease (plantar fibromatosis), primary biliary cholangitis (PBC), non-alcoholic steatohepatitis (NASH), scleroderma, diabetic neuropathy, hypertensive nephrosclerosis, allograft nephropathy, cirrhosis, and pulmonary fibrosis.

In some embodiments, the subject has, is suspected of having, or is at risk of developing cancer. In some embodiments, the subject has a benign tumor. In some embodiments, the subject has a pre-cancerous lesion. In some embodiments, the subject has a basal cell carcinoma (BCC) or a squamous cell carcinoma (SCC). In some embodiments, the subject has a metastatic tumor. In some embodiments, the cancer is a solid cancer or a blood cancer. In some embodiments, the blood cancer is a leukemia or a lymphoma. In some embodiments, the subject has a solid tumor. In some embodiments, the solid tumor is a carcinoma, a melanoma, or a sarcoma. In some embodiments, the melanoma is a dedifferentiated melanoma or amelanotic melanoma. In some embodiments, the subject has a melanoma with a B-Raf proto-oncogene, serine/threonine kinase (BRAF) mutation. In some embodiments the subject has a sarcoma with a Kirsten rat sarcoma (KRAS) mutation. In some embodiments, the sarcoma is a soft tissue sarcoma. In some embodiments, the sarcoma is leiomyosarcoma. In some embodiments, the carcinoma is a colon adenocarcinoma.

Non-limiting examples of cancer that can be treated with an agent provided herein include: acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B cell ALL, T cell ALL), acute myelocytic leukemia (AML) (e.g., B cell AML, T cell AML), chronic myelocytic leukemia (CML) (e.g., B cell CIVIL, T cell CML), and chronic lymphocytic leukemia (CLL) (e.g., B cell CLL, T cell CLL)); lymphoma such as Hodgkin lymphoma (HL) (e.g., B cell HL, T cell HL) and non Hodgkin lymphoma (NHL) (e.g., B cell NHL such as diffuse large cell lymphoma (DLCL) (e.g., diffuse large B cell lymphoma), follicular lymphoma, chronic lymphocytic leukemia/small lymphocytic lymphoma (CLL/SLL), mantle cell lymphoma (MCL), marginal zone B cell lymphomas (e.g., mucosa associated lymphoid tissue (MALT) lymphomas, nodal marginal zone B cell lymphoma, splenic marginal zone B cell lymphoma), primary mediastinal B cell lymphoma, Burkitt lymphoma, lymphoplasmacytic lymphoma (e.g., Waldenstrom's macroglobulinemia), hairy cell leukemia (HCL), immunoblastic large cell lymphoma, precursor B lymphoblastic lymphoma and primary central nervous system (CNS) lymphoma; and T cell NHL such as precursor T lymphoblastic lymphoma/leukemia, peripheral T cell lymphoma (PTCL) (e.g., cutaneous T cell lymphoma (CTCL) (e.g., mycosis fungoides, Sezary syndrome), angioimmunoblastic T cell lymphoma, extranodal natural killer T cell lymphoma, enteropathy type T cell lymphoma, subcutaneous panniculitis like T cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), angiogenic myeloid metaplasia (AMM) a.k.a. myelofibrosis (MF), chronic idiopathic myelofibrosis, chronic myelocytic leukemia (CIVIL), chronic neutrophilic leukemia (CNL), hypereosinophilic syndrome (HES); neuroblastoma; neurofibroma (e.g., neurofibromatosis (NF) type 1 or type 2, schwannomatosis); neuroendocrine cancer (e.g., gastroenteropancreatic neuroendocrine tumor (GEP NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); colorectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Provided herein are methods of administering a ferroptosis-inducing agent to a tissue, wherein the tissue comprises different cell types. In some embodiments, the tissue comprises a heterogeneous population of cells, wherein the heterogeneous population of cells comprises at least one of precancerous cells and non-cancerous cells. In some embodiments, the tissue comprises a heterogeneous population of cells, wherein the heterogeneous population of cells comprises a population of immune cells.

Provided herein is a method of inducing immune cell recruitment to a tumor, the method comprising: administering to a subject a ferroptosis-inducing agent provided herein by any of the methods provided herein. In some embodiments, the administering is sustained administration for at least about 10 hours, thereby recruiting immune cells to the tumor site. In some embodiments, the immune cells are leukocytes. In some embodiments, following contact with a mammalian tissue or administration of a ferroptosis-inducing agent, immune cell recruitment can be detected at a time point at or after contacting the mammalian tissue with the ferroptosis-inducing agent. In some embodiments, the administering reduces the size of the tumor and/or increases the number of leukocytes within the tumor.

Systems

Provided herein are systems for the delivery of a ferroptosis-inducing agent or an iron-dependent cell death inducing agent provided herein. Further provided herein are systems for inducing in vivo ferroptosis, the systems comprising: an implantable microdevice configured for localized administration to a tissue comprising: (a) a cylindrical support structure having at least one microwell on a surface of or formed within the support structure; (b) a microdose of a ferroptosis-inducing agent in the at least one microwell; and (c) a compound release mechanism for sustained administration for controlling a release of the ferroptosis-inducing agent from the microwell, wherein the microdose of the ferroptosis-inducing agent forms a gradient of a sub-therapeutic dose of the ferroptosis-inducing agent an administration site within the tissue for a duration of time of at least 4 hours, wherein the microdevice is configured to permit implantation into the tissue using a catheter, cannula or biopsy needle, and wherein the microdevice is further configured to release the ferroptosis-inducing agent from the at least one microwell to the administration site within the apoptosis-resistant tissue adjacent to the at least one microwell.

Further provided herein are systems for identifying ferroptosis induction in an animal model comprising: (a) an animal model comprising a target tissue of interest; (b) a microdevice configured to permit implantation into a tissue in the animal model using a catheter, cannula or biopsy needle comprising: (i) at least one microwell containing one or more active agents; (ii) a micro-dose of the one or more active agents in the at least one microwell; and (iii) a compound release mechanism comprising a polymeric matrix for controlling the release of the one or more active agents from the microwell into the tissue; wherein the system measures an outcome of ferroptosis induction in the animal model after administration of the one or more active agents into the tissue relative to a baseline tissue without administration of the one or more active agents, and identifying one or more active agents induces ferroptosis in the tissue.

Further provided herein are systems for screening for ferroptosis-induced cell death in vivo, the systems comprising: (a) an animal model comprising a target tissue of interest; (b) a microdevice configured to permit implantation into a tissue in the animal model using a catheter, cannula or biopsy needle comprising: (i) at least one microwell containing one or more active agents; (ii) at least one microwell containing one or more ferroptosis inhibitors; (ii) a microdose of the one or more active agents; and/or one or more ferroptosis inhibitors in the at least one microwell; and (iii) a compound release mechanism comprising a polymeric matrix for controlling the release of the one or more active agents from the microwell into the tissue; wherein the system measures an outcome of ferroptosis induction in the animal model after administration of the one or more active agents into the tissue relative to a baseline tissue without administration of the one or more active agents, wherein the system measures an outcome of ferroptosis induction in the animal model after administration of the one or more active agents into the tissue relative to administration of the one or more active agents and one or more ferroptosis inhibitors, and identifying one or more active agents induces ferroptosis in the tissue.

The systems provided herein generally include multiple microwells arranged on or within a support structure. The microwells contain one or more active agents, alone or in combination, in one or more dosages and/or release pharmacokinetics. Preferably, the devices are configured to deliver the microdose amounts so as to virtually eliminate overlap in the tissue of active agents released from different microwells. In some embodiments, the devices are configured to facilitate implantation and retrieval in a target tissue. In an exemplary embodiment, the device has a cylindrical shape, having symmetrical wells on the outside of the device, each well containing one or more drugs, at one or more concentrations. The device is sized to permit placement using a catheter, cannula, or stylet. In a preferred embodiment, the device has a guidewire to assist in placement and retrieval. The device may also include features that assist in maintaining spatial stability of tissue excised with the device, such as fins or stabilizers that can be expanded from the device prior to or at the time of removal. Optionally, the device has fiber optics, sensors and/or interactive features such as remote accessibility (such as Wi-Fi) to provide for in situ retrieval of information and modification of device release properties. In the most preferred embodiment, the fiber optics and/or sensors are individually accessible to discrete wells.

In some embodiments, the systems provided herein are formed of biocompatible silicon, metal, ceramic or polymers. They may include materials such as radiopaque materials or materials that can be imaged using ultrasound or Mill. They can be manufactured using techniques such as deep ion etching, nano imprint lithography, micromachining, laser etching, three-dimensional printing or stereolithography. Drug can be loaded by injection of a solution or suspension into the wells followed by solvent removal by drying, evaporation, or lyophilization, or by placement of drug in tablet or particulate form into the wells. In a preferred embodiment, drugs are loaded on top of hydrogel pads within the microwells. The hydrogel pads expand during implantation to deliver the drugs to the surrounding tissue. Drug release pharmacokinetics are a function of drug solubility, excipients, dimensions of the wells, and tissue into which the device is implanted (with greater rate of release into more highly vascularized tissue, than into less vascular tissue).

In some embodiments, the systems provided herein are implanted directly into a solid tumor or tissue to be biopsied. Upon implantation, the systems provided herein locally release an array of active agents in microdoses. Subsequent analysis of tumor response to the array of active agents can be used to identify particular drugs, combinations of drugs, and/or dosages that are effective for treating a solid tumor in a patient. By locally delivering microdoses of an array of drugs, the microassay device can be used to test patients for response to large range of regimens, without inducing systemic toxicities, quickly and under actual physiological conditions. These data are used, optionally in combination with genomic data, to accurately predict systemic drug response.

Without limitation, the systems provided herein can administer an agent provided herein according to any of the methods provided herein. For example, a system provided herein can be used to deliver a microdose of an agent to a tissue in vivo. The systems described herein can provide sustained administration of a therapeutic amount of a ferroptosis-inducing agent to a tissue, wherein the sustained administration of said therapeutic amount comprises providing to said tissue the ferroptosis-inducing agent in an amount sufficient to achieve a distribution of at least about 10 ng/mm$^2$ within said tissue for a period of at least 4 hours, thereby inducing ferroptosis in the tissue. In some embodiments, the sustained administration further forms a gradient of a sub-therapeutic amount of the ferroptosis-inducing agent adjacent to the administration site within the tissue. In some embodiments, the sustained administration of a therapeutic amount of a ferroptosis-inducing agent is at least 10 hours. In some embodiments, the therapeutic amount of a ferroptosis-inducing agent is a concentration of at least about 1 µM up to 10 µM. In some embodiments, a system provided herein is implanted into a tumor. In some embodiments, the system delivers one or more a ferroptosis-inducing agents to a tumor.

Exemplary Embodiments

Provided herein are methods of inducing ferroptosis in a tissue in a subject, wherein the methods comprise: sustained administration of a therapeutic amount of a ferroptosis-inducing agent to a tissue, wherein the sustained administration of said therapeutic amount comprises providing to said tissue the ferroptosis-inducing agent in an amount sufficient to achieve a distribution of at least about 10 ng/mm$^2$ within said tissue for a period of at least 4 hours, thereby inducing ferroptosis in the tissue. Further provided herein are methods, wherein the sustained administration further forms a gradient of a sub-therapeutic amount of the ferroptosis-inducing agent adjacent to an administration site within the tissue. Further provided herein are methods, wherein the sustained administration of the ferroptosis-inducing agent comprises additional administration steps. Further provided herein are methods, wherein the tissue comprises a heterogeneous population of cells, wherein the heterogeneous population of cells comprises at least one of precancerous cells and non-cancerous cells. Further provided herein are methods, wherein the tissue comprises a heterogeneous population of cells, wherein the heterogeneous population of cells comprises a population of immune cells. Further provided herein are methods, wherein the tissue comprises a heterogeneous population of cells, wherein the heterogeneous population of cells comprises a first population of cells comprising a greater concentration of selenium or iron compared to a predetermined level of selenium or iron; and a second population of cells comprising a normal concentration of selenium or iron compared to said predetermined level of selenium or iron. Further provided herein are methods, wherein the tissue comprises a homogenous population of cells. Further provided herein are methods, wherein the tissue comprises a plurality of cancer cells. Further provided herein are methods, wherein the tissue comprises a plurality of cells expressing one or more markers indicative of a mesenchymal state. Further provided herein are methods, wherein the one or more markers are selected from the group consisting of: ZEB1, ACSL4, FADS2, PPARγ, Fsp1, SLC7A11, SLC3A2, and LPCAT3. Further provided herein are methods, wherein the tissue comprises a plurality of cells that have a reduction in the expression of one or more endothelial cell markers. Further provided herein are methods, wherein the endothelial cell marker is vimentin, E-cadherin, or beta (β)-actin. Further provided herein are methods, wherein the tissue comprises a histological abnormality. Further provided herein are methods, wherein the histological abnormality is determined by a tissue biopsy prior to or during the targeted, sustained administration of the ferroptosis-inducing agent to the tissue. Further provided herein are methods, wherein the histological abnormality is hyperplasia or fibrosis. Further provided herein are methods, wherein the tissue comprises a plurality of cells with a polyunsaturated fatty acids (PUFA) concentration greater than a PUFA concentration in cells of a normal tissue. Further provided herein are methods, wherein the PUFA concentration in the plurality of greater than a predetermined PUFA concentration. Further provided herein are methods, wherein the tissue comprises a plurality of cells with a peroxidizability index (PI) greater than the PI in cells of normal or healthy tissue; and ferroptosis is induced in the plurality of cells. Further provided herein are methods, wherein the PI in the plurality of cells is greater than a predetermined PI. Further provided herein are methods, wherein the ferroptosis-inducing agent is an inhibitor of glutathione peroxidase 4 (GPX4), glutathione synthetase, glutamate-cysteine ligase, phosphoseryl-TRNA Kinase (PSTK), Eukaryotic Elongation Factor Selenocysteine-TRNA Specific (EEFSEC), Selenophosphate Synthetase 2 (SEPHS2), Sep (O-Phosphoserine) TRNA: Sec (Selenocysteine) TRNA Synthase (SEPSECS), or SECIS Binding Protein 2 (SECISBP2). Further provided herein are methods, wherein the inhibitor is a small molecule, a peptide, or a nucleic acid. Further provided herein are methods, wherein the ferroptosis-inducing agent is any one or more of the agents in Table 1. Further provided herein are methods, wherein the ferroptosis-inducing agent is selected from Table 1, for instance, from the group consisting of: (1S,3R)-RSL3, ML-162, ML-210, JKE-1674, JKE-1716, erastin, jacaric acid, buthionine sulfoximine (BSO), trigonelline, glutamate, sulfasalazine, auranofin, brusatol, sorafenib, sorafenib-d3, sorafenib tosylate, trigonelline, FIN56, FINO$_2$, CIL56, dihydroisotanshinone I, GPX4-IN-3, analogs, or derivatives thereof. Further provided herein are methods, wherein the ferroptosis-inducing agent contacts the tissue at a localized site for about 6 hours. Further provided herein are methods, wherein the ferroptosis-inducing agent contacts the tissue at a localized site for about 10 hours. Further provided herein are methods, wherein the ferroptosis-inducing agent contacts the tissue at a localized site for about 24 hours. Further provided herein are methods, wherein the ferroptosis-inducing agent contacts the tissue at a localized site for about 48 hours. Further provided herein are methods, wherein the ferroptosis-inducing agent contacts the tissue at a localized site for about 72 hours. Further provided herein are methods, wherein the ferroptosis-inducing agent is administered at a concentration of at least about 1 µM to 10 µM. Further provided herein are methods, wherein the tissue is resistant to treatment with an anti-apoptotic agent. Further provided herein are methods, wherein the tissue is a tumor or a tissue comprising a plurality of cancer cells. Further provided herein are methods, wherein the cancer is a solid tumor or a blood cancer. Further provided herein are methods, wherein the blood cancer is a leukemia or a lymphoma. Further provided herein are methods, wherein the solid tumor is a carcinoma, a melanoma, or a sarcoma. Further provided herein are methods, wherein the melanoma is a dedifferentiated melanoma or amelanotic melanoma. Further provided herein are methods, wherein the subject has or is at risk of developing cancer. Further provided herein are methods, wherein the cancer is acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B cell ALL, T cell ALL), acute myelocytic leukemia (AML) (e.g., B cell AML, T cell AML), chronic myelocytic leukemia (CML) (e.g., B cell CIVIL, T cell CML), and chronic lymphocytic leukemia (CLL) (e.g., B cell CLL, T cell CLL)); lymphoma such as Hodgkin lymphoma (HL) (e.g., B cell HL, T cell HL) and non-Hodgkin lymphoma (NHL) (e.g., B cell NHL such as diffuse large cell lymphoma (DLCL) (e.g., diffuse large B cell lymphoma), follicular lymphoma, chronic lymphocytic leukemia/small lymphocytic lymphoma (CLL/SLL), mantle cell lymphoma (MCL), marginal zone B cell lymphomas (e.g., mucosa associated lymphoid tissue (MALT) lymphomas, nodal marginal zone B cell lymphoma, splenic marginal zone B cell lymphoma), primary mediastinal B cell lymphoma, Burkitt lymphoma, lymphoplasmacytic lymphoma (e.g., Waldenstrom's macroglobulinemia), hairy cell leukemia (HCL), immunoblastic large cell lymphoma, precursor B lymphoblastic lymphoma and primary central nervous system (CNS) lymphoma; and T cell NHL such as precursor T lymphoblastic lymphoma/leukemia, peripheral T cell lymphoma (PTCL) (e.g., cutaneous T cell lymphoma (CTCL) (e.g., mycosis fungoides, Sezary syndrome), angioimmunoblastic T cell lymphoma, extranodal natural killer T cell lymphoma, enteropathy type T cell lymphoma, subcutaneous panniculitis like T cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), angiogenic myeloid metaplasia (AMM) a.k.a. myelofibrosis (MF), chronic idiopathic myelofibrosis, chronic myelocytic leukemia (CIVIL), chronic neutrophilic leukemia (CNL), hypereosinophilic syndrome (HES); neuroblastoma; neurofibroma (e.g., neurofibromatosis (NF) type 1 or type 2, schwannomatosis); neuroendocrine cancer (e.g., gastroenteropancreatic neuroendocrine tumor (GEP NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); colorectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; or vulvar cancer (e.g., Paget's disease of the vulva).

Further provided herein are methods of inducing iron-dependent cell death in a tissue in a subject, wherein the methods comprise: contacting a tissue in vivo with an effective amount of an iron-dependent cell death agent for a duration of time of at least 4 hours, wherein the tissue comprises one or more of: (a) a plurality of cells comprising a concentration of selenium greater than a selenium concentration in a corresponding normal tissue; (b) a plurality of cells comprising a concentration of iron greater than an iron concentration in a corresponding normal tissue; (c) a plurality of cells comprising a PUFA concentration greater than a PUFA concentration in a corresponding normal tissue; (d) a plurality of cells expressing one or more markers indicative of a mesenchymal state; and/or (e) a plurality of cells comprising a peroxidizability index (PI) greater than a PI in a corresponding normal tissue, wherein the effective amount of the iron-dependent cell death agent is a concentration of at least about 0.1 µM up to 500 µM in the tissue for the duration of time. Further provided herein are methods, wherein the iron-dependent cell death agent is any one of the agents listed in Table 1. Further provided herein are methods, wherein the ferroptosis-inducing agent is selected from Table 1, for instance, from the group consisting of: (1S,3R)-RSL3, ML-162, ML-210, JKE-1674, JKE-1716, erastin, jacaric acid, buthionine sulfoximine (BSO), trigonelline, glutamate, sulfasalazine, auranofin, brusatol, sorafenib, sorafenib-d3, sorafenib tosylate, trigonelline, FIN56, FINO$_2$, CIL56, dihydroisotanshinone I, GPX4-IN-3, analogs, or derivatives thereof. Further provided herein are methods, wherein the iron-dependent cell death agent contacts the tissue at a localized site for about 6 hours. Further provided herein are methods, wherein the iron-dependent cell death agent contacts the tissue at a localized site for about 10 hours. Further provided herein are methods, wherein the iron-dependent cell death agent contacts the site on the tumor for about 24 hours. Further provided herein are methods, wherein the iron-dependent cell death agent contacts the site on the tumor for about 48 hours. Further provided herein are methods, wherein the iron-dependent cell death agent contacts the site on the tumor for about 72 hours. Further provided herein are methods, wherein the tissue is a tumor or a pre-cancerous lesion. Further provided herein are methods, wherein the tumor is resistant to one or more anti-apoptosis agents. Further provided herein are methods, wherein the tumor is a carcinoma, a melanoma, or a sarcoma. Further provided herein are methods, wherein the melanoma is a dedifferentiated melanoma or a amelanotic melanoma. Further provided herein are methods, wherein the method further comprises a step of obtaining a biopsy of the tissue for histological analysis. Further provided herein are methods, wherein the tissue comprises a histological abnormality, wherein the histological abnormality is hyperplasia or fibrosis. Further provided herein are methods, wherein the one or more markers indicative of a mesenchymal state are selected from the group consisting of: ZEB1, ACSL4, FADS2, PPARγ, Fsp1, SLC7A11, SLC3A2, and LPCAT3. Further provided herein are methods, wherein the tissue comprises a plurality of cells that have a reduction in the expression of one or more endothelial cell markers. Further provided herein are methods, wherein the endothelial cell marker is vimentin, E-cadherin, or beta (β)-actin. Further provided herein are methods, wherein the agent reduces tissue size or tissue volume by at least 5%. Further provided herein are methods, wherein the agent is administered with one additional agent. Further provided herein are methods, wherein the additional agent is a cell death-inducing agent or a dietary supplement.

Further provided herein are methods of inducing targeted cell death in a mammalian tissue in vivo, wherein the methods comprise: (a) contacting a mammalian tissue with a priming agent; (b) contacting the mammalian tissue in vivo with an effective amount of a ferroptosis-inducing agent for a duration of time of at least 4 hours, when a plurality of cells within the mammalian tissue are responsive to the priming agent as determined by detecting in the mammalian tissue: (i) a plurality of cells comprising a concentration of selenium greater than a selenium concentration in the mammalian tissue prior to contacting with the priming agent; (ii) a plurality of cells comprising a concentration of iron greater than an iron concentration in the mammalian tissue prior to contacting with the priming agent; (iii) a plurality of cells comprising a PUFA concentration greater than a PUFA concentration in the mammalian tissue prior to contacting with the priming agent; (iv) a plurality of cells expressing one or more markers indicative of a mesenchymal state; (v) a plurality of cells comprising a peroxidizability index (PI) greater than a PI in the mammalian tissue prior to contacting with the priming agent; and/or (vi) hyperproliferation of cells in the mammalian tissue, wherein the ferroptosis-inducing agent induces targeted cell death in the mammalian tissue in vivo. Further provided herein are methods, wherein step (a) is performed, in vivo, in vitro, or ex vivo. Further provided herein are methods, wherein the methods further comprise a step of obtaining a biopsy of the mammalian tissue for histological analysis. Further provided herein are methods, wherein the methods further comprise a step of detecting a plurality of cells within the mammalian tissue as responsive to the priming agent. Further provided herein are methods, wherein the detecting is via a histological assay or an immunohistochemical assay. Further provided herein are methods, wherein the priming agent is any one of the agents listed in Table 2. Further provided herein are methods, wherein the priming agent is priming agent is liproxstatin-1, ferrostatin-1, deferoxamine (DFO), iron, vitamin E, a polyunsaturated fatty acid, or selenium. Further provided herein are methods, wherein the methods further comprise administering a cell death-inducing agent. Further provided herein are methods, wherein the cell-death inducing agent is a chemotherapeutic agent. Further provided herein are methods, wherein the ferroptosis-inducing agent is any one of the agents listed in Table 1. Further provided herein are methods, wherein the ferroptosis-inducing agent is selected from Table 1, for instance, from the group consisting of (1S,3R)-RSL3, ML-162, ML-210, JKE-1674, JKE-1716, erastin, jacaric acid, buthionine sulfoximine (BSO), trigonelline, glutamate, sulfasalazine, auranofin, brusatol, sorafenib, sorafenib-d3, sorafenib tosylate, trigonelline, FIN56, FINO$_2$, CIL56, dihydroisotanshinone I, GPX4-IN-3, analogs, or derivatives thereof. Further provided herein are methods, wherein the ferroptosis-inducing agent contacts the mammalian tissue for about 6 hours. Further provided herein are methods, wherein the ferroptosis-inducing agent contacts the mammalian tissue for about 10 hours. Further provided herein are methods, wherein the ferroptosis-inducing agent contacts the mammalian tissue for about 24 hours. Further provided herein are methods, wherein the ferroptosis-inducing agent contacts the mammalian tissue for about 48 hours. Further provided herein are methods, wherein the ferroptosis-inducing agent contacts the mammalian tissue for about 72 hours. Further provided herein are methods, wherein the effective amount of the ferroptosis-inducing agent is a concentration of at least about 1 µM to 10 µM. Further provided herein are methods, wherein following contact with a ferroptosis-inducing agent, cell death can be detected at a time point at or after contacting the mammalian tissue with the ferroptosis-inducing agent. Further provided herein are methods, wherein following contact with a ferroptosis-inducing agent, immune cell recruitment can be detected at a time point at or after contacting the mammalian tissue with the ferroptosis-inducing agent. Further provided herein are methods, wherein the tissue is human tissue. Further provided herein are methods, wherein the administering or contacting step is via intratumoral injection, oral administration, transdermal injection, inhalation, nasal administration, topical administration, vaginal administration, ophthalmic administration, intracerebral administration, rectal administration. Further provided herein are methods, wherein the administering or contacting step is via intravenous administration, intra-arterial administration, intramuscular administration, or subcutaneous administration.

Further provided herein are systems, wherein the systems comprise: an implantable microdevice configured for localized administration to a tissue comprising: (a) a cylindrical support structure having at least one microwell on a surface of or formed within the support structure; (b) a microdose of a ferroptosis-inducing agent in the at least one microwell; and (c) a compound release mechanism for sustained administration for controlling a release of the ferroptosis-inducing agent from the microwell, wherein the microdose of the ferroptosis-inducing agent forms a gradient of a sub-therapeutic dose of the ferroptosis-inducing agent an administration site within the tissue for a duration of time of at least 4 hours, wherein the microdevice is configured to permit implantation into the tissue using a catheter, cannula or biopsy needle, and wherein the microdevice is further configured to release the ferroptosis-inducing agent from the at least one microwell to the administration site within the apoptosis-resistant tissue adjacent to the at least one microwell.

Further provided herein are systems for screening for ferroptosis-induced cell death in vivo, the systems comprising: (a) an animal model comprising a target tissue of interest; (b) a microdevice configured to permit implantation into a tissue in the animal model using a catheter, cannula or biopsy needle comprising: (i) at least one microwell containing one or more active agents; (ii) at least one microwell containing one or more ferroptosis inhibitors; (ii) a microdose of the one or more active agents; and/or one or more ferroptosis inhibitors in the at least one microwell; and (iii) a compound release mechanism comprising a polymeric matrix for controlling the release of the one or more active agents from the microwell into the tissue; wherein the system measures an outcome of ferroptosis induction in the animal model after administration of the one or more active agents into the tissue relative to a baseline tissue without administration of the one or more active agents, wherein the system measures an outcome of ferroptosis induction in the animal model after administration of the one or more active agents into the tissue relative to administration of the one or more active agents and one or more ferroptosis inhibitors, and identifying one or more active agents induces ferroptosis in the tissue.

Further provided herein are systems for screening for ferroptosis-induced cell death in vivo, the systems comprising: (a) an animal model comprising a target tissue of interest; (b) a microdevice configured to permit implantation into a tissue in the animal model using a catheter, cannula or biopsy needle comprising: (i) at least one microwell containing one or more active agents; (ii) at least one microwell containing one or more ferroptosis inhibitors; (ii) a microdose of the one or more active agents; and/or one or more ferroptosis inhibitors in the at least one microwell; and (iii) a compound release mechanism comprising a polymeric matrix for controlling the release of the one or more active agents from the microwell into the tissue; wherein the system measures an outcome of ferroptosis induction in the animal model after administration of the one or more active agents into the tissue relative to a baseline tissue without administration of the one or more active agents, wherein the system measures an outcome of ferroptosis induction in the animal model after administration of the one or more active agents into the tissue relative to administration of the one or more active agents and one or more ferroptosis inhibitors, and identifying one or more active agents induces ferroptosis in the tissue. Further provided herein are systems, wherein the ferroptosis inhibitor is liproxstatin-1 or ferrostatin-1.

Further provided herein are methods of modulating ferroptosis in vivo, the methods comprising: (a) contacting a mammalian tissue in vivo with an effective amount of a ferroptosis-inducing agent for a duration of time of at least 4 hours, wherein the ferroptosis-inducing agent induces targeted cell death in the mammalian tissue in vivo; and (b) contacting the mammalian tissue in vivo with an effective amount of a ferroptosis-inducing agent and a ferroptosis inhibitor, thereby modulation ferroptosis in vivo. Further provided herein are methods, wherein the ferroptosis inhibitor is liproxstatin-1, ferrostatin-1, deferoxamine (DFO), iron, vitamin E, a polyunsaturated fatty acid, or selenium. Further provided herein are methods, wherein the ferroptosis-inducing agent is an inhibitor of glutathione peroxidase 4 (GPX4), glutathione synthetase, glutamate-cysteine ligase, phosphoseryl-TRNA Kinase (PSTK), Eukaryotic Elongation Factor Selenocysteine-TRNA Specific (EEFSEC), Selenophosphate Synthetase 2 (SEPHS2), Sep (O-Phosphoserine) TRNA: Sec (Selenocysteine) TRNA Synthase (SEPSECS), or SECIS Binding Protein 2 (SECISBP2). Further provided herein are methods, wherein the ferroptosis-inducing agent is selected from the group consisting of (1S,3R)-RSL3, ML-162, ML-210, JKE-1674, JKE-1716, erastin, jacaric acid, buthionine sulfoximine (BSO), trigonelline, glutamate, sulfasalazine, auranofin, brusatol, sorafenib, sorafenib-d3, sorafenib tosylate, trigonelline, FIN56, FINO$_2$, CIL56, dihydroisotanshinone I, GPX4-IN-3, analogs, or derivatives thereof. Further provided herein are methods, wherein the ferroptosis-inducing agent contacts the mammalian tissue for about 6 hours. Further provided herein are methods, wherein the ferroptosis-inducing agent contacts the mammalian tissue for about 10 hours. Further provided herein are methods, wherein the ferroptosis-inducing agent contacts the mammalian tissue for about 24 hours. Further provided herein are methods, wherein the ferroptosis-inducing agent contacts the mammalian tissue for about 48 hours. Further provided herein are methods, wherein the ferroptosis-inducing agent contacts the mammalian tissue for about 72 hours. Further provided herein are methods, wherein the effective amount of the ferroptosis-inducing agent is a concentration of at least about 1 µM to 10 µM. Further provided herein are methods, wherein following contact with a ferroptosis-inducing agent, cell death can be detected at a time point at or after contacting the mammalian tissue with the ferroptosis-inducing agent. Further provided herein are methods, wherein following contact with a ferroptosis-inducing agent, immune cell recruitment can be detected at a time point at or after contacting the mammalian tissue with the ferroptosis-inducing agent. Further provided herein are methods, wherein the tissue is human tissue. Further provided herein are methods, wherein the administering or contacting step is via intratumoral injection, oral administration, transdermal injection, inhalation, nasal administration, topical administration, vaginal administration, ophthalmic administration, intracerebral administration, rectal administration. Further provided herein are methods, wherein the administering or contacting step is via intravenous administration, intra-arterial administration, intramuscular administration, or subcutaneous administration. Further provided herein are methods, wherein the method further comprises measuring one or more parameters indicative of ferroptosis in the mammalian tissue, wherein the one or parameters are selected from: concentration of selenium; concentration of iron; PUFA concentration; expression one or more markers indicative of a mesenchymal state; peroxidizability index (PI); and/or cell proliferation.

Further provided herein are compositions for the treatment of a disease or disorder, wherein the compositions comprise any one of the agents in Table 1 or a combination of agents; and a system provided herein.

Further provided herein are pharmaceutical compositions for the treatment of a disease or disorder, wherein the pharmaceutical compositions comprise any one of the agents in Table 1 or a combination of agents; and a pharmaceutically acceptable excipient. Further provided herein are pharmaceutical compositions for the treatment of a disease or disorder, wherein the pharmaceutical compositions comprise any one of the agents in Table 1, Table 2, or a combination of agents; and a pharmaceutically acceptable excipient.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Cell Lines and Culture Conditions

Human cancer cell lines are cultured in Ham's F12 medium supplemented with 10% (v/v) fetal bovine serum (FBS), penicillin (100 U/mL), and streptomycin (100 µg/mL). human cancer cells are cultured in RPMI medium supplemented with 10% FBS, penicillin (100 U/mL), and streptomycin (100 µg/mL). Cells are grown in a humidified incubator at 37° C. with 5% carbon dioxide and split every 3-4 days using trypsin/EDTA solution.

Method to add exogenous PUFAs or MUFAs: Exogenous fatty acids were dissolved in DMSO and added to cell culture medium 24 h after seeding cells.

Example 2: Determination of PUFA Status

Lipidomics are performed using either gas chromatography-mass spectrometry (GC-MS) or direct infusion mass spectrometry.

For GC-MS assessment of cellular PUFA status, the membrane lipids are trans-esterified with 500 μL methanolic HCl, 250 μL n-hexane and 500 μL internal standard (0.8 mg Di-C17-phosphatidylcholine in 1 mL methanol with 0.2% Butylhydroxytoluol as antioxidant). After cooling-off, 500 μL n-hexane and 1 mL Aqua Dest. are added. The upper hexane phase is evaporated with nitrogen. The fatty acid methylesters (FAME) are taken up in 60 μL n-hexane. An aliquot of 1 μL is injected on-column on a Varian CP 3800 gas chromatograph (Varian, Darmstadt, Germany) equipped with an Omegawax TM 320 column (0.32 mm internal diameter, 30 m length) (Supelco, Bellefonte, USA). The column temperature was 200 degrees C.

For direct infusion MS analysis, lipids are extracted using a two-step chloroform/methanol procedure. Samples are spiked with internal lipid standard mixture containing: cardiolipin 16:1/15:0/15:0/15:0 (CL), ceramide 18:1;2/17:0 (Cer), diacylglycerol 17:0/17:0 (DAG), hexosylceramide 18:1;2/12:0 (HexCer), lyso-phosphatidate 17:0 (LPA), lyso-phosphatidylcholine 12:0 (LPC), lyso-phosphatidylethanolamine 17:1 (LPE), lyso-phosphatidylglycerol 17:1 (LPG), lyso-phosphatidylinositol 17:1 (LPI), lyso-phosphatidylserine 17:1 (LPS), phosphatidate 17:0/17:0 (PA), phosphatidylcholine 17:0/17:0 (PC), phosphatidylethanolamine 17:0/17:0 (PE), phosphatidylglycerol 17:0/17:0 (PG), phosphatidylinositol 16:0/16:0 (PI), phosphatidylserine 17:0/17:0 (PS), cholesterol ester 20:0 (CE), sphingomyelin 18:1;2/12:0;0 (SM), triacylglycerol 17:0/17:0/17:0 (TAG). After extraction, the organic phase is transferred to an infusion plate and dried in a speed vacuum concentrator. The dried extract is re-suspended in 7.5 mM ammonium acetate in chloroform/methanol/propanol (1:2:4, V:V:V) and the second step dry extract is re-suspended in a 33% ethanol solution of methylamine in chloroform/methanol (0.003:5:1; V:V:V). Samples are analyzed by direct infusion on a QExactive mass spectrometer (ThermoFisher Scientific) equipped with a TriVersa NanoMate ion source (Advion Biosciences). Samples are analyzed in both positive and negative ion modes with a resolution of Rm/z=200=280000 for MS and Rm/z=200=17500 for tandem mass spectrometry (MS-MS) assays, in a single acquisition. MS-MS is triggered by an inclusion list encompassing corresponding MS mass ranges scanned in 1 Da increments.

Example 3: Cell Line Profiling with a Ferroptosis-Inducing Agent with and without a Rescue Agent Cell viability assays are performed by seeding 1,000 cells per well (30 μl volume) in opaque white 384-well plates (Corning). Cells are allowed to adhere for 24 h, after which they are exposed to compounds for 72 hours. DMSO stock solutions of compounds are added to cells using a CyBio Well Vario liquid dispenser (Analytik Jena AG). Cellular ATP levels are measured using CellTiter-Glo (Promega) as a surrogate for viability. Rescue assays are performed using rescue agents selected from Table 2 and referred to in the assays as anti-ferroptosis rescue agent (N) (N, 1.5 μM), anti-ferroptosis rescue agent (M) (M, 1 μM), anti-ferroptosis rescue agent (P) (P, 50 μM), and other ferroptosis inhibitors added to cells at the time of addition to assay plates.

Knocking Down Targets Using Genetic Reagents +/− Anti-Ferroptosis Rescue Agent (N)

For lentiviral shRNA production, 293-T cells are seeded in 6-well dishes in antibiotic free media (280,000 cells/well). The next day, cells were transfected using FuGENE with the appropriate shRNA encoding plasmid (450 ng), viral packaging plasmid (p-Delta8.9, 400 ng), and viral envelope plasmid (p-VSV-G, 45 ng). After 24 h, the medium is removed and replaced with fresh medium. Three collections of viral supernatant per shRNA are made over 36 h and pooled. The combined supernatant is centrifuged, aliquoted, and stored at −80 degrees C. until virus infection.

Lentiviral infections are performed by seeding cells for 12 h and replacing the media with media supplemented with polybrene (8 μg/mL) and an aliquot of the viral supernatant. Plates are incubated for 48 h and the media is replaced with media containing 1.5 μg/mL puromycin and incubated at 37 degrees C. for 48 h. Knockdown is assessed by immunoblotting and RT-qPCR.

Knocking Out Targets Using Genetic Reagents +/− Anti-Ferroptosis Rescue Agent (N)

For generation of cell lines with gene knockouts, lentiviruses are generated by overnight polyethylenimine transfection of Leni-X 293T cells with target lentiviral plasmid and packaging plasmids pCMV-dR8.2 dvpr and pCMV-VSV-G in DMEM supplemented with 10% FBS. The next day, the medium is changed to fresh DMEM with 10% FBS. After 24 and 48 h, the virus-containing medium is collected and filtered with a 0.45 μm polyethersulfone filter, combined, and stored at −80 degrees C. until virus infection.

Cells are transduced with pLenti-CRISPR-V2 encoding the appropriate sgRNAs for the target genes using 2 μg/mL of polybrene followed by puromycin selection (1 μg/mL) for 4 days in the presence of ferrostatin-1 (1 Protein knockout is verified via immunoblotting.

Example 4: Use of C11-BODIPY to Show Lipid Peroxidation as an Indicator of Ferroptosis Imaging assay: human cancer cells are seeded at 5,000 cells per well in a CellCarrier Ultra 96-well plate (Perkin-Elmer) in 150 μl of RPMI medium with 10% FBS. Cells are incubated for 24 h at 37° C. and then treated with the indicated compounds or DMSO (90 min, 37° C.). During the last 30 min of incubation, 60 nM DRAQ7 (Abcam), 1 μg ml$^{-1}$ Hoechst 33342 (ThermoFisher) and 1μM BODIPY 581/591 C11 (ThermoFisher) dyes are added. Cells are imaged using an Opera Phenix High-Content Screening System (Perkin-Elmer) equipped with 405, 488, 560 and 647 nm lasers. Image analysis is conducted with Harmony High-Content Imaging and Analysis software (Perkin-Elmer).

Use of C11-BODIPY to Show Lipid Peroxidation (Flow Cytometry Assay)

Human cancer cells are seeded at 15,000 cells per well in 96-well plates in RPMI medium with 10% FBS. After 48 h, culture media is replaced with 200μl media containing either DMSO or the indicated inhibitor (10 μM) and 1 μM anti-ferroptosis rescue agent (where indicated). Cultures are incubated at 37° C. for 2 h. Thirty minutes before the end of the incubation period, 10 μM BODIPY 581/591 C11 (Molecular Probes no. C10445) is added to cells. Cells are gathered in 200 μl PBS+0.1% BSA and subjected to flow cytometry analysis (BD FACSCanto II).

Example 5: Microdosing Tumors with Ferroptosis-Inducing Agents

For the allograft study, cancer cell line-derived tumor cells were injected into the flanks of male C57BL6/J mice. Assays were initiated when the tumor diameter was approximately 6-7 mm.

Microdose drug delivery was performed for the assay described herein. The compounds in Table 3 were packed into device reservoirs using a tapered metal needle. Reservoirs were loaded for initial release of anti-ferroptosis rescue agent (M) (where included) followed by a 4-6 h delayed release of ferroptosis inducers. Devices were prepared for dose administration into mouse tumors. Devices delivered the ferroptosis inducing agent for 24-72 hours in the tissue. The tumor was then excised, and the tissue was snap frozen with liquid nitrogen. Tissue was sectioned using a standard cryotome, and tissue slices of 20 μm in thickness were collected from each reservoir for analysis by immunoassays, transcriptomics, and metabolomic assays.

TABLE 3

Microdosing Ferroptosis-Inducing Agents and Conditions

| Reservoir # | Compound Name | Loading | Rescue agent | Target concentration range (μM) |
|---|---|---|---|---|
| 1 | ferroptosis-inducing agent(C) | high | | 1-100 |
| 2 | ferroptosis-inducing agent(C) | high | M | 1-100 |
| 3 | ferroptosis-inducing agent(C) | low | | 1-10 |
| 4 | ferroptosis-inducing agent(C) | low | M | 1-10 |
| 5 | ferroptosis-inducing agent(B) | high | | 1-10 |
| 6 | ferroptosis-inducing agent(B) | high | M | 1-10 |
| 7 | ferroptosis-inducing agent(D) | high | | 1-10 |
| 8 | ferroptosis-inducing agent(D) | high | M | 1-10 |
| 9 | ferroptosis-inducing agent (E) | high | | 5-500 |
| 10 | ferroptosis-inducing agent (E) | high | M | 5-500 |
| 11 | ferroptosis-inducing agent(A) | high | | 100-150 |
| 12 | ferroptosis-inducing agent(A) | high | M | 100-150 |
| 13 | ferroptosis-inducing agent(F) | high | | 1-10 |
| 14 | ferroptosis-inducing agent(F) | high | M | 1-10 |
| 16 | Empty | | M | 1-10 |

Example 6: Ferroptosis Induction by Sustained, Targeted Administration of Ferroptosis-Inducing Agent (A)

A drug delivery system was applied to a: solid tumor animal model. Animals were administered (1) ferroptosis-inducing agent (A) or (2) ferroptosis-inducing agent (A)+anti-ferroptosis rescue agent (M) as a ferroptosis-rescue agent. Drugs were loaded into an implantable drug delivery system to achieve concentrations of 1-10 μM for both ferroptosis-inducing agent (A) and ferroptosis-inducing compound (A)+anti-ferroptosis rescue agent (M) at the tumor site.

Figure 2A:
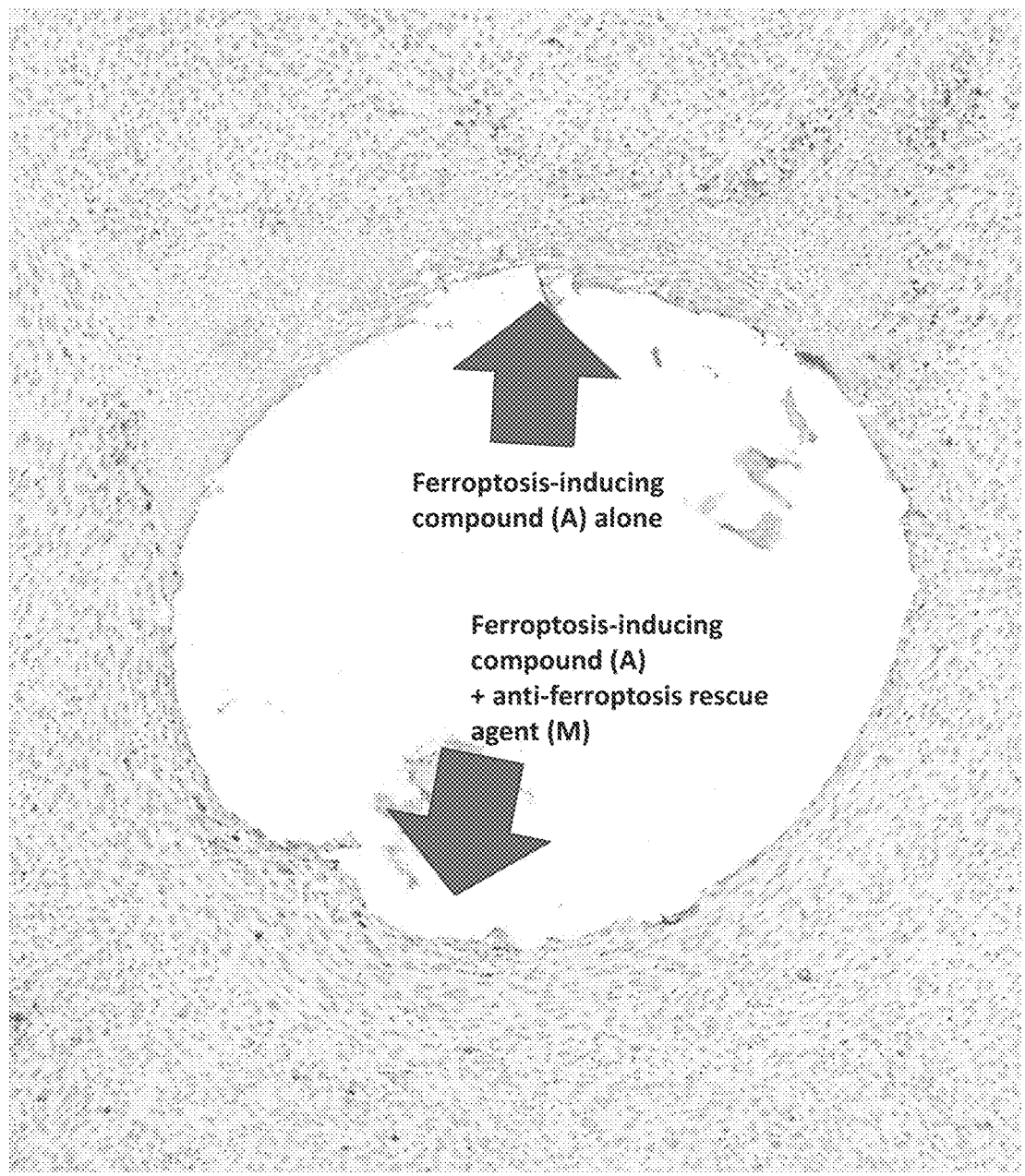
FIGS. 2A-2B demonstrate tumor response after exposure to (1) ferroptosis-inducing compound (A) or (2) ferroptosis-inducing compound (A)+anti-ferroptosis rescue agent (M) after 24 hours.
Figure 2B:
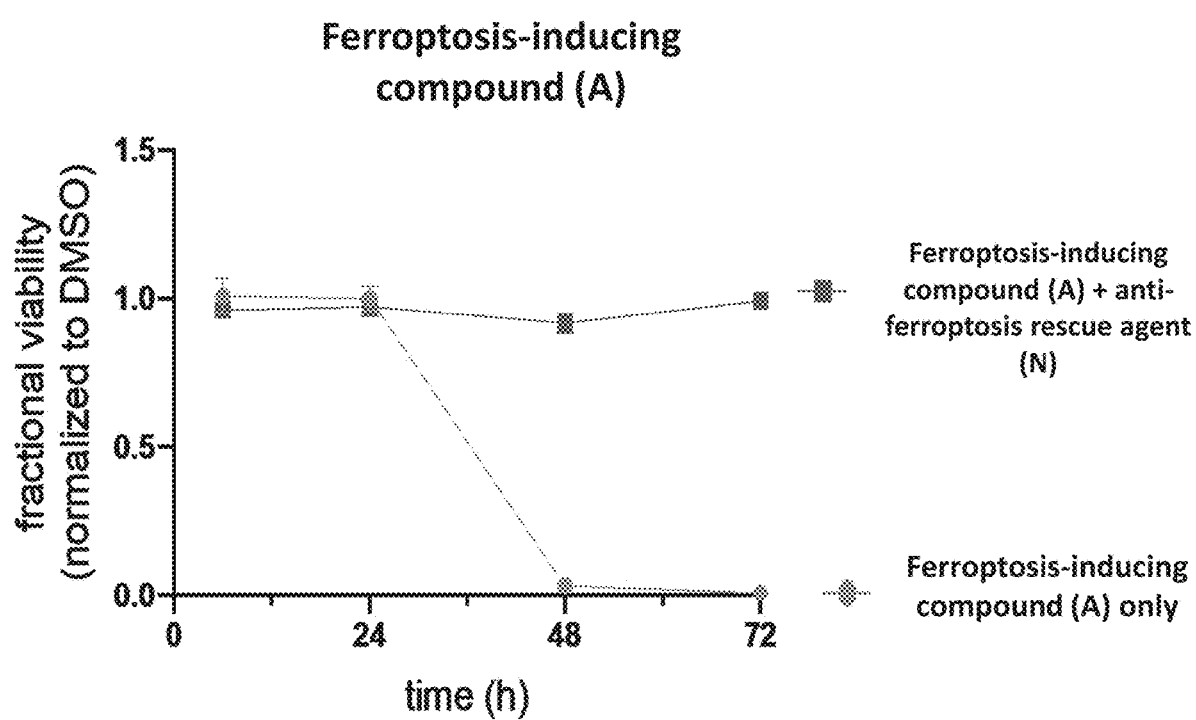

After 24 hours, tumors were removed and stained for cleaved caspase-3 to indicate cell death in the tumor (FIG. 2A). The ferroptosis-inducing compound (A)-treated tumor section show the recruitment of white blood cells to the tumor indicating immune cell recruitment and cell death at the tumor site. Tumors treated with ferroptosis-inducing compound (A) also exhibited significant reductions in fractional viability as compared with ferroptosis-inducing compound (A)+anti-ferroptosis rescue agent (M) treated sections of the tumor (FIG. 2B). Therefore, ferroptosis can be induced by both local and systemic administration of ferroptosis-inducing agent (A).

Example 7: Ferroptosis Induction by Sustained, Targeted Administration of Ferroptosis-Inducing Agent (B)

Figure 3:
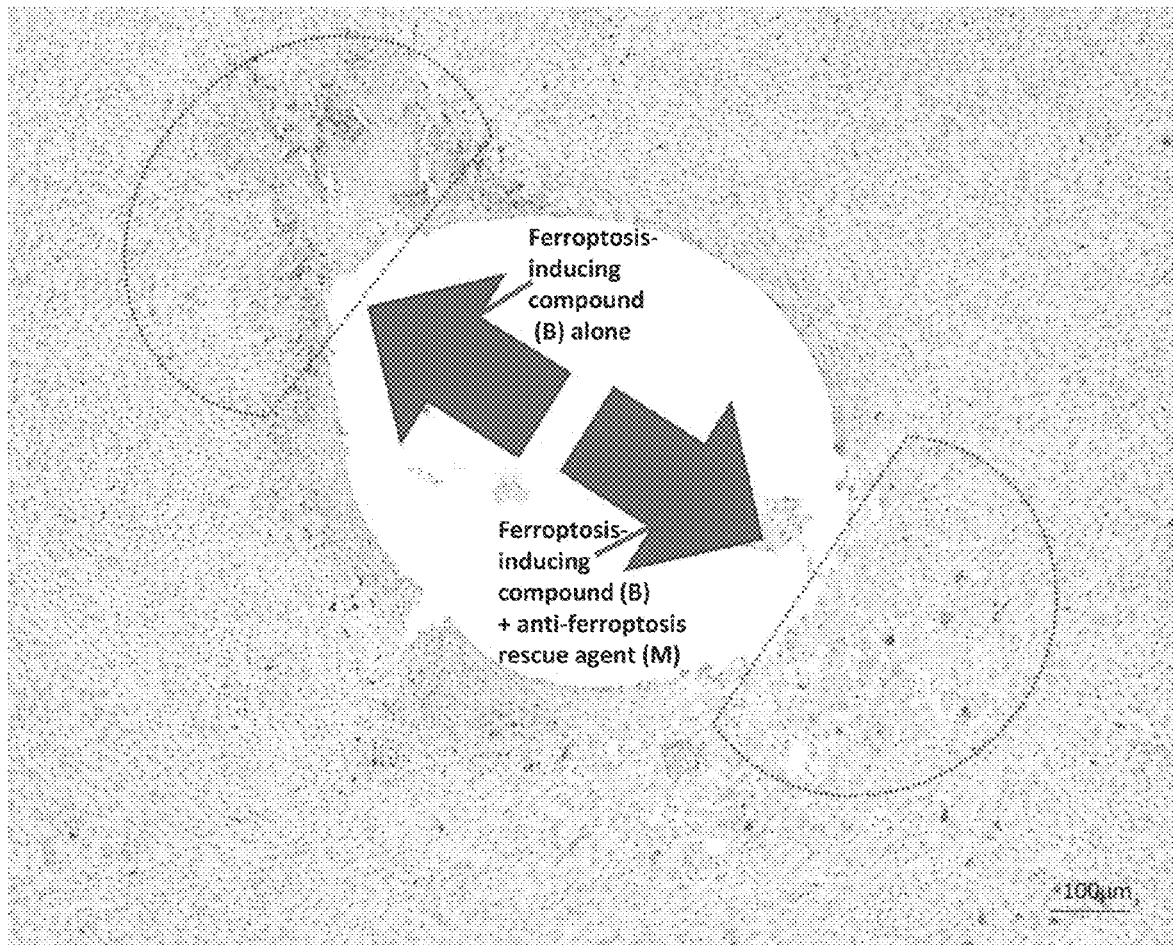
FIG. 3 demonstrates tumor response after exposure to (1) ferroptosis-inducing compound (B) or (2) ferroptosis-inducing compound (B)+anti-ferroptosis rescue agent (M) after 24 hours. Drug were loaded to achieve concentrations of 1-10 μM for both ferroptosis-inducing compound (A) and anti-ferroptosis rescue agent (M). Staining shows cleaved caspase-3. Dashed lines indicate region of drug exposure. Scale bar: 100 micrometers (μm).

A drug delivery system was applied to a: solid tumor animal model. Animals were administered (1) ferroptosis-inducing agent (B) or (2) ferroptosis-inducing agent (B)+anti-ferroptosis rescue agent (M), as a ferroptosis rescue agent. Drugs were loaded into an implantable drug delivery system to achieve concentrations of 1-10 μM for both ferroptosis-inducing agent (B) and ferroptosis-inducing agent (B)+anti-ferroptosis rescue agent (M) at the tumor site. After 24 hours, tumors were removed and stained for cleaved caspase-3. The ferroptosis-inducing agent (B) treated tumor section shows the recruitment of white blood cells to the tumor indicating immune cell recruitment and cell death at the tumor site (FIG. 3).

Example 8: Ferroptosis Induction by Administration of Ferroptosis-Inducing Agent (C)

Figure 4:
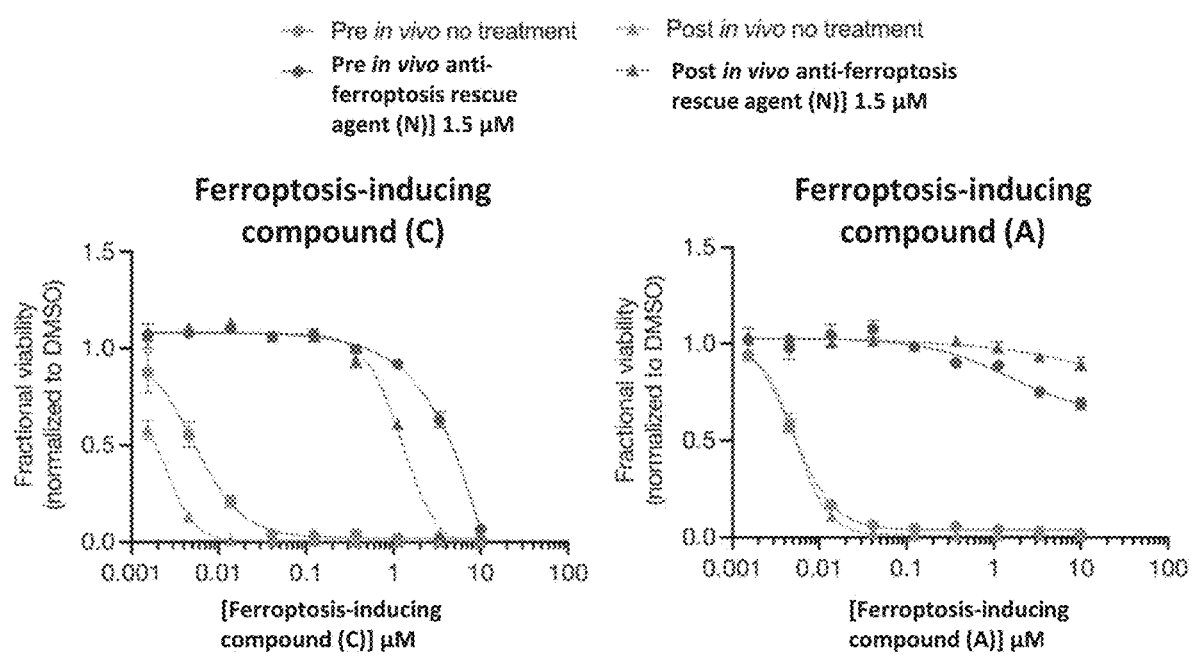
FIG. 4 demonstrates dose-response curves for ferroptosis-inducing compound (A) and ferroptosis-inducing compound (C) on fractional cell viability (y-axis) normalized to DMSO. The x-axis shows drug concentration.

Dose-response curves for ferroptosis-inducing agent (A) and ferroptosis-inducing agent (C) are shown in FIG. 4 with and without anti-ferroptosis rescue agent treatment (indicated as no treatment or +1.5 μM anti-ferroptosis rescue agent (N)). Anti-ferroptosis rescue agent (N) prevents cell death in ferroptosis-inducing agent (C) and ferroptosis-inducing agent (A) treated tumors in vivo. Furthermore, post-in vivo treatment with ferroptosis-inducing agent (C) and anti-ferroptosis rescue agent (N) showed a reduction in the fractional viability of cancer cells that was not observed with ferroptosis-inducing agent (A)+anti-ferroptosis rescue agent (N), indicating that ferroptosis-inducing agent (C) is a robust inducer of ferroptosis.

Figure 5A:
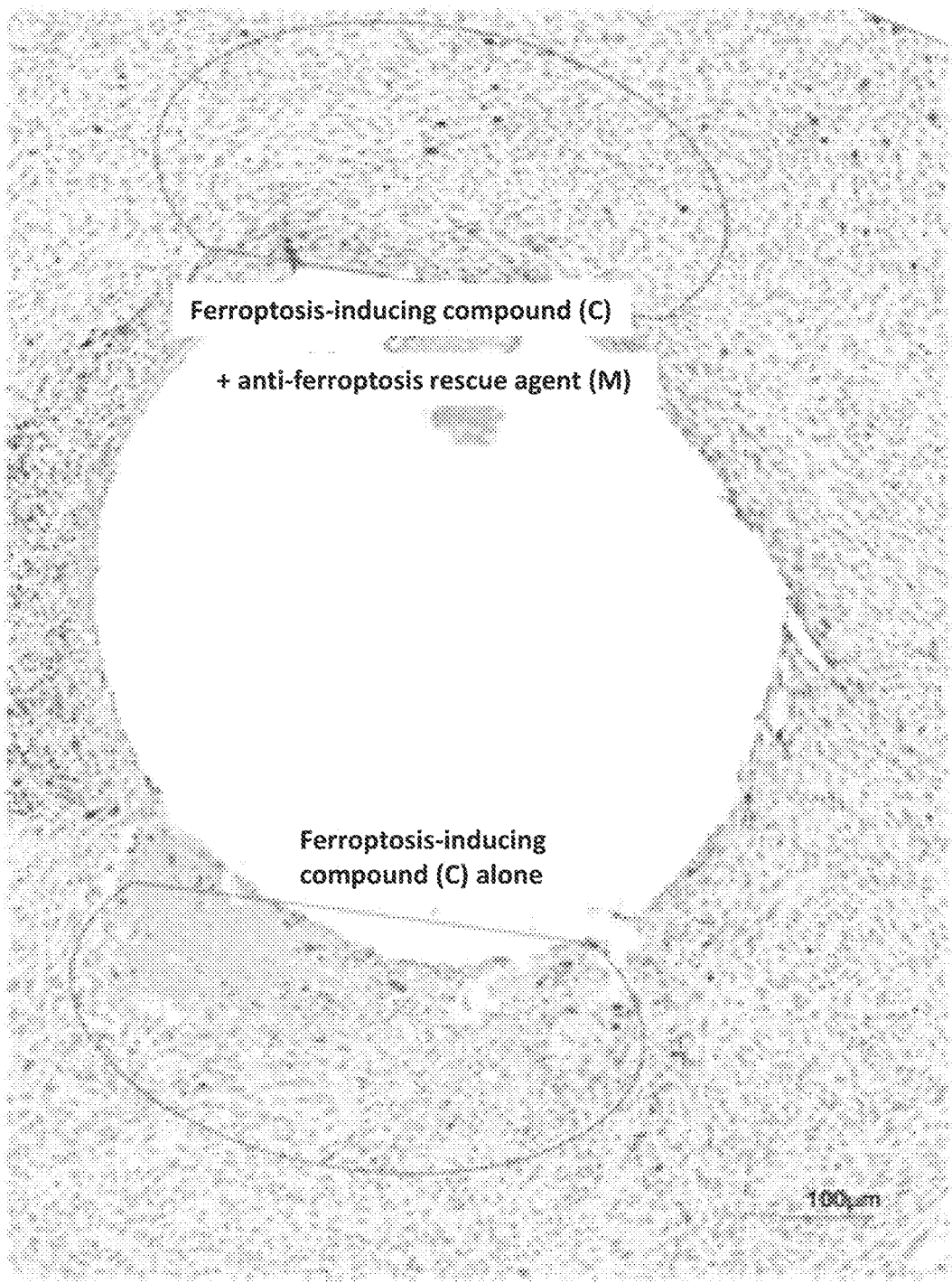
FIGS. 5A-5B demonstrate tumor response after exposure to (1) ferroptosis-inducing compound (C) or (2) ferroptosis-inducing compound (C)+anti-ferroptosis rescue agent (M) after 24 hours. Drug were loaded to achieve concentrations of 1-10 μM for both ferroptosis-inducing compound (C) and anti-ferroptosis rescue agent (M).
Figure 5B:
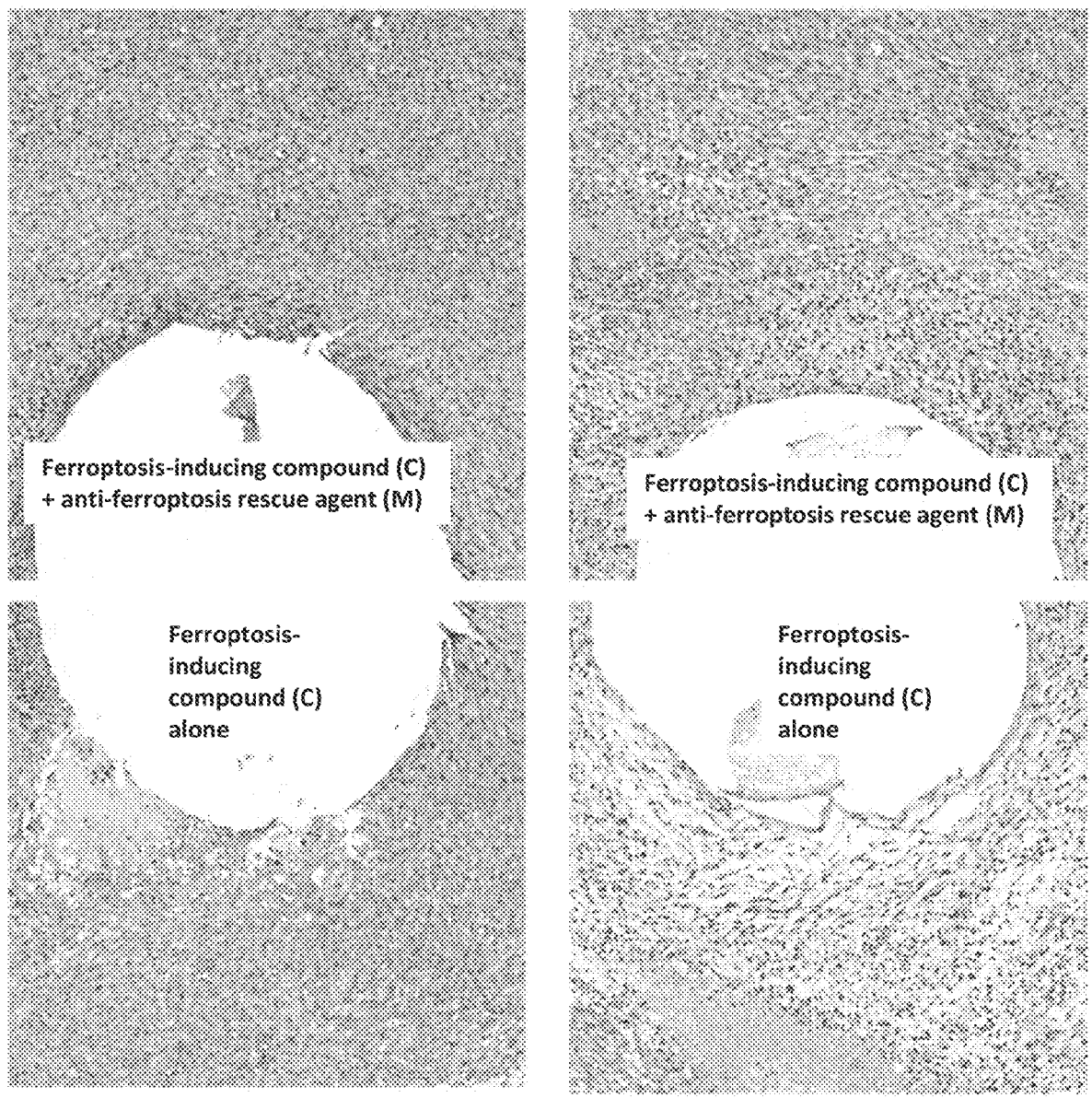

To achieve therapeutic doses of ferroptosis-inducing agent (C) in vivo, a drug delivery system was applied to a: solid tumor animal model. Animals were administered (1) ferroptosis-inducing agent (C) or (2) ferroptosis-inducing agent (C)+anti-ferroptosis rescue agent (M) as a ferroptosis rescue agent. Drugs were loaded into an implantable drug delivery system to achieve concentrations of 1-10 μM for both ferroptosis-inducing agent (C) and ferroptosis-inducing agent (C) and anti-ferroptosis rescue agent (M) co-administration at the tumor site. After 24 hours of sustained administration, tumors were removed and stained for cleaved caspase-3 (FIG. 5A). Dashed lines indicate region of drug exposure. FIG. 5B shows representative H&E images at 18 hrs post treatment with (1) ferroptosis-inducing agent (C) or (2) ferroptosis-inducing agent (C)+anti-ferroptosis rescue agent (M) as indicated. White blood cell recruitment and cell death were prominent in ferroptosis-inducing agent (C) treated tumor sections as compared with ferroptosis-inducing agent (C)+anti-ferroptosis rescue agent (M) treated tumor sections.

Example 9: System for In Vivo Ferroptosis-Inducing Agent Delivery

Ferroptosis-inducing agents and/or priming agents are administered systemically by injection to a mammal to establish local pharmacokinetics for the drugs. Representative drugs are tested include: ferroptosis-inducing agent (A), ferroptosis-inducing agent (C), ferroptosis-inducing agent (B), and anti-ferroptosis rescue agent (M). Representative animal models that can be used include for instance, those harboring tumors in a flammable membrane state.

A drug delivery system with microwells is loaded with approximately 1.5 micrograms of a ferroptosis-inducing agent (crystalline powder) per microwell. The system is loaded with the same drugs based on the results of the systemic testing. Each drug is loaded separately and in more than one concentration, as well as in combination. After 10, 12, 18, 24, 36 or 48 hours, devices are removed and histology of the tissue was examined to determine the effect of the ferroptosis-inducing agents on the tumor cells adjacent to each well. The effects of compounds eluted from microwells are assessed by different techniques. Tissue excised with the device is assayed by standard histopathological techniques, including immunohistochemistry and immunofluorescence. Ingrowth of tissue, ranging from 20 to about 300 microns, are visualized by staining tissue/device section by standard immuno-histochemistry (IHC) techniques, including hematoxylin & eosin (H&E) staining, or any nuclear cell stain such as DAPI. Mass spectrometry is used to measure local biomarkers indicative of an effect of a ferroptosis-inducing agent (e.g., mesenchymal cell state markers or PUFA concentration). Analysis for apoptosis, necrosis, mitotic cell death, and proliferation is conducted. The local microdose response is determined and used to define an appropriate therapeutic regime for the cancer.

Several methods for controlling the release/diffusion of ferroptosis-inducing agents into tissue, including precise spatial placement of microwells along device mantle; geometry and size of microwells; and formulation of released agents are developed. The device microwells from which the ferroptosis-inducing agents diffuse are engineered to expose only regions of tissue that are directly adjacent to the microwell opening, to the agent that is being released. This creates distinct local regions in the tissue in which the effects of compounds are assessed without interference of other compounds released from different microwells. Creation of discrete areas of drug are useful to assess the efficacy of the different agents, or combinations thereof, and/or dosages and/or times of release (sustained, pulsed, delayed, bolus followed by sustained, etc.).

Agents are released upward and diffused into a larger region, or released downward into a relatively smaller region of a target tissue. The precise control over the transport time as a function of distance from microwells provide a local concentration of a first agent as a function of distance from the microwell, at multiple time points following in vivo implantation.

Concentration gradient regions are defined as the distance from the microwell increases, the concentration of the agent being administered decreases. Cleaved caspase 3 positive cells as percent area of 3, 3'-diaminobenzidine (DAB) staining as a function of distance from the microwell is one example of a functional readout from the implanted drug delivery system. The agent concentration gradient is formed approximately 100-250 μm from the microwell with tissue concentration as greatest in the regions closest to the microwell.

The system is used to deliver a microdose of a ferroptosis-inducing agent to a tissue in vivo. The system is also used to deliver a priming agent (e.g., anti-ferroptosis rescue agent (M)), followed by a ferroptosis-inducing agent (e.g., ferroptosis-inducing agent (C)) to a tissue in vivo to induce targeted cell death in the tissue. The system is also implanted directly into tumor of about 6 millimeters (mm) to about 7 mm in diameter to achieve a minimum amount of about 10 ng/mm$^2$ of drug at the site of the microwell for at least 4 hours.

What is claimed is:

1. A method of treating a cancer in a tissue of a subject by inducing ferroptosis in the tissue of the subject in vivo, the method comprising:
    administering to the subject a priming agent; and
    administering to the subject a ferroptosis-inducing agent in an amount sufficient to achieve a concentration of at least 1 μM of the ferroptosis-inducing agent in the tissue wherein the tissue of the subject is contacted with the ferroptosis-inducing agent for a period of at least 24 hours,
    thereby inducing ferroptosis in the tissue in vivo and treating the cancer in the tissue of the subject.

2. The method of claim 1, wherein the ferroptosis-inducing agent is an inhibitor of glutamate-cysteine ligase.

3. The method of claim 1, wherein the achieved concentration of the ferroptosis-inducing agent in the tissue is from 1 μM to 10μM and the ferroptosis-inducing agent is contacted with the tissue for a period of at least 48 hours.

4. The method of claim 1, wherein the ferroptosis-inducing agent is an inhibitor of glutathione synthetase, glutamate-cysteine ligase, phosphoseryl-TRNA Kinase (PSTK), Eukaryotic Elongation Factor Selenocysteine-TRNA Specific (EEFSEC), Selenophosphate Synthetase 2 (SEPHS2), Sep (O-Phosphoserine) TRNA:Sec (Selenocysteine) TRNA Synthase (SEPSECS), or SECIS Binding Protein 2 (SECISBP2).

5. The method of claim 4, wherein the inhibitor is a small molecule, a peptide, or a nucleic acid.

6. The method of claim 1, wherein the ferroptosis-inducing agent is selected from the group consisting of: (1S,3R)-RSL3, ML-162, ML-210, JKE-1674, JKE-1716, erastin, jacaric acid, buthionine sulfoximine (BSO), trigonelline, glutamate, sulfasalazine, auranofin, brusatol, trigonelline, FIN56, FINO$_2$, CIL56, dihydroisotanshinone I, GPX4-IN-3, an analog of any of these, a derivative of any of these, and any combination of the foregoing.

7. The method of claim 1, wherein the ferroptosis-inducing agent does not comprise an iron-oxide or a sorafenib.

8. The method of claim 1, wherein the tissue of the subject is contacted with the ferroptosis-inducing agent for a period of 24 hours to 48.

9. The method of claim 1, wherein the tissue is cancerous and comprises a plurality of cancer cells.

10. The method of claim 1, wherein the tissue is cancerous, and comprises a carcinoma, a melanoma, or a sarcoma.

11. The method of claim 1, wherein the tissue is cancerous and the tissue that is cancerous is selected from the group consisting of: breast, brain, pancreatic, prostate, skin, bladder, lung, liver, ovarian, renal, endometrial, colorectal, gastric, skin, head and neck, and thyroid.

12. The method of claim 1, wherein the ferroptosis-inducing agent reduces tissue size or tissue volume by at least 5%.

13. The method of claim 1, wherein the ferroptosis-inducing agent is administered with one additional agent.

14. The method of claim 13, wherein the additional agent is a cell death-inducing agent or a dietary supplement.

15. A method of inducing ferroptosis in vivo in a tissue of a subject, the method comprising:
    administering to the subject a priming agent; and
    administering to the subject a composition comprising a ferroptosis-inducing agent in an amount sufficient to achieve a concentration of at least 1 µM of the ferroptosis-inducing in the tissue and to achieve a distribution of 10 ng/mm$^3$ of the ferroptosis-inducing agent in the tissue for at least 4 hours, wherein the tissue of the subject is contacted with the ferroptosis-inducing agent for a period of at least 24 hours,
    thereby inducing ferroptosis in the tissue in vivo of the subject.

16. The method of claim 15, wherein the concentration of the ferroptosis-inducing agent achieved in tissue is from 1 µM to 10 µM.

17. The method of claim 15, wherein the administering comprises administering 10 µg of the ferroptosis-inducing agent per kg of subject body weight per day to 10,000 mg of the ferroptosis-inducing agent per kg of subject body weight per day.

18. The method of claim 15, wherein the tissue is cancerous, exhibits hyperplasia, or exhibits fibrosis.

19. The method of claim 15, wherein the concentration of the ferroptosis-inducing agent achieved is the tissue is from 1 µM to 10 µM; the administering comprises administering 10 µg of the ferroptosis-inducing agent per kg of subject body weight per day to 10,000 mg of the ferroptosis-inducing agent per kg of subject body weight per day; and the subject has a cancer, a fibrosis, or an autoimmune disease.

* * * * *